(12) United States Patent
Moriya et al.

(10) Patent No.: US 8,383,798 B2
(45) Date of Patent: Feb. 26, 2013

(54) POLYNUCLEOTIDE ENCODING A CELLULASE ENZYME AND METHOD FOR PRODUCING THE ENZYME

(75) Inventors: Shigeharu Moriya, Wako (JP); Toshiaki Kudo, Wako (JP); Tetsushi Inoue, Wako (JP); Nemuri Todaka, Wako (JP); Katsuhiko Kitamoto, Tokyo (JP); Manabu Arioka, Tokyo (JP); Junichi Maruyama, Tokyo (JP)

(73) Assignees: Riken, Wako-shi (JP); The University of Tokyo, Tokyo (JP)

( * ) Notice: Subject to any disclaimer, the term of this patent is extended or adjusted under 35 U.S.C. 154(b) by 212 days.

(21) Appl. No.: 12/529,544

(22) PCT Filed: Jan. 18, 2008

(86) PCT No.: PCT/JP2008/051027
§ 371 (c)(1),
(2), (4) Date: Sep. 2, 2009

(87) PCT Pub. No.: WO2008/108116
PCT Pub. Date: Sep. 12, 2008

(65) Prior Publication Data
US 2010/0221807 A1    Sep. 2, 2010

(30) Foreign Application Priority Data

Mar. 2, 2007    (JP) ................................ 2007-053122

(51) Int. Cl.
*C07H 21/04*    (2006.01)
(52) U.S. Cl. ....................................... 536/23.2
(58) Field of Classification Search .......................... None
See application file for complete search history.

(56) References Cited

FOREIGN PATENT DOCUMENTS

| JP | 2003 70475 | | 3/2003 |
|----|------------|---|--------|
| JP | 2003070475 | * | 3/2003 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Kitamoto et al, Molecular biology of the Koji molds Advances in Applied Microbiology vol. 51, 2002, pp. 129-153.*
Brenda The Comprehensive Enzyme Information System. E.C. numbers for "cellulase". Downloaded Sep. 17, 2011.*
Hongoh et al, Intra- and Interspecific Comparisons of Bacterial Diversity and Community Structure Support Coevolution of Gut Microbiota and Termite Host. Appl Environ Microbiol. Nov. 2005; 71(11): 6590-6599.*
USPTO in house BLAST search of "MFKVLVKVTIALFCLHAVAAGEQRPKWTWELDG" from Todoka et al, FEMS Microbiol Ecol. Mar. 2007;59(3):592-9. Epub Jan. 18, 2007 (Fig 4; "2038B-11").*
USPTO in house BLASTalignment GenBAnk AB274537 vs SID79 performed Feb. 24, 2012.*
Todaka et al, Heterologous expression and characterization of an endoglucanase from a symbiotic protist of the lower termite, *Reticulitermes speratus*. Appl Biochem Biotechnol. Feb. 2010;160(4):1168-78. Epub Apr. 29, 2009.*
Todaka, Nemuri et al., "Shiroari Chonai Kyosei Gensei Seibutsu Cellulase no Kojikin ni yoru Seisan to sono Kosogakuteki Kaiseki", Japan Society for Bioscience, Biotechnology, and Agrochemistry 2007 Nendo, (Heisei 19 Nendo) Taikai Koen Yoshishu, p. 61, 2A15a12, Mar. 5, 2007, (with English abstract), Abstract only.
Todaka, Nemuri et al., "Environmental cDNA analysis of the genes involved in lignocellulose digestion in the symbiotic protist community of *Reticulitermes speratus*", Federation of European Microbiological Societies, vol. 59, pp. 592-599. Jan. 18, 2007.

* cited by examiner

*Primary Examiner* — Sheridan Swope
(74) *Attorney, Agent, or Firm* — Oblon, Spivak, McClelland, Maier & Neustadt, L.L.P.

(57) ABSTRACT

This invention provides: DNA encoding cellulase enzymes from intestinal symbiotic protists of the insects of *Reticulitermes speratus, Hodotermopsis sjostedti, Neotermes koshunensis, Mastotermes darwiniensis*, and Cryptocercidae, comprising the nucleotide sequences as shown in SEQ ID NOS:1 to 140; an expression system for the DNA; and a method for producing the cellulase enzymes using the expression system.

7 Claims, 7 Drawing Sheets

Fig. 3
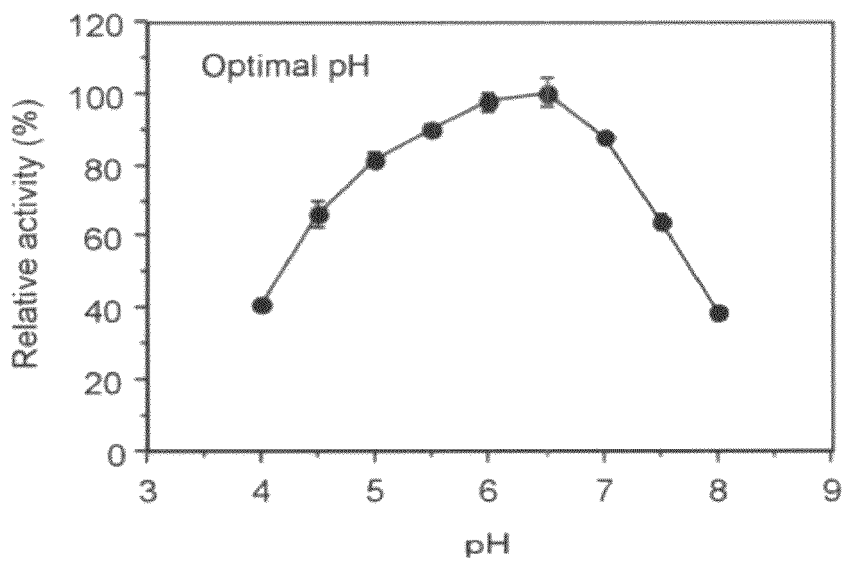
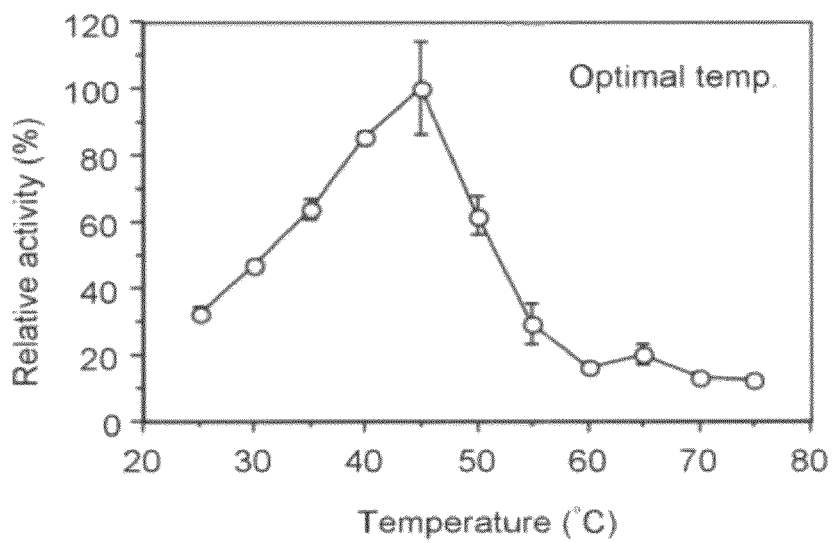
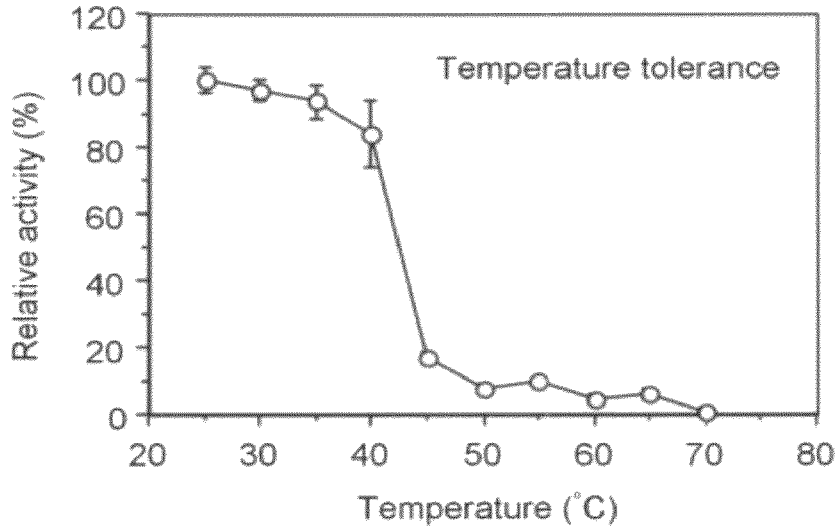

Fig. 4

| Organism | Specific activity (unit/mg protein) | Optimal temp. (°C) | Optimal pH | Km (mg/ml) | Vmax (unit/mg protein) |
|---|---|---|---|---|---|
| Roach | | | | | |
| *Panesthia cribrata* | | | | | |
| EG1 | 171.1 | | | 9.4 | 123.2 |
| EG2 | 318.2 | | | 6.8 | 490.1 |
| Lower termites | | | | | |
| *Reticulitermes speratus* | | | | | |
| YEG1 | 73.6 | 50 | 6.0 | 1.83 | 527 |
| YGE2 | 83.4 | 50 | 6.0 | 1.48 | 540 |
| Symbiotic protist | | | | | |
| Host: *Coptotermes formosanus* | 105.0 | 70 | 6.0 | 1.90 | 148.2 |
| Host: *Reticulitermes speratus* | 603 | 45 | 6.5 | 1.97 | 769.6 |
| Bacteria | | | | | |
| *Clostridium cellulolyticum* | | | | | |
| CelCCA | 64.3 | 37-51 | 5.5-7.2 | 1.97 | 60.8 |
| CelCCC | 44.8 | 48 | 6.0 | 1.00 | 50 |

SEQUENCE LISTING

<160> NUMBER OF SEQ ID NOS: 145

<210> SEQ ID NO 1
<211> LENGTH: 2061
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgtttggcc tatttgtttg tttgacattt gcttctcctc ttccaggagg ttattatcac      60
gcacgagggc atgatattgt tgatgagact gacactattg ttcagttatg gggtgtaaat     120
tggtggggtg ctgaatctgg cgaatgtttt ccaacaaaca aagactggaa tcttgatgaa     180
ctaattaatc aagtagattc aaaaggtttt aacacctgga ggtttccaat ttctgccgat     240
cgtgttcacg aatggatcgg tgactgggca gaatatggag ctgcagaaga ttattgtaag     300
aagaataatc taaagtggtt tgaagacttg attgagaagc tgtcggcaaa agggcacaaa     360 ttaattttg atattcattc attacatgga aatacttaca gggacaattt gtggtttaag     420
aagggatacg gaccagatta tattattgaa gctcttgagt ttcttgcaga gcattttaat     480
gaaagcgaca cagtgattgg acttgatctc aagaacgagc ctcatggttt gtgccaaaac     540
aatcatggat acaactacag tgaaaatggt ttatttgatg gtgaccaacc tgcttttgaa     600
ggcggtgact ttggagcttt agtatccaca aaatgggata ttcttctga cgacaacaac     660 tggaagcatt ttattgaaac agctggtaat cggattcatg ctaaaaatcc gaatttactt     720
attttggttg aaggaatcga atgctacaat ggtcatacaa catggtgggg aggaaatctt     780
gaagcagtta aagattatcc gattacattg aatgtcccta acaaagttgt ttatagtcct     840
catgattatc ctggtgaagt gaatgcagga agcggtcgag gatggttttg tgatgaaact     900
aatttcaata caatgtggac agaagcttgg cttccttatt gggactatat ttatttagaa     960
aatattgcac ctattttgat tggtgaatgg ggtcttaaat tcgaaaaaga gcaaggacaa    1020
tggactgagc gaaagtgggt tgaagcaagt tgtacgcctg gaaaatggca tactacccaa    1080
ttctgggaaa attcacacaa tgatggttgg gctgctgctt atatcactgg tggaagtgta    1140
acacctggtc attgggccaa caaaactgaa caactccctg aacgcgctgt acttaaaaat    1200
ctgaattatg gtgttgttct tcctccaaga actgcgcaaa ttggcgaatg ggttcatact    1260
```

-continued

```
tactatacgg ggaattatga aattcatcca gaatgttcta agagttgcaa ctctattgaa    1320
tttgttccat tttatgcacc cgatgaatgc gttgagggcc attgggtaat tgatttcgtt    1380
aaagcagaag gtgtaggcga aaatatacaa gccacaacat ggtttcggaa tcttacgcgt    1440
cttatccatc aacaaaatct ttctcaaacg ttttggtcat tgaacccagg atcagatgac    1500
actgatcctt taatctggac agaatggata aatggccagg aaaaatttgt ctggaaagaa    1560
attttgttag aagttattaa tggttcaatt ttaaattcaa ccgaattaac aactcctcct    1620
aaagaagaac acgcttgtcc tgtagatcca ccttatgatc ttgaaactgt ttatccttcc    1680
atagtctcat ctaatcctcc aaaatcatcg tttgaaacta tttcaagcga gtctgaaaat    1740
tctagttctc aacctgaggt cgtgcctcca gtggataatc cttctaacca aaacgatggt    1800
tctaatgccg gtttgattgg aggacttgtc ggtggaattc ttgctttggt tgcaggtgct    1860
cttattgctg catactttat tcttcggaaa aagaaacttc catcagaaat gagcgatgga    1920
cttgaacctg aaagcgttgc tcctaatatt cccaaacaaa ataatattct gactcaagaa    1980
aatcctcttt gggaacatga tgaatttgct caaggtgacg aatttaatga aattgatgaa    2040
attattccca attcgattta a                                             2061
```

<210> SEQ ID NO 2
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgtttgttc ttttgcttct tcaaatcatc aactcgaaag cacctccatt cggaaggctt      60
cgagttgaag ggaataagat tgttggggag aaacgagctc aggaatgct tcgtggtgtt     120 tgcctctcat ggcataactg gtggaagcaa ttctacaatg ctaacaccat caaccacttg     180
aaaactgatt tccatgccaa cgttatccga gcagcaatcg gtgtcgatgc agacggtgga     240
tacttcgaca ataaggataa tgcatattct tgcctctatg cagcagttga tgctgctatt     300
aacgctggaa tttacgcaat tgttgattgg caaacatttg tgattcacga atctgatgca     360
aagcagttct tcacaacagt tgcaaccaag tacaaaggaa atcgaacgt gatctacgat     420 attttcaacg aaccagaagc cgcaaaatgg ccagagatta agcttattc aatcagcttg     480 attggcacca tcagagcaat tgatcctaat gcctttatcc ttgttccaac accaaactgg     540
gatcagtacg ttgaacaagc agctgcagat ccaatcaccg aatattcgaa catcgcttac     600
acgatccata tttatgctgc tacgcatccg ttgtcttact tggataacgc ccgtgaagca     660
atcaaaacca ttcctctttt tggaggcgaa attggtgcaa tggaggcaag tggagatgga     720
gcattggatg ttaccaagta caacacctgg atttccttt atgaagagaa tagcattcct     780
tatctttgct gggctgttca atccaagcaa gaaacatgct caatcctgaa accaagtgaa     840
gattggaacg acttgaccga atggggcaaa ctctgcaagt ccacaatcac tgctcatcag     900
taa                                                                  903
```

<210> SEQ ID NO 3
<211> LENGTH: 1047
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgcgttttt tcctggttta cttcttttcg tgcatatttt ctgctgactg gttgtctacc      60
agtggaaata aaattgttga tagtggagga aatcaagtca agcttcaagg gctcaattgg     120
tttggatacg aaacacaaat gagagttttc cacggcctat gggctgcaaa tctgcatgac     180
actgttgcag aagttgccag acgaggcttc aatgttttca ggtgtccatt ttctgcagat     240
cttcttcatg aatggtcatc aggtaaatat gaaccagtac aaattaatcc aaatgtaaac     300
gctgatttga atgggaagaa taatcgggaa atctgggatg actttcttgt tgattgcaaa     360
aaaaatggag ttaaggtgtt tatcgacata catggagttg aacctgatca gtatcaagac     420
gcaacatggg gaaaacccga gtatatttac accgcacttg aatggtttgc caacgaattc     480
aaaagtgatg acacaattat cggcattgat ataaagaatg aaccgcatgg gcagtgtgat     540
tatgcggaca agcaatctg ggattcgagt acggctgaca caactggcg gagtactgca      600
gccactgctg cctcacgtat ccatgcaaaa aatcctaatc ttttgatttt tgttgagggt     660
attgagtgtt ataatggacc aagaggcata gagagtggtt ggtggggtgg ggtgttgacc     720
tttgttaaag acctgcccct tgatttaggc agtcatcagg ataagcttgt ttattctccc     780
cacgaatatg ggccaacagt gttcaaccaa acttggttca atcctacctt tacttatgat     840
tcgatttaca atgatcactg gaaggattca tggatgttca ttcacgaaca ggatattgct     900
cctcttcttt tcggagagtg gggtggcaaa ttggagggga caaataccga ttggatgaca     960
tatatggtgc agttgatttc aaagaataac ctcagtcaca cttttggtgt ctcaatccga    1020
acagcggaga cactcaagga cttctga                                        1047
```

<210> SEQ ID NO 4
<211> LENGTH: 912
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgtttggga ttctgtacgt gatcgcatca ctggtgtaca tggagctgaa cgatgctcgg      60
ttgagggtga aggacaacaa aattgttgtg ggaaacagcg acaagggcct tcgacttcgt     120
ggagtcaatt tgagttggaa caactggtgg catcagttct acaatgctga cactgttaga     180
cacttgaaga atgacttcca cgtgaacgtt attcgagcag caatcggagt tgaacaggat     240
ggtgggttct atcaaaatga atcaggatcg tacaatgatt tgtatgccgt catagatgct     300
tgcatcgcaa ataatatcta tgtgatcgtt gattggcaaa cattttcggt gaagcacctt     360
acgaatgcca ccaagttctt cacgcaagtt gcgaacaaat atcactcaag cccttacatc     420
atttatgatc ttctgaatga acccgatgat tcgaacacat ggtctcaaat caaaagctat     480
gcagaatctc ttattaagac gatccgtgcg attgattcca gcaatctgat tatttgtgggt    540
acaccgaatt gggatcaata tgtcaaacag gcagctgctg atccagtgac aggggacaac     600
aacatcattt attcaattca tatctatgtt ggaacacatc cgatgtctta catggacgat     660
gcgagggaag ctctgaaaac gattggtctt tttggtgggg aaattggtgc aatgaatgca     720
gatggtaatg atcgttgga tactgcaaag ttcaatcaat ggattgattt ctatgaacag     780
aataaaatat cgtggctgtg ctgggcagtt cagtcgaaat cagagactga ttcgcttttg     840
aaaccatctg aaagctggac tgatctgacc gaatggggga atttgtgcaa gagcaccatc     900
accaaatatc aa                                                         912
```

```
<210> SEQ ID NO 5
<211> LENGTH: 792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgaggaaag caatgtttgt gggtcttttt ttgattgcgc ttgtgcatat ggaactggaa      60
aacaactcca ctcggctgag ggtgaaaggc aataaaattg ttgtgggaaa tagcgacaaa     120
ggactccgac ttcgtggtgt taatttaagt tggaacaatt ggtggcatca attttacaat     180
gctgatactg ttaggcattt gaagaacgat ttccatgtga atgttattcg agcagcaatt     240
ggagttgaac aagacggtgg gtgggaaagc aacaaacaaa ggtcttatga tgatttgtat     300
gcagttattg atgcttgtat tgcaaacaat gtttatgtga tagttgattg caaacatttt     360
tcaattaaat taagtgaggc gactgaattt ttcacgaatg ttgccaacaa atatcattca     420
agcagttata tcatttatga tcttctgaat gagccagaca gttcagtgcc gtcatggtct     480
gccatcaaaa gttatgcaga agtctcata aagacaatcc gagctattga ctcaagtaat     540
ttgattattg ttccgacacc gaattgggat caatatgtta acaagctgc tgctgaccca     600 attacaagtg acagtaacct tatttattct atccatattt atgttggaac acatccgatg     660
tcttacatgg acgatgctag agaggcactt aaaactattc ctcttattgg tggcgaaata     720
ggtgcaatga atgcagatgg tgatggagcg ttggatgtgt cgaaattcaa tcaatggatt     780
gatttcctat ga                                                        792

<210> SEQ ID NO 6
<211> LENGTH: 1119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgtttgctt tcttctctc gaccacattt tcagccaatt ggttatcaac cagtgggaac      60
aagattgttg acggcagtgg aagccaggtg aagcttcaag gcttgaactg gtttggcttc    120
gaaacatccg ttggctgctt ccatggtctt tgggcagcaa atcttcatga catggtctct    180
gaagttgcta acgtggatt taacgttttc cgtgtcccag tttctgcgga tcttcttcac    240
acatggcttg acaagaagcc tgaagttcca tcttccatga cccacaggt taaccccgat    300 ttggatgggc tgacgaaccg cgagatcttt gacctgtttc ttgttgattg caaaaggagg    360
gcctgaaggt attcatcgat gttcacggaa ttgcgcccga ctcatatacc gatgctcttt    420
ggggcacacc cgaataccct tacaaagctg ttgagttctt tgccgatgcc tacaaggatg    480
atgataccgt catcggaatt gatatcaaga atgaacccca tggagaatgc ggctcaagct    540
ctggtgctac ctgggacagc tctaccaccg ataacaactg gcattatgtt tcccttgacc    600
gcggcgaacc gcatccttgc aaagaatccc aacctttaa tcctcgtcga aggcattgct    660
tgctacaagg gtccacgtgg ccaggacaat ggctggtggg tggcgttct ctcatttgtc    720 aaagatcttc cactcgatct cggcaaatac caaaacaagc ttgtctacag ccctcacgag    780
tacggtccat ccgtcttcga ccaatcatgg ttccaaggtg acttcactta tgattccctc    840
tacaacgacc actggaagga ctcatggatg ttcatccatg aggacggaat cgccccctg    900
```

```
ctgatcggag aatggggtgg ccacatccag ggcacaaaca cgaagtggat gcaattcatg      960
gttcaactca tccagaagaa cagcctcggc cacacgttct ggtgccttaa cccgaactcc     1020
ggcgacaccg gtggcctcat caatggcgac tggctcacct gggacgagga gaagtacgac     1080
ctcatcaagc ccgcggtctc cggcaaactc ttcaagtag                            1119
```

<210> SEQ ID NO 7
<211> LENGTH: 903
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 7

```
atgttcgcga ttctttgttt aattggaatt gtccaaagca atcctccatt tggtcgctta       60
agtgtgaaag gtaatcaaat tgttggtgaa agccagaaag gagtccaact tcgtggtgtt      120
ggattaagtt ggcataattg gtggcatcaa tttatactg ctgatactat taacatttta       180
aagaatgatt ccatgcgaa tgttgttcga gcagcaattg tgttgaaaa agaaggtggg        240 ttttttgatg atgagaatag agcttatgaa gacttatatg cagttattga tgctgcaatt     300
gcaaatggta tctatgtaat agttgattgg caagcatttc aaacccattt acctgaagct     360
actaaattct ttcaaaaagt tgctgataaa tatcactcaa gcagctatat tatttatgaa    420
cttttcaatg aaccagaaag tgcttcatgg tctgaaatca aagttatag tgaatctctt      480 attaaaacaa tccgagctat tgattcaaat aatttgattc ttgttccaac accaaattgg     540
gatcaatatg ttaaacaagc tgctgctgat ccaattacaa ttgacaataa cattgcttat    600
acaattcata tttatgttgg aacacatccc ttgtcttaca ttgatgatgc taaagaagca    660
cttaaaacga ttcctctttt tggtactgaa attggtgcaa tgaatgcaga tggtgatgga    720
gctttggatc gtgcaaaatt cactcaatgg attaatttct acgaagaaaa tcatatttct    780
tatcttgcat gggcagttca atcaaaacaa gagtctgatt caattttgaa accatctgaa    840
aattggaatg atctaagtga atggggtact ttgttcaagg aaacaattac tcgttatcag    900
taa                                                                  903
```

<210> SEQ ID NO 8
<211> LENGTH: 903
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 8

```
atgctatttc ttctttgcat tggactttct ttccaaaaaa catatggtcg attaagtgtt       60
aaaaatggta aaattgttgg aaaaagcaaa gctggcgatc ctatattaag aggtatttct     120
ttaggatggg atacttggtg gagccaatat tataacgctg attctattaa tcatttagtt     180
actgattttc atgcaaatat tattcgagct gcaattggaa ttgaaccaag tggtggttat    240
cttgaaaata acaaaaagc acttactaat ctttatgccg cagttgatgc tagtcttgca     300
caaggtgttt atgtaattat tgattttcat gctcatcaag ttcatactgc cgaagcaaaa    360
gaattcttta caacgttgc aaccaaatat gcaggaaacg aattgattat ttatgaaatc    420
ttcaatgaac cagaaagtgc aacctggagc gaaatcaaaa cttatgcaac tgatgtgatt    480
aagaccattc gtgcaattga tcctgataat ttaatttag ttcctactcc tcaatgggat      540
```

```
caattgattg atcaagctgc tagtgatcca cttacaggtt ttgataatat tgcatacact      600
cttcactttt acgctgggac tcatggtcaa tcattccgag acagaggtca aaaagcagtt      660
gatgcaaaac ttgctgtttt catttctgaa agtggtgcaa tgaatgctga tggagatggt      720
tcgcttaata agaatgaatt cgaaaattgg attaattggg ctgaaactaa taatattcca      780
tgggttgtat ggtgccttga aagcaaagct gaatcagctt caatcttacc tgctacagga      840
ggttgggctc aattaactga atggggaact tacattaagg cacttattac aaagtaccag      900
taa                                                                   903
```

<210> SEQ ID NO 9
<211> LENGTH: 906
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
atgttgtttg caattttgct tcttcaattc atcgattcta aagcgccacc tttcggaaga       60 cttcggggttg aaggcaacaa gatcgtcggc agtaaacgag caccaggaat ggttcgggga     120
gtcggtcttt cgtggtccaa ctggtggcca caattctaca acgcagatac gatcaaccac     180
cttaagaatg atttccacgc gaacatcatc cgcgcagcta tcggtgtcga aaaggaaggc     240
gggtactttg acaacaagga caatgcatac aaactccttt acgcagcagt ggatgcagcg     300 cttttcagcag gaatctacgc cattgtcgac tggcaagcat tccagattca tgaatcagat     360
gcgattgagt tcttcacaaa agttgtgaac aattacaaag gaaagtcgaa cgtcatttac     420
gagatcttca acgagccaga aagcgcaagt tggtcacaga tcaaatcata ttccatcaac     480
ttgatcaaaa cgatcagagg aatcgattct aatgcttttca ttcttgttcc aacaccaaac     540
tgggatcagt acgtcgagca agcagcagca gatccaatca ccgagtactc aaacatcgct     600
tacaccatcc acatctacgc agccacacat ccattgtcgt acttggacaa tgcgagagca     660
gccctcaaca aaattgcact tttcgggaca gaaattggag caatggaagc aagcggagat     720
ggagcaatcg atctgaacaa gtacaaccaa tggatcgact tttatgagca agttcagatt     780
ccttatcttt gctggggtgt ccaatcgaag gatgaaacga actccattct gaagccaagt     840
gagaactgga acgacttgtc tgaatggggc aatctttgca agaaaacaat cactgctcat     900
cagtaa                                                                906
```

<210> SEQ ID NO 10
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
atgcttgcat ttctttgttt tattggaatt attcaaagtc aagctccatt tggtcgttta       60
agtgtgaaag gaaataaaat tgttggagaa agccaaaaag gagttcaact tagtggtgtt     120
ggattaagtt ggcataattg gtggagtcaa ttttatactg ctgatacagt gaaacatctt     180
aagaatgatt tcatgctaa tgttgttaga gcagcaattg gtgttgaaaa ggagggtgga     240
tattatgata taagcaaaaa agcttatgat tcccttatatg cagttattga cgctgctatt     300
gcaaatggta tttatgtaat tgttgattgg caagcatttc aaatccattt aagcgatgca     360
```

-continued

```
accgaattct ttactcaagt tgctaacaaa tataaaggta gtcaatatat tatttatgag      420
ctctttaatg aaccagaaag tgcttcatgg tcagaaatta aaagctattc tgaatctctt      480
attaaaacaa tccgagcaat tgattcaagt aatttaattc ttgttccaac accaaattgg      540
gatcaatatg ttaaacaagc tgctgctgat ccaattacaa gtgataataa tattgcttat      600
acaattcata tttatgttgg aacacatcct ttatcgtata ttgatgatgc tcgtgaagca      660
cttaaaacaa ttcctctttt tggtactgaa attggtgcta tgaatgcaga tggtgatgga      720
gcattaaacg ttgataagtt taatcaatgg attaatttct atgaagaaca gaaaatttct      780
tatcttgcat gggcagttca atcaaaagaa gagtctgatt caattttgaa accatctgaa      840
gattggaatg atctttccga atggggtaaa ttgttcaaac aaacaattct taaatatcag      900
taa                                                                   903
```

<210> SEQ ID NO 11
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgcagggac tgatcctgct gctcgctgga gttctttcag cagattggtt gcatgtcgat       60
gggacggcca ttgtaaatga ggcgggcgag gaagttttcc tgacggggtt gaattggttc      120
ggcttcgaaa cggacattcg cgtgatccac ggtctatggc aatcgagctt gcacacgatt      180
gtcaaggagg ctgctgcaca tgggttcaac gtttggcgta ttcctgtctc tgctgacacg      240
ctcggccagt ggcgagacgg agaagagccg ttggacacat ggattgaccc tactgcaaat      300
cctgatcttc agggacttgg cgggtttgaa atctttaaca tcttcttgga cgattgccgg      360
gctaatggaa tgaaggtctt cgttgacatt cacaacatgg agccgggccc gcagaacccg      420
ttcccatacg agcccgatca ccccggtgat cctcctgagt actactacgg agttcttgag      480
tggcttacaa agcagtactt ggacgacgat gtaataattg gatcgacct tttcaacgag      540 ccgcacagtg tgcacgattg tggcgatccg cagactgagg aggattgcct gtgggacgac      600
tcggagaagg tgaacaactt ccgctacgtg gcgagcgaag ccggcaagcg catactggcg      660
attaacccga atttgctcat tattattgag cttccgggat gctaccacgg cggcttcggc      720
tggtggggcg gcacgctcca gggcgtcggt gacgtgctcg ccgatcttcc ggcgacgaac      780
gtggtgtaca gcccgcacga gtacggcctg ggagtgtgga actcggacgc ggagtggctg      840
aagccgggct ttcatacga ctcgctgatg gagaaacact ggctacctca ctggctgttc      900
gtgaagaagg atggaatcgc gccggtgctg atcggcgaat ggggcggcac aaccgagggc      960
gaaaacgcga actggattgg attcgtggcg gacctgatcg gcaaggaggg cctgagccac     1020
acttactggg acttgaaccc ggatagcagc ggcactggtg gtttgctgct cgatgactgg     1080
gcgacgtggg acgaggagaa actcgggctg atcgctccat cgctcaccgg gaagctctgg     1140
ccgacaaagg agccccgcgg gaaagtggtg aagaaggcgt ag                         1182
```

<210> SEQ ID NO 12
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atgtttgcga ttctttgttt aattggaatt gtccaaagca atcctccatt tggtcgctta      60
agtgtgaaag gtaatcaaat tgttggtgaa agccagaaag gaatccaact tcgtggtgtt     120
ggattaagtt ggcataattg gtggcatcaa ttttacaatg ctgatactgt aaacattta     180
aagaatgatt ccatgcgaa tgttgttcga gcagcaattg gagttgaaaa agaaggtgga     240
tattatgatg atcaaaatag agcttatgaa gacttatatg cagttattga tgctgcaatt     300
gcaaatggta tctatgtaat agttgattgg caagcatttc aaatccactt aagtgatgct     360
acttcattct ttactaaagt tgctaccaaa tatcactcaa gcagttatat tatttatgaa     420
cttttcaatg aaccagaaag tgcttcatgg tctgaaatca aaagttatag tgaatctctt     480
attaaaacaa tccgagctat tgatccagat aacttgattc ttgttccaac accaaattgg     540
gatcaatatg ttaaacaagc tgctgctgat ccaattacaa ttgacaataa cattgcttat     600
acaatccata tttatgttgg aacacatccc ttgtcttaca ttgatgatgc taaagaagca     660
cttaaaaaga ttcctctttt tggtactgaa attggtgcaa tgaatgcaga tggtgatgga     720
gctttggatc gtgcaaaatt cactcaatgg attaatttct atgaagaaaa taaaatttct     780
tatcttgcat gggcagttca atcaaaacaa gagtccgatt caatttttgaa accatccgaa     840
aattggaatg atctaagtga atgggtact tgttcaagg aaacaattac tcgttatcag     900
taa                                                                  903
```

<210> SEQ ID NO 13
<211> LENGTH: 1125
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
atgagtcttg tcattttttt cactcttctg aaaattgctt tttctgctga cgctgatttg      60
ccaaatgatg cccctaaact tgcggcaaaa cttgggtttg gttggaattt agggaatgct     120
ttagagtcat gcagtgattc taattctgct tctgaaacat cctggggaaa tcctgccaca     180
acccaagctt taattgatgc agttaaaaag gctgggttca acacagttcg aattccttcg     240
gcttggagtg gctacattga aaatacaacg acttataaaa tcaaggattc atggttgaaa     300
agagtatcag aagttgttaa ctatacaatc aaaaatgaca tgtacgcaat tttgaatatt     360
cattgggatg gtggctggct tgaagaaaat ccaacatttg acaaacaaaa agaagttaac     420
gcgaaacaaa aggctttgtg gactcaaatt gcaacctatt ttgaaggtta tgatgaacat     480
ttacttttttg ctggaacaaa tgaagttcgt aaagattatg gtacaccatc agatgaaaat     540
attgaggttc aaaattcgta ccttcagact tttgtggatg ctgttcgtgc aacaggtggg     600
aataataaaa ttcggaattt ggttgtgcag ggttacaaca caaacattga acatacggtg     660
aattatttaa ggataccttc tgacaatgca actcatcgtc tcctagttga aattcatttt     720
tatgatccat atgattttgc aggtgaaggt aattcgcaaa actatctctg gggaaaatct     780
tatgctaatt ctggacatgt tcatcatgg gacaagaat cttgggttga tgaagcattt     840
ggaatgttga aaagaattt tgttgataaa cagtatccag tgattctcgg agaatatggg     900
gcggttcatc gaacacatct tagtggtgat gaccttgttc aacatactgc tgcaagaaaa     960
tattacttga attatgtaac ccaagcagca cttacgaatg gagttgttcc atattactgg     1020
```

```
gataatgggg gtactggtga taatggtttt ggattgattg atcgtaataa ttattctcaa    1080
gctttccctg atgacattaa agcaattaca tcagcaaaac gataa                    1125

<210> SEQ ID NO 14
<211> LENGTH: 912
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgtttgtga tcctttttt gattgcgctt gtgcacatgg aggtcaatgc gacgcttggg      60
cacttgaggg tgaagggcaa caagatcgtc gtcggaaata gtgacaaagg tctgagactt    120
cgtggcgtca atctgagttg gaacaattgg tggcatcagt tttacaatgc tgatactgtg    180
aggcatttga agaatgattt ccacgtgaat gtgatccggg cagcgattgg cgttgaacaa    240
gacggtgggt gggaaagcaa taagcaaagg tcttatgatg acttgtatgc agttaccgat    300
gcttgcattg cgaacagtat ttatgtgata gttgattggc aaacgttttc aatcaaattg    360
agcgaggcga cggaattctt caccaaagtt gctaaccagt atcactcgag caattatatc    420
atttatgatc ttctgaatga acccgacagt gctacatggg atcagatcaa gagttattca    480
gaaacgctga ttaagacaat ccgagctatt gacccgaaca atttgattat tgtgcctaca    540
ccgaattggg atcaatatgt taaacaagct gctgctaatc aattacaag cgacaacaac     600 atcatttatt ctatccatat ttatgttgga acacatccga tgtcttacat ggacgatgcg    660
agagacgcac ttaaaacgat tcctcttctt ggtggtgaaa taggtgcgat gaatgcagat    720
ggtgatggcg cttggatcg tacgaaattc aatcaatgga ttaatttcta tgaagaaaat     780
agaatcggct ggctttgctg gggagttcag tcgaagtcag agagttgttc tcttttgaaa    840
ccatcagaag attggaatga tctgaccgag tggggaagat tgtgcaagga acgatcact     900 aaatatcagt aa                                                        912

<210> SEQ ID NO 15
<211> LENGTH: 1074
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atggtattga tttatttg ccttattggt tggctttcaa caagtggaag taaaatttca       60
acgagattga gtggattgaa ttggtttgga tttgaaactt caaatgaagt tttccatggt    120
ttatgggcgg cgaacttaga agatcttgtt gcagaagttg caaaacgagg atttaatgtt    180
ttcagagttc cagtttcagc gtcagttttg caagattgga agctggaac acctaatgct     240 gatatcagta ttaatgccga agtaaatcca aatttagaag gattgaacaa tttacaagtt    300
tttgatgcat ttattgcaga atgcaagaag cacaacattt atgttttat tgatgttcat     360 ggagtaacag atggaagtta tatggataat ctttggtata ctagtgcaca tcctgctgaa    420
tggatttatg ctggtcttga atggtttgca gatcattata agagtgaaca aactattgtt    480
ggtattgatg ttaagaacga accacatgga aattgtgatt caagtgatgg tgctaaatgg    540
gatgattcta aagatgctaa caattggaaa tactttattg aaacagcagc aacacgaatt    600
catgcaaaga atcctgaact tttaataatt gttgaaggaa ttgcatgtta taaggtcat     660
```

```
ggtggctggt ggggaggaaa cctttatgca gttcgagatt atccaattaa tcttggatca      720
catcagaata aacttgttta ttctcctcac gaatatggtc cctcagtttc tcaacaaact      780
tggtttgaag aagtttcac ttatgattca ctttatgctg atcattggaa agattcttgg      840
```
*(line 840: `tggtttgaag aagtttcac` as shown)*

```
ttgtacattg ttgaagataa cattgcgcct ttgttaattg gtgaatgggg tggacatatt      900
gaagaaccaa atactagttg gatgaaatat atggttcaat tgattagtgg aaaaggtctt      960
agtcaaacat tctggtgttt gaatcctaat tctggagata ctggtggttt attgaaagat     1020
gattggttaa cttgggatga agaaaagtac aacttaataa aaggtgtgct ttaa           1074
```

<210> SEQ ID NO 16
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atgtttgcga ttctttgttt aattggaatt gtccaaagca atcctccatt tggtcgctta       60
agtgtgaaag gtaatcaaat tgttggtgaa agccagaaag gaatccaact tcgtggtgtt      120
ggattaagtt ggcataattg gtggcatcaa ttttacaatg ctgatactgt taaacattta      180
aagaatgatt ccatgcgaa tgttgttcga gcagcaattg gagttgaaaa agaaggtgga      240
tattatgatg atcaaaatag agcttatgaa gacttatatg cagttattga tgctgcaatt      300
gcaaatggta tctatgtaat agttgattgg caagcatttc aaatccactt aagtgatgct      360
acttcattct ttactaaagt tgctaccaaa tatcactcaa gcagttatat tatttatgaa      420 ctttttcgatg aaccagaaag tgcttcatgg tctgaaatca aaagttatag tgaatctctt      480
attaaaacaa tccgagctat tgatccagat aacttgattc ttgttccaac accaaattgg      540
gatcaatatg ttaaacaagc tgctgctgat ccaattacaa ttgacaataa cattgcttat      600
acaatccata tttatgttgg aacacatccc ttgtcttaca ttgatgatgc taagaagca      660 cttaaaaga ttcctctttt tggtactgaa attggtgcaa tgaatgcaga tggtgatgga      720
gctttggatc gtgcaaaatt cactcaatgg attaattct atgaagaaaa taaaattct      780 tatcttgcat gggcagttca atcaaaaacaa gagtccgatt caattttgaa accatctgaa      840
aattggaatg atctaagtga atggggtact ttgttcaagg aaacaattac tcgttatcag      900
taa                                                                    903
```

<210> SEQ ID NO 17
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
atgcttgtgc ttttacttct ccatttcatc aactcaaaag cacctccatt tggaagactc       60
cgcgttgagg gaaacaagat cgtcggcagc aagcgagcac caggagtgct tcgcggagtt      120
ggtctttcgt ggcacaactg gtggccacaa ttctacaatg cagccacaat caaccacctc      180
aagaacgact ccatgccaa cgtcatccga gcagctattg gtgtcgagaa ggagaacggg      240
tattttgacg acaaacagaa cgcatataag ttactttacg cagcagtgga tgcagcactc      300
tcagcaggaa tctacgtgat tgttgactgg caagcattcc agattcatga atcagatgcg      360
```

```
aaggagttct tcactgaagt tgtaaccaag tacaaaggta agtccaacgt catttacgag    420
atcttcaacg aaccagaaag cgcaggatgg tcagagatca aaaagtattc tatcagcttg    480
atccaaacca tccgagccat cgattctggt gcattcatcc tcgtcccgac accaaactgg    540
gatcagtatg ttgagcaagc agcagcggat ccaataaacg agtactcaaa catcgcttac    600
acaatccaca tctacgcagc cactcaccca ttgtcgtacc tggacaacgc acgcacagcc    660
ctcaagacaa tcgcgctctt cgggacagaa atcggagcga tggaagcgag cggggatgga    720
gcaattgatc aaagcaagta ccaacaatgg atcgacttct atgagcaaaa cgggatttct    780
tatctctgct gggctgtcca atccaaggaa gaaactgact ccatcctgaa gccaagtgag    840
gactggaacg acttgacagc ttggggcaag ctttgcaagt ccaccatcac tgctcatcag    900
taa                                                                 903

<210> SEQ ID NO 18
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atgtttgcga ttctttgttt aattggaatt gtccaaagca atcctccatt tggtcgctta     60
agtgtgaaag gtaatcaaat tgttggtgaa agccagaaag gaatccaact tcgtggtgtt    120
ggattaagtt ggcataattg gtggcatcaa ttttacaatg ctgatactgt taaacattta    180
aagaatgatt tccatgcgaa tgttgttcga gcagcaattg gagttgaaaa agaaggtgga    240
tattatgatg atcaaaatag agcttatgaa gacttatatg cagttattga tgctgcaatt    300
gcaaatggta tctatgtaat agttgattgg caagcatttc aaatccactt aagtgatgct    360
acttcattct ttactaaagt tgctaccaaa tatcactcaa gcagttatat tatttatgaa    420
cttttcaatg aaccagaaag tgcttcatgg tctgaaatca aaagttatag tgaatctctt    480
attaaaacaa tccgagctat tgatccagat aacttgattc ttgttccaac accaaattgg    540
gatcaatatg ttaaacaagc tgctgctgat ccaattacaa ttgacaataa cattgcttat    600 acaatcccata tttatgttgg aacacatccc ttgtcttaca ttgatgatgc taaagaagca    660
cttaaaaaga ttcctctttt tggtactgaa attggtgcaa tgaatgcaga tggtgatgga    720
gctttggatc gtgcaaaatt cactcaatgg attaatttct acgaagaaaa taaaatttct    780
tatcttgcat gggcagttca atcaaaacaa gagtccgatt caattttgaa accatctgaa    840
aattggaatg atctaagtga atggggtact ttgttcaagg aaacaattac tcgttatcag    900
taa                                                                 903

<210> SEQ ID NO 19
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgtttgcga ttctttgttt aattggaatt gtccaaagca atcctccatt tggtcgctta     60
agtgtgaaag gtaatcaaat tgttggtgaa agccagaaag gaatccaact tcgtggtgtt    120
ggattaagtt ggcataattg gtggcatcaa ttttacaatg ctgatactgt taaacattta    180
```

| | |
|---|---|
| aagaatgatt tccatgcgaa tgttgttcga gcagcaattg gagttgaaaa agaaggtgga | 240 |
| tattatgatg atcaaaatag agcttatgaa gacttatatg cagttattga tgctgcaatt | 300 |
| gcaaatggta tctatgtaat agttgattgg caagcatttc aaatccactt aagtgatgct | 360 |
| acttcattct ttactaaagt tgctaccaaa tatcactcaa gcagttatat tatttatgaa | 420 |
| cttttcaatg aaccagaaag tgcttcatgg tctgaaatca aaagttatag tgaatctctt | 480 |
| attaaaacaa tccgagctat tgatccagat aacttgattc ttgttccaac acccaattgg | 540 |
| gatcaatatg ttaaacaagc tgctgctgat ccaattacaa ttgacaataa cattgcttat | 600 |
| acaatccata tttatgttgg aacacatccc ttgtcttaca ttgatgatgc taaagaagca | 660 |
| cttaaaaaga ttcctctttt tggtactgaa attggtgcaa tgaatgcaga tggtgatgga | 720 |
| gctttggatc gtgcaaaatt cactcaatgg attaatttct atgaagaaaa taaaatttct | 780 |
| tatcttgcat gggcagttca atcaaaacaa gagtccgatt caattttgaa accatctgaa | 840 |
| aattggaatg atctaagtga atggggtact tgttcaagg aaacaattac tcgttatcag | 900 |
| taa | 903 |

<210> SEQ ID NO 20
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

| | |
|---|---|
| atgcttgtgc ttttacttct ccatttcata aactcaaaag cgcctccatt cggaagaccc | 60 |
| cgtgttgagg gaaacaagat cgtcggcaac aagcgagcac caggagtgct tcgcggagtt | 120 |
| ggtctttcgt ggcacaactg gtggccacaa ttctacaacg cagccacaat caaccacctc | 180 |
| aagaatgact tccatgccaa tgtcatccga gcagctattg gcgtcgagaa ggagaacggg | 240 |
| tattttgaca accagcagaa cgcgtacgac ttactttacg cagcagtgga tgcagcactc | 300 |
| tcagcaggaa tctacgtgat tgtcgactgg caagcattcc agattcatga atcagatgcg | 360 |
| aagcagttct tcacgacagt tgtcaacaag tacaagggta agtccaacgt catttacgag | 420 |
| atcttcaacg aaccagaaag cgcaggatgg tcagagatca aaagtattc tatcagcttg | 480 |
| atccaaacca tcagagccat cgattctaat gctttcatcc tcgtcccgac accaaactgg | 540 |
| gatcagtatg tcgagcaagc agcagcggat ccaataagcg agtactcaaa catcgcttac | 600 |
| acaatccaca tctacgcagc gactcaccca ttgtcgtacc tggacaacgc acgcacagcc | 660 |
| ctcaagacaa tcgcgctctt cgggacagaa atcggagcga tggaagcgag cggggatgga | 720 |
| gcaattgatc aaagcaagta ccaacaatgg atcgacttct atgagcaaaa cgggatttct | 780 |
| tatctctgct gggctgtcca atccaaggaa gaaactgact ccatcctgaa gccaagtgag | 840 |
| gactggaacg acttgacagc ttggggcaag ctttgcaagt ccaccatcac tgctcatcag | 900 |
| taa | 903 |

<210> SEQ ID NO 21
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atgcttgtgc ttttacttct ccatttcata aactcaaaag cacctccatt cggaagactc    60
tgtgttgagg gaaacaagat cgtcggcaac aagcgagcac caggagtgct tcgcggagtt   120
ggtctttcgt ggcacaactg gtggccacaa ttctacaacg cagccacaat caaccacctc   180
aagaatgact tccatgccaa tgtcatccga gcagctattg cgtcgagaa ggagaacggg    240 tattttgaca accagcagaa cgcatatgat ttactttacg cagcagtgga tgcagcactc   300
tcagcaggaa tctacgtgat tgtcgactgg caagcattcc agattcatga atcagatgcg   360
aagcagttct tcacgacagt tgtcaacaag tacaagggta agtccaacgt catttacgag   420
atcttcaacg aaccagaaag cgcaggatgt cagagatca aaaagtattc tatcagcttg    480
atccaaacca tcagagccat cgattctaat gctttcatcc tcgtcccaac accaaactgg   540
gatcagtatg tcgagcaagc agcagcggat ccaataagcg agtactcaaa catcgcttac   600
acaatccaca tctacgcagc cactcaccca ttgtcgtacc tggacaacgc acgcacagcc   660
ctcaagacaa tcgcactctt cgggacagaa atcggagcga tggaagcgag cggggatgga   720
gcaattgatc aaagcaagta ccaacaatgg atcgacttct atgagcaaaa cgggatttct   780
tatctctgct gggctgtcca atccaaggaa gaaactgact ccatcctgaa gccaagtgag   840
gactggaacg acttgacagc ttggggcaag ctttgcaagt ccaccatcac tgctcatcag   900
taa                                                                  903

<210> SEQ ID NO 22
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atgtttctcc ttctcccgct cgcgttctcc gccgtcccga ctttcggccg cctttccgtg    60
aagtccggga agctcacagg ctcctctggc gatcccgtta tccttcgagg cgtctcgctc   120
ggctgggata catggtgggg ccaattctac aatgaggaca cgatccagca tctgatcacc   180
gacttccacg cgaaccttat ccgggccgca atcggaatcg agcccactgg agcatatctc   240
cagaataagc aattggcgct taatcatctc gatgcggccg ttaaggcggc gatcaagctc   300
ggagtttaca tcatcatcga cttccacgcg caccagctgc acacgaatga tgcgaaggag   360
ttcttcacga ccgtcgtcaa caaatacaaa ggaagcgaat atgtgatcta cgaaatctgg   420
aacgaaccag aaagcgcgaa ctgggcgacg atcaagcaat acgcgaagga cgtgattccg   480
gttatccgga acgtggatcc agacgcagtg atcctcgttt cgaattccca gtgggatcag   540
caccccgacg aaccggccgc ggatccgctc ccattcacga atatcgcata cgtcgtgcat   600
ttctatgcag gaacacacgg atcgtggctg cgcgagcgcg tgacggcagc actcgcgaag   660
gggatcgcga tcttcgtgtc ggaatgcgga ggaatgaatt ctgacggaga tggacccgtg   720
tcgacaacgg aatggaacaa ttgggtggac ttgttggaga agaataagat tagttatgcg   780
gcgtggtgtg ttgaggcgaa ggtagaatct gcatcgattt tgaaggtgag tgcgaattgg   840
aatgatttga ctgattgggg caagacagtc aaacagacga tcacgtcgag acaatga      897

<210> SEQ ID NO 23
<211> LENGTH: 1143
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 23

```
atgctttctg tctctctgtt tctctccctt tccgtgagtg cgggcggctg gtactccacg      60
aaaggcaaca agatcgtcaa ctctgcaggc cagaccgtcc ggctgaccgg gctcaattgg     120
tttggcttcg agacgaataa tgagatcatc catggcctct gggctgcgaa tctggagagc     180
atggttgccg aatgcaaacg ccgcggcttc aacacctggc ggatccccat ttccgcgtcc     240
gttcttcagt catggaaagc tggcgttccg aagacgaaat gggacggtaa tcccagcgtc     300
aacccggacc tgaccggcct gtcaaactac gatgtgttca aaaagttcgt tgctgctgcg     360
agcaagaaca atcagaagat tttcctcgat cttcacagcg tcatcgatga cagttacatg     420
gacaaccttt ggtacaacgc ggcccatccg cccgagtata tcatttccgc attggagtgg     480
tttgcgacga cattccgaaa cgaggacacg attatcggca tcgacgtgaa gaacgaacct     540
cacgacgttg cgacaagagc gatgggacgt accgccatct gggataagtc gagcgcgcag     600
aacaactgga agtcgtttat cgaatccgcc gcgaagcgaa tcttggcggc gaatccaaac     660
ctgctgatca tggtcgaggg catcgagtgc ttcaacagcc cagataaggg cgcaatctgg     720
ggatggtggg gcggcaatct gtcccccgtg aactacgcag gactcggaat cgacctcggg     780
gcataccaga taagctggt ttacgcacca cacgaatacg gaccgtcggt ctcggatcag     840
gcctggttcc acgcgggatt cagttatgac accctgtatt ccgaacactg gagtaaccag     900
tggatgttta tttacgataa ggggatcgcc ccgttgctgt tcggtgagtg gggaggacac     960
gtccagggcg cgaatgccgt ctggatgaag gcgttcgtgc agctgattgg gaagtatgga    1020
ttctcgcaga cgttctggtg cttgaacccg aattctggcg atacaggtgg gttggttgga    1080
aatgattgga gacctgggga tgaggtgaaa tacaatatca tcaaaccgat tttggatctc    1140
taa                                                                  1143
```

<210> SEQ ID NO 24
<211> LENGTH: 921
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
atgcttggcc tcttgctgtc tttctccttc gcggaggcgg atccggactt agttcggctc      60
cacgttgatg gcaatcgggt tgtcattggc aagcctggcc ttgcatcatc caagactgcc     120
atgcttcgtg gagtttcatg ttcatggcat aactggtggc cccaattcca gtgctgcc      180
accgttgcg ggttgaagtc ggacttccac gccaacattg ttcgaacctt catcggtgtt     240
gaaaagatg gaggtttcct ccaaaaccaa caaaaggcct atgattgctg ctatgctgtc     300
gttgacgaat gtattgctca aggcatttat gtgatcatca actgggcgtc tttcgttcta     360
acttatcagt cgcaagcaac cacttctctt aagacagtcg ccaccaaata tcatagtagc     420
tcctatgtga tctatgaatt gctgaatgaa cctgaagctg ccacctgggc ccagattaag     480
ccgtattcac aggccttgat tcaaacaatc cgagcgattg acgcaagcaa ccttattttg     540
gtgccaactc cacgatggga tcaggaaatt ggagcggctg caaacgatcc gatcactggg     600
gacaacaatt tggcgtacac cctccatatc tacacgggaa ctcatccagc ttcttacagg     660
gatgacgcgc gggctgcgaa aaagaagatt ccggtttggg ctgacgaaaa tggagcaatg     720
aacgctgatg gaaagggcaa cctcgatcga actggctgga acacgtggat cgccttctat     780
```

```
gaggaactcc aaatcccatg gcttggctat ggaactcagg acacctctga aacttgctca    840
atctttaaat cgacggatag tttcaatgac ctcagcgatt ggggcaagct tcttaaggag    900
acaatccgca agtaccagta a                                              921
```

<210> SEQ ID NO 25
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
atgttcttcc tcttcctcac gtccggtctc tccggctggt attcgacgag cggcagcaag      60
atcgtcgaca gcacgggcaa aactgtccgc cttaccggtc tgaactggtt tggattcgag     120
acgacgaatg aagtcttcca tggccttltgg gcagcgaatc ttgaagacac gatgaccgaa    180
gttgcgaagc ggggcttcaa cacctatcgt gtcccggttt ctgccaccgt tcttgccgcc    240
tggaaggccg gacgccgaa taaggcctgg ggtaacaatc cgatggcgaa tccgaatctc     300
gaagggaaga gcaaccttga cgtctttgac accttccttg ctgagtgcaa gaaacacaac    360
cagaaggttt atatcgacgt ccatggcgtc actgatggta gctatatgga tcctcttltgg    420 tacacagctg cacatcctcc tgaatttatc atcacgggac ttgaatggtt tgcagatcga    480
tacaaaaatg acgacacggt catcggaatc gatatcaaga atgaaccgca tggcagatgc    540
gagcaaaccg aagccgcaaa gtgggacaac acgcaaaatc agaacaactg gaagcatttc    600
atcgaaaccg cagccgcgag aattttltgctt aaaaattcga aattgctgat ctcgtcgaa    660 gggattgaat gctataacaa tatttlggga tggtgggtg gaaacttlggt cccagcgaag     720 gagttgccaa tcaacttggg aagttaccag aagcaattgg tttatgcccc acacgaatac    780
ggaccgtcgg tttcgaccca gaaatggttt tatagtgggt taactatga actttltgtac      840 aaagatcact ggaaagatca atggatgtat ttgattgagg gaaatacggc accaatttgc    900
ataggagaat ggggtggaca tgtgcaagga gataatgctg tctggatgaa agcagtcgta    960
caattgattg gaaaatatgg attgagtcag acgttlttgtg gcttgaaccc gaactctga    1020 gacaccggag gctgttlggg atatgattlgg aagacttlggg atgaggagaa gtatgcaatc    1080
ctgaagccaa ttttlggcact ctaa                                         1104
```

<210> SEQ ID NO 26
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atgttcttcc tcttcctcac gtccggtctc tccggctggt attcgacgag cggcagcaag     60
atcgtcgaca gcacgggcaa aactgtccgc cttaccggtc tgaactggtt tgggttcgag    120
acgacgaatg aagtcttcca tggccttltgg gcagcgaatc tcgaagacac gatgaccgaa   180
gttgcgaagc ggggcttcaa cacctatcgt gtcccggttt ctgccaccgt tcttgccgcc   240
tggaaggccg gacgccgaa taaggcctgg ggtaacaatc cgatggcgaa tccgaatctc    300
gaagggaaga gcaaccttga cgtctttgac accttccttg ctgagtgcaa gaaacacaac   360
cagaaggttt atatcgacgt ccacggcgtc actgatggta gctatatgga tcctcttltgg    420
```

| | |
|---|---|
| tacacagctg cacatcctcc tgaatttatc atcacgggac ttgaatggtt tgcagatcga | 480 |
| tacaaaaatg acgacacggt catcggaatc gatatcaaga atgaaccgca tggcagatgc | 540 |
| gagcaaaccg aagccgcaaa gtgggacaac acgcaaaatc agaacaactg aagcatttc | 600 |
| atcgaaaccg cagccgcgag aattttgctc aaaaattcga aattgctgat tctcgtcgaa | 660 |
| gggattgaat gctataacaa tatttgggga tggtggggtg aaacttggt cccagcgaag | 720 |
| gagttgccaa tcaacttggg aagttaccag aagcaattgg tttatgcccc tcacgaatac | 780 |
| ggaccgtcgg tttcgaccca gaaatggttt tatagtgggt ttaactatga tactttgtac | 840 |
| aaagatcact ggaaagatca atggatgtat ttgattgagg gaaatacggc accaatttgc | 900 |
| atcggagaat ggggtggaca tgtgcaagga gataatgctg tctggatgaa agcagtcgta | 960 |
| caattgattg gaaaatatgg attgagtcag acgttttggt gcttgaaccc gaactctgga | 1020 |
| gacaccggag ggctgttggg atatgattgg aagacttggg atgaggagaa gtatgcaatc | 1080 |
| ctgaagccaa ttttggcact ctaa | 1104 |

<210> SEQ ID NO 27
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

| | |
|---|---|
| atgcttgcgc tcttcgccgc gctgagcctt tccgaccacc gcctgcgtgt tgtcggcact | 60 |
| gacattgtga ctggctacgt tggctcgacc gcgacggccc gcgtccgggg cgtctcctgt | 120 |
| tcatggcaca actggtggcc tcagttccac accgcgagcc ccgtcgatgg cctcaagacg | 180 |
| cagttccatg cgaacgtcgt ccgcacgttc attggtgttg agaaagagaa cggctacttg | 240 |
| acgaacaagc agaaggcgat ggactgctgc tatgcggtca tcgacgagtg cattaagcag | 300 |
| aatatctacg gcattgccaa cttcgctgct ttccagctcc acctgaagga ggcgaccgat | 360 |
| ttcttcaccg ctgttgccgg gaagtacaag aacagcgagt acatcatcta cgagctgatg | 420 |
| aacgagcccg agagcgcgcc atggtcccag atcaagtcat actcccagtc cctgatcaag | 480 |
| aggatccgcg ccatcgaccc caagaacctc atcctcgtcc cgaccccgca gtgggaccag | 540 |
| aaggtcctcg acgcggccaa tgacccgatc accggcgtgg ataacatcgc atacactctc | 600 |
| catatctaca ctgcgaccca tccgaagtca ttccaggacg cacccgcca gcgaagaag | 660 |
| aagatcgcca tctgggcgga cgagaacggc gctatgaact ccgacggcaa aggccctctc | 720 |
| gaccgcaccg gctggaacag ctggatcagc ttctatgagg agctgggcat cccgtggctc | 780 |
| gggtacggca cccaggacac ctcggagacc tgctccatct tcaagaagac cgatagcttc | 840 |
| agtgatctct ccgagtgggg aacgctgctt aagcagacca tcctgaagta ccagtaa | 897 |

<210> SEQ ID NO 28
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

| | |
|---|---|
| atgtttctcc ttctcccgct cgcgttctcc gccgtcccga ctttcggccg cctttccgtg | 60 |
| aagtccggga agctcacagg ctcctctggc gatcccgtta tccttcgagg cgtctcgctc | 120 |

```
ggctgggata catggtgggg ccaattctac aatgaggaca cgatccagca tctgatcacc    180
gacttccacg cgaaccttat ccgggccgca atcggaatcg agcccactgg agcatatctc    240
cagaataagc aattggcgct taatcatctc gatgcggccg ttaaggcggc gatcaagctc    300
ggagtttaca tcatcatcga cttccacgcg caccagctgc acacgaatga tgcgaaggag    360
ttcttcacga ccgtcgtcaa caaatacaaa ggaagcgaat atgtgatcta cgaaatctgg    420
aacgaaccag aaagcgcgaa ctgggcgacg atcaagcaat acgcgaagga cgtgattccg    480
gttatccgga acgtggatcc agacgcagtg atcctcgttt cgaattccca gtgggatcag    540
caccccgacg gaccggccgc ggatccgctc ccattcacga atatcgcata cgtcgtgcat    600
ttctatgcag gaacacacgg atcgtggctg cgcgagcgcg tgacggcagc actcgcgaag    660
gggatcgcga tcttcgtgtc ggaatgcgga ggaatgaatt ctgacggaga tggacccgtg    720
tcgacaacgg aatggaacaa ttgggtggac ttgttggaga agaataagat tagttatgcg    780
gcgtggtgtg ttgaggcgaa ggcagaatct gcatcgattt tgaaggtgag tgcgaattgg    840
aatgatttga ctgattgggg caagacagtc aaacagacga tcacgtcgag acaatga       897

<210> SEQ ID NO 29
<211> LENGTH: 921
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atgcttggcc tcttgctgtc tttctccttc gcggaggcgg atccggactt agttcggctc     60
cacgttgatg gcaatcgggt tgtcattggc aagcctggcc ttgcatcatc caagactgcc    120
atgcttcgtg gagtttcatg ttcatggcat aactggtggc cccaattcca cagtgctgcc    180
accgttgcgc ggttgaagtc ggacttccac gccaacattg ttcgaacctt catcggtgtt    240
gaaaaagatg gaggtttcct ccaaaaccaa caaaaggcct atgattgctg ctatgctgtc    300
gttgacgaat gtattgctca aggcatttat gtgatcatca actgggcgtc tttcgttctc    360
acttatcagt cgcaagcaac cactttcttt aagacagtcg ccaccaaata tcatagtagc    420
tcctatgtga tctatgaatt gctgaatgaa cctgaagctg ccacctgggc ccagattaag    480
ccgtattcac aggccttgat tcaaacaatc cgagcgattg acgcaagcaa ccttattttg    540
gtgccaactc cacgatggga tcaggaaatt ggagcggctg caaacgatcc gatcactggg    600
gacaacaatt tggcgtacac cctccatatc tacacgggaa ctcatccagc ttcttacagg    660
gatgacgcgc gggctgcgaa aaagaagatt ccggtttggg ctgacgaaaa tggagcaatg    720
aacgctgatg gaaagggcaa cctcgatcga actggctgga acacgtggat cgccttctat    780
gaggaactcc aaatcccatg gcttggctat ggaactcagg acacctctga aacttgctca    840
atctttaaat cgacggatag tttcaatgac ctcagcgatt ggggcaagct tcttaaggag    900
acaatccgca agtaccagta a                                              921

<210> SEQ ID NO 30
<211> LENGTH: 921
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
```

```
atgcttggcc tcttgctgtc tttctccttc gcggaggcgg atccggactt agttcggctc    60
cacgttgatg gcaatcgggt tgtcattggc aagcctggcc ttgcatcatc caagactgcc   120
atgcttcgtg gagtttcatg ttcatggcat aactggtggc cccaattcca cagtgctgcc   180
accgttcgcg ggttgaagtc ggacttccac gccaacattg ttcgaacctt catcggtgtt   240
gaaaaagatg gaggtttcct ccaaaaccaa caaaaggcct atgattgctg ctacgctgtc   300
gttgacgaat gtattgctca aggcatttat gtgatcatca actgggcgtc tttcgttctc   360
acttatcagt cgcaagcaac cactttcttt aagacagtcg ccaccaaata tcatagtagc   420
tcctatgtga tctatgaatt gctgaatgaa cctgaagctg ccacctgggc ccagattaag   480
ccgtattcac aggccttgat tcaaacaatc cgagcgattg acgcaagcaa ccttattttg   540
gtgccaactc cacgatggga tcaggaaatt ggagcggctg caaacgatcc gatcactggg   600
gacaacaatt tggcgtacac cctccatatc tacacgggaa ctcatccagc ttcttacagg   660
gatgacgcgc gggctgcgaa aaagaagatt ccggtttggg ctgacgaaaa tggagcaatg   720
aacgctgatg gaaagggcaa cctcgatcga actggctgga acacgtggat cgccttctat   780
gaggaactcc aaatcccatg gcttggctat ggaactcagg acacctctga aacttgctca   840
atctttaaat cgacggatag tttcaatgac ctcagcgatt ggggcaagct tcttaaggag   900
acaaaccgca agtaccagta a                                             921

<210> SEQ ID NO 31
<211> LENGTH: 921
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atgcttggcc tcttgctgtc tttctccttc gcggaggcgg atccggactt agttcggctc    60
cacgttgatg gcaatcgggt tgtcattggc aagcctggcc ttgcatcatc caagactgcc   120
atgcttcgtg gagtttcatg ttcatggcat aactggtggc cccaattcca cagtgctgcc   180
accgttcgcg ggttgaagtc ggacttccac gccaacattg ttcgaacctt catcggtgtt   240
gaaaaagatg gaggtttcct ccaaaaccaa caaaaggcct atgattgctg ctatgctgtc   300
gttgacgaat gtattgctca aggcatttat gtgatcatca actgggcgtc tttcgttctc   360
acttatcagt cgcaagcaac cactttcttt aagacagtcg ccaccaaata tcatagtagc   420
tcctatgtga tctatgaatt gctgaatgaa cctgaagctg ccacctgggc ccagattaag   480
ccgtattcac aggccttgat tcaaacaatc cgagcgattg acgcaagcaa ccttattttg   540
gtgccaactc cacgatggga tcaggaaatt ggagcggctg caaacgatcc gatcactggg   600
gacaacaatt tggcgtacac cctccatatc tacacgggaa ctcatccagc ttcttacagg   660
gatgacgcgc gggctgcgaa aaagaagatt ccggtttggg ctgacgaaaa tggagcaatg   720
aacgctgatg gaaagggcaa cctcgatcga actggctgga acacgtggat cgccttctat   780
gaggaactcc aaatcccatg gcttggctat ggaactcagg acacctctga aacttgctca   840
atctttaaat cgacggatag tttcaatgac ctcagcgatt ggggcaagct tcttaaggag   900
acaatccgca agtaccagta a                                             921

<210> SEQ ID NO 32
<211> LENGTH: 1104
<212> TYPE: DNA
```

<213> ORGANISM: Artificial Sequence
<220> FEATURE:
<223> OTHER INFORMATION: Description of Artificial Sequence: Synthetic
    polynucleotide

<400> SEQUENCE: 32

```
atgttcttcc tcttcctcac gtccggtctc tccggctggt attcgacgag cggcagcaag    60
atcgtcgaca gcacgggcaa aactgtccgc cttaccggtc tgaactggtt tgggttcgag   120
acgacgaatg aagtcttcca tggcctttgg gcagcgaatc tcgaagacac gatgaccgaa   180
gttgcgaagc ggggcttcaa cacctatcgt gtcccggttt ctgccaccgt tcttgccgcc   240
tggaaggccg ggacgccgaa taaggcctgg ggtaacaatc cgatggcgaa tccgaatctc   300
gaagggaaga gcaaccttga cgtctttgac accttccttg ctgagtgcaa gaaacacaac   360
cagaaggttt atatcgacgt ccacggcgtc actgatggta gctatatgga tcctctttgg   420
tacacagctg cacatcctcc tgaatttatc atcacgggac ttgaatggtt tgcagatcga   480
tacaaaaatg acgacggt catcggaatc gatatcaaga atgaaccgca tggcagatgc   540
gagcaaaccg aagccgcaaa gtgggacaac acgcaaaatc agaacaactg gaagcatttc   600
atcgaaaccg cagccgcgag aattttgctc aaaaattcga aattgctgat tctcgtcgaa   660
gggattgaat gctataacaa tatttgggga aggtggggtg gaaacttggt cccagcgaag   720
gagttgccaa tcaacttggg aagttaccag aagcaattgg tttatgcccc tcacgaatac   780
ggaccgtcgg tttcgaccca gaaatggttt tatagtgggt ttaactatga tactttgtac   840
aaagatcact ggaaagatca atggatgtat ttgattgagg gaaatacggc accaatttgc   900
atcggagaat ggggtggacc tgtgcaagga gataatgctg tctggatgaa agcagtcgta   960
caattgattg aaaatatgg attgagtcag acgttttggt gcttgaaccc gaactctgga  1020
gacaccggag ggctgttggg atatgattgg aagacttggg atgaggagaa gtatgcaatc  1080
ctgaagccaa ttttggcact ctaa                                         1104
```

<210> SEQ ID NO 33
<211> LENGTH: 1104
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 33

```
atgttcttcc tcttcctcac gtccggtctc tccggctggt attcgacgag cggcagcaag    60
atcgtcgaca gcacgggcaa aactgtccgc cttaccggtc tgaactggtt tgggttcgag   120
acgacgaatg aagtcttcca tggcctttgg gcagcgaatc tcgaagacac gatgaccgaa   180
gttgcgaagc ggggcttcaa cacctatcgt gtcccggttt ctgccaccgt tcttgccgcc   240
tggaaggccg ggacgccgaa taaggcctgg ggtaacaatc cgatggcgaa tccgaatctc   300
gaagggaaga gcaaccttga cgtctttgac accttccttg ctgagtgcaa gaaacacaac   360
cagaaggttt atatcgacgt ccacggcgtc actgatggta gctatatgga tcctctttgg   420
tacacagctg cacatcctcc tgaatttatc atcacgggac ttgaatggtt tgcagatcga   480
tacaaaaatg acgacggt catcggaatc gatatcaaga atgaaccgca tggcagatgc   540
gagcaaaccg aagccgcaaa gtgggacaac acgcaaaatc agaacaactg gaagcatttc   600
atcgaaaccg cagccgcgag aattttgctc aaaaattcga aattgctgat tctcgtcgaa   660
gggattgaat gctataacaa tatttgggga tggtggggtg gaaacttggt cccagcgaag   720
```

```
gagttgccaa tcaacttggg aagttaccag aagcaattgg tttatgcccc tcacgaatac    780
ggaccgtcgg tttcgaccca gaaatggttt tatagtgggt ttaactatga tactttgtac    840
aaagatcact ggaaagatca atggatgtat ttgattgagg gaaatacggc accaatttgc    900
atcggagaat ggggtggaca tgtgcaagga gataatgctg tctggatgaa agcagtcgta    960
caattgattg gaaagtatgg attgagtcag acgttttggt gcttgaaccc gaactctgga   1020
gacaccggag ggctgttggg atatgattgg aagacttggg atgaggagaa gtatgcaatc   1080
ctgaagccaa ttttggcact ctaa                                          1104

<210> SEQ ID NO 34
<211> LENGTH: 921
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atgcttggcc tcctgctttc gccctccctc tcggaggcgg atccggactt ggttcggctc     60
cacgtcgacg gcaaccgcat tgtcatgggc aagccgggcc ttgcgtcgtc gaagacggcg    120
atgcttcgcg gcgtttcgtg ctcgtggcac aactggtggc cgcagttcca cagcgccgcg    180
acggtgcgcg ggctgaagtc cgacttccac gcgaatgtcg tccgtacgtt catcggcgtc    240
gagaaggagg gcggcttcct cacgaaccag cagaaggcgt atgactgctg ctatgcggtt    300
gtcgacgagt gcattgcgca gggcatctac gtcatcatca actgggcatc gttcgtgctg    360
acatatcaga cgcaggcgac ccaattcttc aagacagtcg gaccaaaata ccacagcagc    420
tcatacgtca tctacgagct gctcaacgag cccgaggcgg cgacatgggc ccagattaag    480
ccatattcgc aggccctcat ccagacgatc cgcgcaatcg acccgagcaa cctcattctg    540
gtgccgacgc cccgatggga ccaggaaatc ggggcggccg ccaacgatcc gatcacaggc    600
gataacaact tggcatacac cctccacatc tacacgggaa cccatccggc ctcataccgc    660
gacgacgcgc gcgccgcaaa gaagaagatc cctgtgtggg cggacgagaa cggcgcaatg    720
aacgctgatg gaaagggcgc tctcgaccgg acgggctgga cacttggat cgccttctat    780 gaggagctcc agatcccgtg gcttggctat ggaactcagg acacctccga aacttgctcg    840
atctttaagt cgacggatag cttcaacgat ctcagtgact ggggcaagct cctgaaggag    900
accatccgca agtaccagta a                                              921

<210> SEQ ID NO 35
<211> LENGTH: 849
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atgtttgctc tttttgctgc attgactttt gcatccacga agactgacaa gtgtcgaggt     60
gtctcatgtt catggcataa ttggtggcct caattccaca ctgcaaagac agtggatggt    120
ttgattagtg attttcatgc aaatgttgtt aggacattca ttggtgttga aaagaaaag    180 ggatatttga cgaataagca gaatgcattg acatgttgtt acaatgtgat tgacgaatgc    240
atttcgaaag gaatctttgg tatcattaat tgggcttcat ttcaaaactac ttatcttact    300 caagcaactg aattctttac gaccatggca aagaaatatg cggggaacgc aaaagttatt    360
```

```
tatgagcttt tgaatgagcc agagagtgct acttgggcac aaatcaaaac gtattcagaa      420
agtttaatca aaactattcg tcaatatgac aagactaatt tgattttagt tcctactcca      480
tcatgggatc agaagattgg agaagcagca aaagatccag ttacgattga taccaatctt      540
gcttatacat tccatattta cactgcaact catccgaagt cgtatcaaga tgatcttaag      600
gctgccgttg gtaagatctc cgtttgggca gatgagaatg gtgcaatgaa ttctgatgga      660
aagggtgcgc ttgatactgc tggttggaac aactggatca gtttatatga gcagcttgga      720
gtcaattggt tgtgctacgg aacccaagat acatcggaga cttgttcatt gttcaagtca      780
actgatagct tcagcgatct ttctgcttgg ggtactcttt gcaagtcgac tatcaggaag      840
taccagtaa                                                              849
```

```
<210> SEQ ID NO 36
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atgtgcttcc tcattcttgt cttggatttg gttcgggccg aatggttttc taccaagggt       60
aacaagatta taaatgaaac tggtggagct gttcgcttaa ctggtatcaa ttggttcggt      120
ttcgaaacta cggaagaagt ttttcatggg cttgcggcaa acagtcttca aaacctcatc      180
aaaatggttg ctgatcataa attcaattgt tggcgatgtc cagtctctgc ctctgttatt      240
cacgattgga tgattggaaa tccccgtaag gatcttaaag tcaattatac atataaccca      300
agtttaagag gttgtctaa ttttgatatt tttaagatat tcatcaaaga agtgaagaaa       360
tatggacatc gtgtgttcat tgatattcat agtattgttg ataattctta tcgagacaac      420 cttggtgga atgcagaaca tcctccagaa tacatttat ccgctcttga atggatcgcc        480
gattatttta aagatgaacc tgcgttcatt ggaattgatg ttaaaaatga gccacatggt      540
acatgcgatg atccgactgc agctcattgg gatggtacaa agaatgacaa caattggaag      600
tattttgttg aaactgcggc tgctcgaatt catgcgaaaa atccaaaatt attgattttt      660
gttgaaggta ttgagtgtta taaaggtgtt gaaggatggt ggggtggtca acttgcagcg      720
gtcaaggatt atccaattaa acttggcact tatcaaaaca agcttgttta cagtccacat      780
gattatggtc cttcagtgaa tcctaagcaa acttggcttc gtgataacat gacctatgat      840
tcgttgatgg cggaggtatg ggaaccccag tggttattca ttcatgaaaa ttcaattgcg      900
ccaatattca ttggtgaatg gggtggacat cttgagaaac ggataacttt atggatgggt      960
ccatttgtac aacttattgc caaatacaaa ctgagcttta ctcattggtg tctaaacccg     1020
gattctggtg ataccggagg cttgcttttg cccgattggc aaacttggaa cgaagagaaa     1080
tacaacttca tcaagcctgt tttcgactaa                                      1110
```

```
<210> SEQ ID NO 37
<211> LENGTH: 1119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
atgcttgttc ttcttgcctc ttttggtgtt gcgtattaca ttagcgcgag tggcaatgag       60
```

```
cttgtggatc cgactggtaa gcaattgcgt atcactggca ttaattggtt tggtttcgag      120
acttctcaga gtgcatttca cggtctttgg aatgctaatt tgcacaaagt tgttcagcaa      180
gttgctgaac atgggttcaa ttgttttcga tgcccaattt catgtgacct tatccacaag      240
tggatgcgtg gtgataagac tccgctccag tggattaata ctgaacctga tgctaatcct      300
gatatgaaag gtatcagtag ccgtggaatt tgggatatgt ttatggctga ttgcaagaaa      360
gctggaatta aggttttcat tgacatccac ggaattcaac ctgatagcta tacgcttccg      420
ctctggggcg atacagaata cctcatttca gctcttgaat ggttcgctaa tgaattcaag      480
aacgatgata ctttcattgc aattgatgtc aaaaatgaac ctcatcaaca aggtcaggga      540
tgtggtactg gtgccaatga tgcagtttgg gagtcaagca cgagatcaaa caattggcca      600
tacgtcgctg ggctggcggg aaagcgaatt cttgcaaaga atccgggtct gttaatcctt      660
gttgaaggca atcaatgtta caagggtgat agttcatggt ggggtggcaa tcttgcgggt      720
gttaaagaca ttcctgtcga tgttggaaac cccaagaaat tagtttattc accacatgaa      780
tatggaccgt cagtgaatga tcaggcatgg ttccatccta cgataaatta cgatcagttg      840
tatagtcagc attggcacaa gcattggtta tatattcatg aggaaggcat tgctcctctc      900
cttattggtg aatggggtgg caagttatcc ggaacaaaca ctcaatggat gaagctgttc      960
gttaatttga ttgctcaata tggttttaagt catactttct ggtgtttgaa cccaaactca     1020
ggtgacacag gtggacttct caaggataac tggaaagact gggatgaaga gaaatatgcc     1080
ttcatcaagc cttgcctcgg aggctcttta tttaagtga                            1119
```

<210> SEQ ID NO 38
<211> LENGTH: 906
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
atgttgtttc ttctcctctt gttaagtttg gctttcagtg ttccacctct atatggtcgg       60
cttcaagtca ttaataataa gctttgcgat gcgagtggaa atccaattat tcttcgggga      120
gttggctttg catggcataa ttggtggcca gagttttaca cctcagcgaa ggttggagaa      180
atcaagactg ttttcatgc aaacgttgtt cgagcagcaa ttgcgtatga taggaaggt      240 ggtttacaaa gtaacccaac aagggcttat gatttgttgt atgcagttat tgatggtgct      300
attgcgcaag gaatttatgt gattgtcgat tggcaagtgt ttcaaatttt tgaatcagca      360
gcggttgatt tctttaccaa ggttgcaacc aagtataaag gcgttccaaa tattctttat      420
gaaattttga atgaaccgga gtcagatggg tggccagcta ttaaaagata tgctcttacc      480
gtcatcaaag ttattcgagc aatcgatcct gaaaatcctg ttatcatcgt tgggacacca      540
agttgggacc aatatattga gcaagctgct gcggatccaa ttacagaata taagaatatt      600
ctttacagtc ttcatattta tgttggaact catccagact cataccgtac aaatgctcga      660
aattcgttaa gtaagattgg aattttttgct actgagatgg gtgcaatgaa cgctgatgga      720
gatggacctt tgaatcgaga aaagttcaat cagtggattt cgttttatga agaagttgga      780
atttcttatc ttgcttgggc acttcaaact ggttcaattt cctgtggtct tactaattct      840
gttacaatca gcgatttgac agaatggggt aaactcttcc gagataccat ttataataag      900
cagtaa                                                                906
```

<210> SEQ ID NO 39
<211> LENGTH: 903
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

| | | | | | |
|---|---|---|---|---|---|
| atgttgcttc | tttctcttct | tttgagttttt | gcactgagtg | ttgcacctcc | ttatggtctg | 60 |
| cttcaggtcg | ttgataataa | agtgagtgat | tcaagaggaa | atccgataat | ccttcgagga | 120 |
| gttggttttg | cgtggcataa | ttggtggcca | gaattttata | catcagcgaa | ggttggagaa | 180 |
| atcaagacag | ttttttaatgc | aaatgttgtt | cgagcagcga | ttgcatatga | taaagatggt | 240 |
| ggccttcaga | gtaatccaac | aaaagcttat | gatttgcttt | atgcagtgat | tgacggtgct | 300 |
| gttgcacaag | gaatttatgt | tattgttgat | tggcaagtat | ttcaaatttt | tgaatctcaa | 360 |
| gctaaagatt | tctttacgaa | agttgtgact | aaatataaag | gtgttccaaa | tgtcatttat | 420 |
| gaaattttga | cgaaccggaa | atctgatgga | tgggcagcta | ttaaaagata | ttctatttct | 480 |
| cttcttggaa | ctatcagagg | aattgatcca | ggtgcatttg | ttttgattcc | aacaccaaac | 540 |
| tgggaccaat | atattgaaca | agcagcagca | gatccaatta | ccgaatataa | gaacattgct | 600 |
| tatactcttc | atatctatgt | cggaactcac | cctgattcgt | atcttacgaa | cgctcgaaac | 660 |
| gcactgagta | agatagccat | tttttgggact | gagattggtg | caatgaatgc | ggatggagat | 720 |
| ggaccttttga | atatcgagaa | attcaatcgt | tggatttcgt | tttatgaaga | agttaaaatc | 780 |
| tcttatcttg | catgggctct | tcaaacaggt | tctctttcgt | gtggtctcac | caattctgtt | 840 |
| acgatcagtg | atttgactgc | atggggtaaa | cttttcaagg | acaccatttt | caacaagcag | 900 |
| taa | | | | | | 903 |

<210> SEQ ID NO 40
<211> LENGTH: 924
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

| | | | | | |
|---|---|---|---|---|---|
| atgttggtga | ttcttctttc | tttggctatt | caggttccag | tcgatgttta | tggcaaactg | 60 |
| aaagtgagtg | gaaataagat | agttggctct | aatggtgctc | cagctgtctt | gcatggtgtt | 120 |
| tctttagcgt | ggcacaattg | gtggagtcag | ttctatactg | cgagcaatgt | tgcttatctg | 180 |
| gcgagtgagt | ggaaggtttc | gcttcttcgt | gctgcaattg | gagttgaacc | tgagggagct | 240 |
| taccttgatg | acccccgatct | cggagataag | tctgcaacga | ctgtggctga | tgctgctatt | 300 |
| aaggcaggaa | tttatgttat | tcttgatttt | catcagcata | aaattaacca | agatgctgct | 360 |
| gttaaatttt | tcacaaagtt | tgctcaaaag | tatagtggag | ttcccaatgt | catttatgag | 420 |
| ctttttaacg | agccagaatc | tgcaacttgg | cctgaagtca | aagcttatgc | agaagttgtt | 480 |
| attaaagtga | ttcacagttt | tgatcctgat | gctttgattc | ttgtcggttg | tcctcaatgg | 540 |
| gaccaaaaga | ttgaggaacc | tgctgatagt | ccaattactg | ggtacagcaa | cattgcttat | 600 |
| actcttcatt | tttatgctgg | cactcatacc | cagtggcttc | gtgattcagg | tcataatgcg | 660 |
| atcaataagg | gaatcgctgt | ctttgcatct | gagattggtg | gaatggatgc | tagcggagat | 720 |
| ggtcctattg | caacgagtga | atggaacttg | tggatttcat | ggttgaaagc | tcatgatatt | 780 |
| tcttgggctg | catggtcgat | tagtaataag | caagagacgt | gttcaatggt | tcttccaaca | 840 | tcgtcagcca attctccttg gggagataat caacttaatg aatggggtcg acttgttcga   900 gatcttttga tttcaatagc ctaa   924

<210> SEQ ID NO 41
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgttacttc tctctcttct gctgagtctt gcactgagtg ctgcacctcc atttggtctg    60
cttcaagtaa ctaataataa ggtcagtgat tctagtggga aacctgtgat tcttcgaggg   120
gttggttttg cgtggcataa ttggtggcca gagttttata cgtctgctaa ggttggggaa   180
attaaaactg tctttcatgc caatgttgtt cgagcagcaa ttgcttatga taaagaaggt   240
ggattgcaaa gcaatccaga caaagcttat caattgttgt atgccgtgat tgatggttcc   300
attgaacgag gaatttatgt gattgttgac tggcaagtat ttcgaatttt tgagtcagaa   360
gcaaaagatt tcttcactag agttgtaacg aaatataagg gtgttccaaa tgtgatttat   420
gaaattttga tgaaccaga atcagatgga tgggccgcta ttaaaaagta ttcgatttcc   480
cttcttggaa ctattagagc aatagatcct aatgcatttg ttttgattcc aactccgaac   540
tgggatcaat tgattgaaca agcagcagct gatccgatta cggaatataa gaacattgct   600
tatactcttc atatttatgt tgggactcat ccagactcgt atcttacaaa tgcgagaaat   660
gcattgagca agatagcgat ttttgccact gagattggag caatgaacgc tgatggtgat   720
ggaccattga atcttgagaa attcaatcgt tggattgcat tttatgagga agttggaatt   780
tcttatcttg cgtgggctct ccaaacaggc tctctttcat gtggtcttac taattcggtt   840
acgatcagtg atttaactga atgggcaaa cttttccgtg ataccattta caataagcag   900
tag   903

<210> SEQ ID NO 42
<211> LENGTH: 915
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atgcttgcag ttttcctgtc tttcagtctt tcagcagtcg tacaattgag tgttaaaggt    60
aacaaaattg ttggaccaac tggtactcca gttgtcagtc atggtgtttc attattttgg   120
cataactggg caggaattcc ttacaccgct gcaacagtta caagtgctgc ttcatgctta   180
ggtgccaaag ttattcgagc tgctattggt gtcgaaccag atggagatgg aattgctgct   240
caagcaggtt accttaccaa cccacaattg gctttgactt caacttatgc cgttgttgat   300
ggtgcagttg cagaaggtat ttatgttatc attgactggc atcagcatca atcaatttg    360 aatgcagcca agaatactt caccacagtt gccagaaat acaccggtgt tcccaatgtt   420
atttatgaag tttataatga accagctggt ccttcatggc agaagttaa agcttatgct   480 atcgaagtca tcaaagtcat cagacaatat gataccgata tgttatcct tgttggaact   540 ccccagtggg atcagaaacc agatgaagct gccaacagtc caatcactgg ttatgataac   600
attgcttaca cccttcattt ttatgctggt tcccacggac aatggttgag agatgctggt   660

| | |
|---|---:|
| gataaactcc tcagtgctgg atatccaatt tatgtttctg aatgcggtgg aatgaatgct | 720 |
| gatggtgacg gtggagttaa tactgctgag tggaataatt gggtttcatg gatggccaag | 780 |
| aatgatattt catgggctac atggtcactc aacaacaagg ctgaatctgc atctttgatc | 840 |
| actgcgaaca accgtgatat ctgcagcgcc aatgctttga ctgaatgggg tcgaatcgtt | 900 |
| aaggcagcca tctaa | 915 |

<210> SEQ ID NO 43
<211> LENGTH: 1095
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

| | |
|---|---:|
| atgttgctct tcctgctttc gagaatttca gtttcttggc tttcgacgag tggaagtaag | 60 |
| attactgatg gtggtcaaac agtgcgattg actggagtaa actggtttgg gtatgagacg | 120 |
| agcgaagaag tttttcatgg actttgggca gcaggacttc atgaccttgt tcagggagtt | 180 |
| tcacagaaaa agtttaacac atttcgagtt cctatttcag cgtcagttct gcaggattgg | 240 |
| aaagcaggta agccgaaccc gaaaccgaat attaatctta atgtgaatgc agatcttgaa | 300 |
| ggacttaata accagcaaat attcgatctt ttccttgcag attgtaagaa gtacaagatt | 360 |
| tatgttttta ttgatgttca cggagtgaca gatggatcat atatgacaa tctttggtac | 420 |
| acatcagctc atccagcaga atggatttat tcagctcttg agtggtttgc cgatcactac | 480 |
| aaaggagatc aaactatcat tggaattgat atcaagaatg agcctcatgg acgttgtgag | 540 |
| caggcggaag ccgcgaagtg gagtgattct aaagataaca acaattggaa gtatttcatc | 600 |
| gagacagcag ccgcacgaat ttgggtaag aatccaaatc tttttgatttt ggttgaagga | 660 |
| attgaatgct acaacaataa ttggggctgg tggggtggta acctcattcc agttaatgac | 720 |
| tatccaatta acttgggttc tgggcaaaag cagcttgttt atagtcctca tgagtatgga | 780 |
| ccttcagtta atgaccagtc atggttcaag agtggcttta attatgatag tctttacgca | 840 |
| gaccactggc agaagatgtg atgttcatc attgaaaaga atattgcccc aattttgatt | 900 |
| ggagaatggg gtggtcatgt tgttgagcct aatacgacat ggatgaaagc gcttgttcaa | 960 |
| cttatttcta aatatggctt gagccaaacg ttttggtgct tgaacccaga ttctggagat | 1020 |
| acgggtggac ttcttgagaa tgattggatt acctgggata ctgccaaact tgatatcatc | 1080 |
| aaaggagttc tttaa | 1095 |

<210> SEQ ID NO 44
<211> LENGTH: 1326
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

| | |
|---|---:|
| atgctgactt tggtgtattt cttgctttcg ttggttgtgt cgcttgagat tggaacgcag | 60 |
| cagtcagaag accatcccaa attgacgtgg cagaatgggt caagctcagt gtcagggtcg | 120 |
| attgtgcttg attcgaactg gagatggggtt catgacagtg ggacgacgaa ctgctatgac | 180 |
| ggaaacttgt ggagcaagga tctttgcccg agctcaaaca catgctctca gaaatgttac | 240 |
| attgaaggag cagattattc ggggacttat ggaattcagt cgagcggttc aaaactgacg | 300 |

```
ctgaagtttg tgacgaaagg atcgtattcg acaaacattg gaagccgcgt ttacctgttg      360
aaagatgaaa acacatatga atcgttcaaa ttgaagaaca aggaattcac gttcacagtg      420
gatgattcga agctgaactg tggattgaat ggtgcattgt attttgttgc gatggatgca      480
gatggtggga aagcgaaata ttcgagcttc aaacccgggg cgaaatatgg gatgggatat      540
tgtgatgcgc agtgcccgca tgacatgaaa ttcatcagtg ggaaagcgaa tgttgatgac      600
tggaagccac aggacaacga tgagaattca ggaaacggga acttggaac atgctgctcg       660 gaaatggata tctgggaagg aaacatgaaa tcgcaggcat acacggtaca cgcttgcacg      720
aagagtggac aatacgagtg cactggacag caatgcggag acacagattc tggtgacagg      780
ttcaagggaa cttgcgacaa ggatgggtgt gattatgcgt catggagatg gggagaccaa      840
agtttctatg ggggagggcaa gactgttgac acgaaacaac cggtgacagt tgttacgcag     900
ttcattgggg atccgttgac agaaatcaga cgtctgtatg tgcagggtgg aagacgatc      960 aacaactcga aaacgtcgaa cttggcagac acatatgatt cgattactga caaattctgt     1020
gatgcgacga aagaggcgag tggagacacg aacgatttca aagcgaaagg agccatgtca     1080
ggattcagca cgaacctgaa caatgggcag gttctggtga tgtcattgtg ggatgatcat     1140
acggcgaaca tgctgtggct tgattcgaca tacccgacgg actcgacgaa gacaggtgca     1200
agccgtgggc cttgtgcggt gtcgtctggt gttcctaaag acgttgaaag ccaatatggt     1260
gatgcgactg tcatttactc agacattaag ttcggtgcga tcaactcgac gttcaagtgg     1320
aattag                                                                1326
```

<210> SEQ ID NO 45
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
atggcaactt tggttggaat tctggtgtca ttgtttgcgc tggaggttgc gctggaaatt       60
ggaacccaga cctcggagag ccatccgtca ttgagctggg agctgaatgg tcagagacag      120
acgggatcga ttgtgattga ttcgaactgg aggtggctgc atgatagtgg caccaccaac      180
tgctatgatg ggaatgaatg gagttcagat cttttgcccgg atccggaaaa atgctcgcaa     240
aattgctatc ttgagggtgc ggactacagt ggaacttatg ggatttcaag cagtggaaat     300
tcgttgcaac ttggatttgt gacaaaaggg tcttattcga caaacattgg aagccgtgtt      360
tatttgctga agatgaaaa cacctatgca acgttcaaat tgaagaacaa ggaattcacg       420
ttcacagctg atgtgagcaa ccttccgtgt ggattgaatg gggctttgta ttttgttgcg      480
atgcctgcag atgaggaaaa atcgaagtat ccacttgcga aaccaggagc taagtatggg     540
atgggatatt gtgatgcgca gtgcccacat gacatgaaat tcatcaatgg tgaggcgaat     600
attcttgact ggaaaccatc gtcaaatgat gagaatgcag gggctggaag atacggaacg     660
tgctgcactg aaatggatat ctgggaagct aactcacagg cgactgcata cactgttcac     720
gcatgctcga agaatgcacg ttgtgagggt actgagtgcg agacgacga tggacgatac      780 aacgggatct gtgacaaaga tggatgcgat ttcaactcat ggagatgggg aaacaaaacg      840 ttcttttggcc cgaatctgat tgttgatagc tcgaaccgg tgaccgtcgt acccagttt       900 attggtgatc cgttgacaga aatcagacgt atctatgttc agggcgggaa ggtgatccag     960
```

```
aactcgttca cgaacatcag tggagtggca agtgttgatt cgattacgga cgctttctgt   1020
aatgaaaata aagtggcgac gggagacacg aatgacttca aggccaaggg aggaatgtct   1080
ggcttcagca aggcattgga cactgaagtt gttttggttc tgtcattgtg ggatgatcac   1140
acagcgaaca tgttgtggct tgattcgacg tatccaacag attcgagcgc tttgggagcg   1200
agtcgtggac cttgcgccat aacatcgggt gagccgaaag atgttgagag tgcatctgcg   1260
aatgcatcag ttaagttttc ggacatcaag tttggtgcga ttgattccac ttactaa     1317
```

```
<210> SEQ ID NO 46
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
```

```
atgctgacat tggtgtattt cttgctgtcg ctggtcgtgt ctcttgagat tgggactcaa    60
cagtccgagt cgcatcctca gttgagctgg cagaatggct cgagctcagt gtcaggttcc   120
attgtgcttg actcgaactg gaggtgggtg catgacagcg ggaccacaaa ctgctacgac   180
ggaaacctct ggtcgactga tctttgcccg agctctgaca cctgcacctc gaaatgctac   240 atcgaggag ccgattactc aggaacgtat ggaatcacaa gcagtggctc aaagctgact   300
ctgaagtttg tgacgaaggg atcgtattcg acgaacattg gaagccgtgt ttatttgttg   360
aaggatgaaa cacgtatga acattcaaa ttgaagaaca aggaattcac attcacagtg   420
gatgactcga agctggattg cggtctgaat ggtgcgttgt attttgttgc aatggatgct   480
gatggcggga aagcgaaata ttcgagcttc aaacccgggg cgaaatatgg aatgggatat   540
tgtgatgcgc agtgcccgca tgacatgaaa ttcatcagcg gaaaggcgaa tgttgatgac   600
tggaagccgc aagacaacga tgaaaactca ggaaacggga acttggaac atgctgctcg   660 gaaatggata tctgggaagg aaacgctaag tcacaggcat acactgtgca tgcttgcaca   720
aagagcggac agtacgagtg cactggccaa cagtgtggag acacagattc aggagacagg   780
ttcaagggaa catgcgacaa ggatggatgt gattatgcgt catggaggtg gggagaccag   840
agcttctatg gtgagggtaa aaccgttgac accaaacagc ccttgacagt tgttactcaa   900
ttcgttggtg atccgttgac agagatcaga cgtgtttatg ttcagggtgg aagacgatc   960 aacaactcga agacatcgaa cttggcagac acatatgatt cgatcactga caattctgc  1020 gatgcgacga agaggcgtc tggagatacc aatgatttca aggccaaagg tgctatgtca  1080
gggttcagca cgaacctgaa cactgctcag gttctggtga tgtcgttatg ggatgatcac  1140
actgctaaca tgttgtggct tgattcgaca tatccgactg actcgacgaa gacagggcg  1200 agccgtggac cgtgcgccgt gtcatcaggt gttcccaagg atgttgaaag ccaacatggt  1260
gatgccaccg tgatctactc agacatcaag ttcggggcta tcaactcgac gtttaaatgg  1320
aactag                                                             1326
```

```
<210> SEQ ID NO 47
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
```

```
atgctttcat tgtgttttt acttggattc ggggtttctc ttgaaattgg aactcaacaa      60
tctgaaaatc atccaacttt aagctggcaa caatgcacaa gcagtggatc atgcacttca     120
caatcaggct caattgtcct tgattcgaat tggagatggg ttcatgatag tggaactact     180
aattgctatg atggaaatga atggagttca gatctttgtc cagacccaga acatgctca     240 aagaattgct atcttgatgg tgcagattat agtggaacat atggaattac aagcaatgga     300
tcatcattaa agcttggatt tgttaccgaa ggatcatatt caacaaacat ggatctcgt     360 gtttatctca aaaagatac aaatacatat caaatcttca aattgaagaa tcacgagttc     420
acattcacag ttgatgtttc taatcttcca tgtggattga atggtgcttt atatttcgtt     480
gaaatggaag cagatggagg aaaagggaaa tatccacttg ctaaaccagg agctcaatat     540
ggaatgggat attgtgatgc acaatgtcca catgatatga aattcatcaa tggaaatgca     600
aatgttcttg actggaaacc acaagaaaca gatgaaaatt caggaaatgg tcgatatgga     660
acatgttgca cagaaatgga tatttgggaa gctaactcac aagcaacagc atatacacca     720
cacatttgta caaaggatgg acaataccaa tgtgaaggaa cagaatgtgg agatagtgat     780
gcaaaccaaa gatacaatgg agtttgtgat aaagatggat gtgatttaa ctcatatcga     840 cttggaaaca agacattctt tggtccaggt ttaattgttg attcgaagaa accagtgaca     900
gttgttactc agttcatcac tagcaatggt caagatagtg gcgatttaac cgaaattcga     960
cgtatctatg ttcaaggtgg aaagacaatt cagaattcat tcacgaatat tgctggactc    1020
acatcagttg attcaattac agaagcattc tgtgatgaat caaagatct ctttggagat    1080 actaatgact tcaaggctaa aggaggattt acagcgatgg gaaaatcact cgatactggt    1140
gttgttttag ttttatcatt atgggacgat cattcagtta atatgttatg cttgattca    1200 acctatccaa cggatgcagc tgcaggtgcc ttaggaaccc aacgtggacc atgtgctaca    1260
tcttcaggtg ctccaagtga tgttgaaagt caatcaccag atgcttcagt gacattttct    1320
gacattaaat ttggtccact tgactcaact tactaa                              1356
```

<210> SEQ ID NO 48
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
atgctggctt cggttgttta tttggtgtcg ctggttgtgt ctcttgagat tggaactcaa      60
cagtcagagg agcaccccaa gttgacgtgg cagaatgggt caagctcagt atcaggctct     120
attgtgctgg attcgaactg gagatggctg catgacagcg ggacgaccaa ctgctatgac     180
ggaaacttgt ggagcgatga tctttgccca acgcagaca catgctcatc gaaatgttac     240
atagagggag cagattattc gggaacttat ggaatcacgt cgagtggctc aaaggtgact     300
ctgaaattcg ttacaaaggg gtcatattcg caaacattg gaagccgcat ttacttgttg     360
aaagacgaaa acacctatga aacgttcaaa ttgaagaaca aggaattcac gttcacagtg     420
gatgattcga agcttgactg tgggttgaat ggtgcattgt atttgttgc gatgatgcg     480 gatgggggaa aagcgaaata ttcgagcttc aaaccagggg cgaaatatgg aatgggatat     540
tgtgatgcac agtgcccaca tgacatgaaa ttcatcagcg gaaagcgaa tgttgatgac     600 tggaagcccc aagacaatga tgaaaattca ggagacggga acttggaac atgctgttcg     660 gaaatggata tctgggaagg aaacgcaaaa tcacaggcat atacggtgca cgcttgctca     720
```

```
aagagtggac aatacgaatg cactgggcaa caatgtggag acacagattc gggtgacagg     780
ttcaaaggaa cttgcgacaa agatggatgt gactatgcgt cgtggagatg gggagaccaa     840
agcttctatg gtgagggcaa aactgttgac accaaatcgc cagtgacagt tgttacccaa     900
ttcattggag atccattaac ggaaatcaga cgtgtctatg ttcagggtgg caagacgatt     960
aacaattcga aaacatcgaa cttggcagac acatatgatt caatcactga caagttctgt    1020
gatgcgacga agacgccac tggggatacc aacgatttca aggccaaagg agcgatggca     1080
ggattcagca cgaatttgaa cactgcgcaa gttctggttt ctgtccattg gggatgatc     1140 atacagccaa tatgttgtgg cttgattcga cgtatccaac ggattcaaca aaaacaggtg    1200
caagccgtgg accgtgtgct gtgtcgtcgg gtattccaaa ggatgttgaa agccagcatg    1260
gtgatgctac agtcgcgtac tcggacatta agtttggagc tatcaactcg acctttagtt    1320
ggaattagtc cagcaggacg attattttttt ttttga                              1356

<210> SEQ ID NO 49
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atgctgactt tggtgtattt cttgctttcg ttggttgtgt cgcttgagat tggaacgcag       60
cagtcagaag accatcccaa attgacgtgg cagaatgggt caagctcagt gtcagggtcg      120
attgtgcttg attcgaactg gagatggggtt catgacagtg gacgacgaa ctgctatgac      180 ggaaacttgt ggagcaagga tctttgcccg agctcagaca catgctctca gaaatgttac      240
attgaaggag cagattattc ggggacttat ggaattcagt cgagcggttc aaaactgacg      300
ctgaagtttg tgacgaaagg atcgtattcg acaaacattg gaagccgcgt ttacctgttg      360
aaagatgaaa acacatatga atcgttcaaa ttgaagaaca aggaattcac gttcacagtg      420
gatgattcga agctgaactg tggattgaat ggtgcattgt attttgttgc gatggatgca      480
gatggtggga aagcgaaata ttcgagcttc aaacccgggg cgaaatatgg gatgggatat      540
tgtgatgcgc agtgcccgca tgacatgaaa ttcatcagtg ggaaagcgaa tgttgatgac      600
tggaagccac aggacaacga tgagaattca ggaaacggga acttggaaca tgctgctcg      660 gaaatggata tctgggaagg aaacatgaaa tcgcaggcat acacggtaca cgcttgcacg      720
aagagtggac aatacgagtg cactggacag caatgcggag acacagattc tggtgacagg      780 ttcaaggaa cttgcgacaa ggatgggtgt gattatgcgt catggagatg gggagaccaa       840
agtttctatg gggagggcaa gactgttgac acgaaacaac cggtgacagt tgttacgcag      900
ttcattgggg atccgttgac agaaatcaga cgtctgtatg tgcagggtgg gaagacgatc      960
aacaactcga aaacgtcgaa cttggcagac acatatgatt cgattactga caaattctgt    1020
gatgcgacga agaggcgag tggagacacg aacgatttca aagcgaaagg agccatgtca    1080
ggattcagca cgaaccttaa caatgggcag gttctggtga tgtcattgtg ggatgatcat    1140
acagcgaata tgttgtggct tgattcaacg tatccaactg attcaagtga ttcaacagca    1200
caacgcggac catgcccgac atcatcaggt gtgccgaagg acgttgaaag ccaacatgga    1260
gatgctaccg ttgtattttc ggacatcaag tttggagcca tcaactcgac ctttaaatat    1320
aattag                                                                 1326
```

<210> SEQ ID NO 50
<211> LENGTH: 1320
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

```
atgctgactt tggtagttta tctgctttcg ctggttgtgt ctcttgagat tggaactcaa      60
caatcagaga gtcatcctgc attgacgtgg cagagagaag ggtcttcggc atcaggttct     120
attgttcttg attcgaattg gagatgggtt catgatagtg ggaccaccaa ttgttatgat     180
ggaaatgaat ggagcacgga tctttgtcca agttcagata catgcacaca aaaatgttat     240
attgagggag cagattattc gggaacttat ggaattacaa ccagtggttc aaagttgacg     300
ctgaaatttg ttacgaaggg atcatattca acaaacatag gaagccgtgt ttatctgttg     360
aaagatgaga atacttatga acattcaaa ttgaagaata ggaatttac attcacagta      420
gatgattcta aacttgattg tggattgaat ggtgcgttgt attttgttgc gatggatgca     480
gatggtggaa agcaaaaata ctcgagtttc aaaccaggag ctaaatatgg aatggggtat     540
tgtgatgcgc agtgcccgca tgacatgaaa tttatcagtg ggaaagcgaa tgttgaagac     600
tggaaaccac aagacaatga tgaaaattca ggaaatggga acttggaac atgctgttcg     660
gaaatggaca tttgggaggg gaatgcgaaa tcgcaggcat atacagtaca tgcttgcacg     720
aaaagtggac aatacgaatg tacagggact gactgcggag actcagatag ccggtatcaa     780
ggaacttgtg ataaagatgg atgcgattat gcttcatata gatggggtga tcactcgttc     840
tatggtgagg gtaagactgt tgacaccaaa cagcctatta cagttgtaac ccaattcatt     900
ggagatccgt tgacagagat caggcgtctt tatattcaag gtggtaaagt gattaataac     960
tcgaaaacac agaacttggc gtctgtatac gattcgatta ctgatgcatt ctgcgatgcg    1020
acgaaagcag cgagtggtga tactaacgat ttcaaagcaa aaggagcgat ggcaggattc    1080
agcaaaaact tagacactcc acaagttttg gttttgtcat tgtgggatga tcatacagcg    1140
aatatgttgt ggcttgattc aacgtatcca actgattcac gtgacgcaac agcagaacgt    1200
ggaccgtgtg cgacatcgtc aggtgttccg aaagacgttg aaagcaacca agcagatgct    1260
tcagttgtat tctcggatat taagtttgga gcaatcaact cgacctacag ttataattaa    1320
```

<210> SEQ ID NO 51
<211> LENGTH: 1314
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
atgtttggat ttttgctgtc attgtttgcg ctgcaatttg ctcttgagat cgggacacag      60
acctctgaga gtcatccttc gattacctgg gaactgaatg gtgcgaggca atcgggacaa     120
attgtgattg attcgaactg gaggtggctg catgatagtg gaactaccaa ctgctatgat     180
ggaaacacat ggagctctga tctttgcccg gatccggaaa atgctctcca gaactgctat     240
ctcgagggag ctgattacag tggaacttat gggatttcag ccagcggcag ccagttgaca     300
cttggatttg tgcaaagg atcttactcg acaaacattg gaagccgtgt ttacttgctg      360
aaagacgaga acacgtatca aatgttcaaa ttgaagaaca aggaattcac attcactgtt     420
```

```
gatgtgagca atcttccatg cggattgaat ggtgctttgt attttgttgc gatgccttct      480
gatggtggaa aggcgaagta tcctctggcg aaaccaggag ctaaatacgg aatgggctat      540
tgtgatgctc aatgcccgca tgacatgaaa ttcatcaatg gtgaggccaa tgttctggac      600
tggaaacccc agagcaatga tgagaatgca gggacaggaa gatacggaac ttgctgcaca      660
gagatggata tctgggaagc taactctcag gcgactgcat acactgttca cgcttgctcg      720
aagaatgcaa gatgcgaggg aactgagtgc ggagacgaca gcgcttcaca gaggtataac      780
ggaatttgcg acaaagacgg ttgcgatttc aactcatgga ggtggggcaa caagacattc      840
tttggtcctg gtctgactgt tgatagctcg aaacccgtga ctgttgttac acagttcatt      900
ggtgatccgt tgacagaaat cagacgtatc tgggttcagg gcgggaaggt catccagaat      960
tcgttcacga acgtttctgg aataaccagt gtggattcga ttaccaacac tttctgtgat     1020
gaatcgaaag tggcgactgg agacaccaat gatttcaagg cgaaaggtgg gatgtctggg     1080
ttcagcaagg ccttggacac tgaagttgtt ttggtgttgt cgttgtggga tgaccacacc     1140
gcaaacatgt tgtggcttga ttcgacatat ccttcaaatt cgactgctat tggtgcgacc     1200
cgtggcccat gcgccacatc ctcgggtgat ccgaaaaatg ttgagagtgc ttcggcgaat     1260
gcttcagtca aattttccga catcaagttc ggggcttttg actctactta ctaa          1314

<210> SEQ ID NO 52
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atgctggctt tggtgtattt tttgctttcg ttcgttgtat ctcttgagat tgggacgcag       60
cagtcagagg accatccgaa gttgacctgg cagaatggtt caagctcagt gtctggctct      120
attgtgcttg attcgaactg gagatgggta catgacagcg ggaccaccaa ctgctatgat      180
gggaatttgt ggagcacaga tctttgcggg agttcagaca catgctcatc aaaatgctac      240
attgagggag ccgattattc tggaacatat ggtatctctg ccagtggctc aaagctgacc      300
ctcaagtttg tgacgaaggg atcgtattcg acaaacattg gaagccgtgt ttacctgttg      360
aaagatgaga cacctatga aactttcaaa ttgaagggca aagagttcac attcacagtt       420
gatgattcga gcttgattg cgggttgaat ggtgcgttgt actttgttgc gatgatgcg        480 gatggtggaa aagcgaaata ttcgagcttc aaacccgggg cgaaatatgg aatgggatat      540
tgtgatgcac agtgcccgca tgacatgaaa ttcatcagcg gaaaggcgaa tgttgatgac      600
tggaagccgc aagacaacga cgaaaattca ggaaacggga acttggaac atgctgctcg       660 gaaatggata tctgggaggg aaatgcaaag tcccaggcat acaccgtcca tgcttgcaca      720
aagagtggac aatacgaatg cacaggccaa cagtgcggag acaccgactc cggtgacagg      780
ttcaagggaa catgcgacaa ggatgggtgt gattatgcgt catggagatg gggagaccag      840
agcttctatg gagaaggcaa gactattgac accaaacagc cagtgacagt tgttactcag      900
ttcattggag atccgttgac tgagatcaga cgtgtctatg tccagggtgg caaagtgatc      960
aacaactcga agacctcgaa cttggctaac gtctatgatt cgatcactga caattctgc      1020 gatgacacga aagatgcgac tggagatacc aacgatttca aggcaagggg agcgatgtca     1080
ggattcagca caaatctgaa cactgcccag gttctggtga tgtcgttgtg ggatgaccat     1140
accgccaaca tgttgtggct tgattcaacg tatccgactg actcgacaaa gactggagcg     1200
```

```
agccgtggcc cctgcgctgt gttgtcgggt gttccaaaaa acgtagaaag ccagcatggt    1260
gatgctacgg ttatttactc agacatcaag ttcggggcta tcaactcgac cttcagttat    1320
aattaa                                                               1326

<210> SEQ ID NO 53
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atgctggctt tagtgtattt cttgctttca ttggtggtgt ctcttgagat tggaacgcag      60
caatcagagg accatccgaa gctgacctgg cagaatgggt caagctcggt gtctgggtct     120
attgtccttg attcgaactg gaggtgggtt catgacagcg ggaccacgaa ctgctatgat     180
gggaatttgt ggagcacgga tctttgcccg agctcagaca catgcacatc gaagtgttac     240
attgagggag cagactattc gggaacatat ggaattacat ccagtgggtc aaaggtgacg     300
ctgaagtttg tgacgaaggg atcatattcg acgaacattg gcagtcgtat ttacttgttg     360
aaagatgaga acacttatga aacgttcaaa ttgaagaaca aggaattcac attcacagtg     420
gatgattcac agcttaattg cggattgaat ggtgcactgt attttgttgc gatggatgca     480
gatggtggaa aagcgaaata ttcgagcttc aagccagggg cgaaatatgg aatgggatat     540
tgtgatgcac agtgcccgca tgacatgaaa ttcatcagtg ggaaagcgaa tgttgatgac     600
tggaagccgc aagacaatga tgaaaactcc ggaaacggga acttggaac atgctgctct     660 gaaatggata tctgggaggg gaacgcaaaa tcgcaggcat atacggttca cgcttgcacg     720
aagagtggac agtatgaatg cacgggacag cagtgcggag acacagattc gggtgacagg     780
ttcaagggaa catgcgacaa ggatggatgc gattatgcgt catggagatg gggagaccag     840
agcttctatg gtgagggcaa gactgtagac accaaacagc cagtgacagt tgttactcag     900
ttcattggag atccgttgac agaaatcaga cgtctgtatg ttcagggcgg caagacgatc     960
aacaactcga agacatcgaa cttggcagat acgtatgatt cgatcactga caagttctgc    1020
gatgcgacga agaagcatc aggagacaca acgatttca agcgaaagg agcgatgtcg    1080 ggattcagca caaacctgaa cactgcgcag gttctggtat tgtcgttgtg ggatgatcat    1140
acagccaaca tgttgtggct tgattcgacg tacccgacag actcgacgaa aaccggagca    1200
agtcgtgggc cttgtgctgt gacttcgggt gtaccaaagg atgttgaaag ccagtatggc    1260
agtgcgcaag ttgtgtattc ggatatcaag tttggggcta tcaactcgac ctactaa      1317

<210> SEQ ID NO 54
<211> LENGTH: 1314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atgtttggat ttttgctgtc attgtttgcg ctgcaatttg ctcttgagat cgggacacag      60
acctctgaga gtcatccttc gattacctgg gaactgaatg gtgcgaggca atcgggacaa     120
attgtgattg attcgaactg gaggtggctg catgatagtg ggactaccaa ctgctatgat     180
ggaaacacat ggagctctga tctttgcccg gatccggaaa aatgctctca gaactgctat     240
```

```
ctcgagggag ctgattacag tggaacttat gggatttcag ccagcggcag ccagttgaca    300
cttggatttg tgacaaaggg atcttactcg acaaacattg gaagccgtgt ttacttgctg    360
aaagacgaga acacgtatcc aatgttcaaa ttgaagaaca aggaattcac attcactgtt    420
gatgtgagca atcttccatg cggattgaat ggtgctttgt attttgttgc gatgccttct    480
gatggtggaa aggcgaagta tcctctggcg aaaccaggag ctaaatacgg aatgggctat    540
tgtgatgctc aatcccgca tgacatgaaa ttcatcaatg gtgaggccaa tgttctggac    600
tggaaacccc agagcaatga tgagaatgca gggacaggaa gatacggaac ttgctgcaca    660
gagatggata tctgggaagc taactctcag gcgactgcat acactgttca cgcttgctcg    720
aagaatgcaa gatgcgaggg aactgagtgc ggagacgaca gtgcttcaca gaggtataac    780
ggaatttgcg acaaggacgg atgcgatttc aactcatgga gatggggcaa caagacattc    840
tttggtcctg gtctgactgt tgatagctcg aaaccagtga ctgttgttac ccagttcatt    900
ggtgatccgt tgacagaaat cagacgtatc tgggttcagg gcgggaaggt cattcagaat    960
tcgttcacca acgtttctgg aattacgagt gtggattcga ttaccaacac tttctgtgat   1020
gaatcgaaag tggcgactgg agacaccaat gacttcaagg cgaaaggtgg gatgtctggg   1080
ttcagcaagg ccttggacac tgaagttgtt ttggtgttgt cgttgtggga tgaccacacc   1140
gcaaacatgt tgtggcttga ttcgacatat cctacagatt cgactgctat tggtgcgagc   1200
cgtggaccat gcgccacatc ctcgggtgat ccgaaagatg ttgagagtgc ttcggcgaat   1260
gcttcagtca aattctccga catcaagttc ggggctcttg actctactta ctaa         1314

<210> SEQ ID NO 55
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgcttgtca ttgcattgat tttgcgagga ctttcggtcg gaacagggac tcagcaatca     60
gaaacgcacc caagccttag ttggcagcag acctcgaaag gcggtagtgg acaatcggtt    120
tcaggatcag ttgttcttga ttctaactgg cgctggactc atacgacaga tggtacgaca    180
aactgctacg acggtaacga gtggagttca gatctttgtc cagatgcatc tacatgttct    240
agcaactgcg ttcttgaggg agcagattac tcagggacat atggtatcac cgggagcgga    300
agttcattga gctgggatt tgtgacgaaa gggtcatact cgacgaacat tggttcacgt    360
gtttaccttc ttggagacga aagccactac aagctgttca gcttgagaa caacgaattc    420 acattcacag ttgacgactc taaccttgaa tgtggactga atggagcact ttactttgtt    480
gctatggacg aggatggagg agcatcgaaa tacagtggag ctaagccagg agcgaagtac    540
ggaatgggat attgcgatgc acaatgtcca cacgacatga gttcatcaa cggagatgcg    600 aacgttgaag gatggaagcc atcggataat gacgagaatg caggtacagg aaaatggggt    660
gcatgctgca cagaaatgga tatctgggaa gcgaacaaat atgctacagc atatacacca    720
catatctgca cgaagaacgg cgagtaccga tgtgaaggta cagactgtgg agacactaaa    780
gacaacaatc gatatggagg agtttgcgat aaagacggat gcgacttcaa ctcgtggcgt    840
atgggtaacc agagcttctg ggaccaggt cttatcattg acacaggtaa gccagtgacg    900
gttgtcacgc agttcctggc ggatggtggc tcgcttagcg agatccgtcg taagtatgtt    960
```

| | | | | |
|---|---|---|---|---|
| caaggaggta | aagtgatcga | gaacacagta | actaagatct | caggaatgga tgaattcgac | 1020 |
| tctatcacag | atgaattctg | caatcagcag | aagaaagcat | tcagagacac taacgacttc | 1080 |
| gagaagaagg | gaggtcttaa | gggtcttgga | acagcagtcg | atgctggagt ggttcttgtt | 1140 |
| ctgtcacttt | gggatgacca | tgacgtgaac | atgctttggc | ttgattcaat ctacccaacg | 1200 |
| gattcaggaa | gcaaggcagg | agcagatcga | ggtccatgtg | cgactagctc aggtgttcca | 1260 |
| aaggatgtgg | agagcaacta | tgcatcagca | tcagtgacat | tctcggacat caagttcgga | 1320 |
| ccaatcgact | ccacttacta | a | | | 1341 |

<210> SEQ ID NO 56
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

| | | | | |
|---|---|---|---|---|
| atgctgtcgt | tggtatcaat | atttttggtt | ggtttgggat | tttctcttgg ggttggaact | 60 |
| caacagtcag | aaaagccatcc | ttcgttgagc | tggcagaatt | gctcggctaa aggatcatgc | 120 |
| caatcagtgt | cggggtctat | tgtacttgat | tctaactgga | gatggcttca tgacagtgga | 180 |
| actactaact | gttatgatgg | aaatgaatgg | agcacagatc | tttgtccgga tgcatcgaca | 240 |
| tgcgacaaaa | attgctacat | tgaaggagca | gattacagtg | gaacatatgg aatcacaagc | 300 |
| agcggagcac | agttaaagct | tgggtttgtt | acgaaaggt | cgtattcaac aaacattgga | 360 |
| agtcgtgttt | atttgttgag | ggatgagagt | cattatcaat | tgttcaagtt gaagaatcat | 420 |
| gagttcacgt | tcacagttga | tgacagccaa | cttccatgtg | gattgaatgg tgcgttgtac | 480 |
| tttgttgaaa | tggcggaaga | tggtggagcg | aaaccaggag | cacagtatgg gatgggatat | 540 |
| tgtgatgcac | agtgcccaca | tgacatgaaa | tttattactg | gggaagcgaa tgttaaagat | 600 |
| tggaaacccc | aagagacgga | cgaaaatgca | ggaaacggac | attatggagc atgctgcaca | 660 |
| gaaatggata | tctgggaagc | taactcacaa | gcgacagcat | acaccccaca catttgctcg | 720 |
| aagactggga | tatatcgttg | tgaaggaact | gaatgtggtg | ataatgatgc gaaccagaga | 780 |
| tacaatggag | tttgtgataa | agacggctgc | gatttcaact | catacagatt gggaaacaag | 840 |
| acgttctggg | gaccaggcct | gactgttgat | tcgaacaaag | cgatgatagt tgttacgcaa | 900 |
| ttcaccacga | gcaacaatca | agattccgga | gagttgtcag | aaatccgtcg tatttatgtt | 960 |
| cagggtggaa | agacgattca | gaattcggac | acgaatgttc | aaggaatcac aacaacaaac | 1020 |
| aagattactc | aagctttctg | tgatgaaacg | aaagttacat | tggggacac gaatgatttc | 1080 |
| aaagcaaagg | gaggtttctc | aggcttgagc | aaatcattgg | aaagtggtgc agttctggtt | 1140 |
| ctgtcgctgt | gggatgatca | ttcagtgaac | atgttgtggc | ttgattcgac ctatcctaca | 1200 |
| gattcagcgg | gcaaacccgg | agctgatcgt | gggccatgtg | ctatcacttc aggcgatcca | 1260 |
| aaagatgttg | aaagccaatc | accgaatgct | tcggttacgt | tttcagacat taaattcggt | 1320 |
| cctattgact | caacttactg | a | | | 1341 |

<210> SEQ ID NO 57
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
atgattggaa ttgtactgat tcaaacagtt tttggaattg agttggaac gcagcaatca      60
gagagccatc cgagcctgag ttggcagcag tgttctaaag gcggtagctg cacatcagtt    120
tcaggatcaa ttgtccttga ctctaactgg cggtggacgc atataccaga tggtacgacg    180
aattgctacg atggtaacga gtggagttcg gatctttgtc cggatcctac tacgtgttca    240
aataactgcg ttctggaagg agcagattat tcaggaacgt acggaatcag cacgagtgga    300
agctcagcga aacttggatt tgtgacgaaa ggatcatact cgactaacat tggatcgcga    360
gtttatcttc taggtgacga aagccactac aagatcttcg acctgaagaa caaggaattc    420
acatttacag ttgatgattc taatcttgaa tgtggactga acggcgcgct ttactttgtt    480
gcgatggacg aggatggagg agcatcacga ttcacgcttg cgaagccagg tgctaagtac    540
ggtacaggat attgcgatgc acagtgtcca cacgacatca agttcatcaa cggtgaagcg    600
aatgttcaag actggaaacc atcagacaac gacgataatg caggaacagg acactatggg    660
gcatgctgta cagaaatgga tatctgggaa gcgaacaaat atgcgacagc atatacaccg    720
cacatttgca cggagaatgg cgagtaccga tgtgaaggta aaagttgtgg agactcatca    780
gacgatcgat atggcggagt ttgcgacaaa gacggatgcg acttcaactc atggcgtctt    840
ggtaaccaga gcttctgggg tccaggtctt atcattgaca cagggaagcc agttacagtt    900
gttacgcagt ttgttacaaa ggatggaaca gacagcggtg ctctttcgga gatccgtcgt    960
aagtatgtgc aaggagggaa aacgatcgag aacacagtgg ttaagatttc aggaattgat   1020
gaggttgatt caatcacaga tgaattctgc aatcagcaga agcaagcgtt tggagacacg   1080
aacgactttg agaagaaagg tggactgagt ggtcttggga aggcattcga ttatggagtg   1140
gttcttgttc tgtcactttg ggatgatcac gatgtgaata tgctttggct tgattcagtc   1200
tatccaacta atccagctgg gaaagcagga gcagaccgag gtccatgtgc gactagttca   1260
ggtgatccaa aagaagttga ggacaagtat gcatcagcat cagtgacatt ctcggacatc   1320
aagtttggtc cgatcgattc tacctactaa                                    1350
```

<210> SEQ ID NO 58
<211> LENGTH: 1326
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
atgctgcttt gcttgttgag cattgcgaat tcgcttggcg ttggcacgaa cactgcggag      60
aaccatccga agctttcgtg gaagaacgga ggttcgagtg tttcagggtc agtgacggtg    120
gacgcgaact ggcgttggac tcacatcaag ggcgagacga agaactgcta tgatgggaac    180
ctttggagtg acaagtactg ccctgatgcc gcgacgtgcg gcaagaactg cgtgatcgag    240
ggtgcggact atcaggggac ctacggtgtt tcgtcgagcg gtgatggtct gactctgacc    300
tttgtcacgc acggacagta ctcgacgaac gtcggcagcc gtctgtacct tatgaaggac    360
gagaagactt accaaatgtt caacctgaac gggaaggagt tcacgttcac tgtcgatgtc    420
tcgaaccttc cgtgcggcct gaatggtgcg ctgtactttg tgcagatgga ctccgacggt    480
ggcatggcga gtaccccgaa caaccaggca ggcgcgaagt atgggacggg atattgcgat    540
gcgcagtgcc cgactgacct taagttcatc aacggcatcc gaacagcga tggctggaag    600
cctcagaaga acgacaagaa ctccggcaac ggcaagtacg gcagctgctg cagcgagatg    660
```

```
gatatctggg aagcgaactc gcaggcgact gcgtacactc cccacgtctg tgacaaactc    720
gagcagacgc gatgcagtgg aagttcctgt gggcacactg gtggtggtga gcgtttctcc    780
agctcttgcg atccggacgg ctgcgacttc aactcgtgga gaatgggcaa caagacgttc    840
tggggaccgg gtctgattgt tgacacaaag aagccggttc aggtcgtcac gcagttcgtt    900
ggctcgggca acagctgcac ggagatcaag aggaagtatg ttcagggagg gaaggtcatt    960
gacaactcaa tgagcaacat cgcaggaatg agcaagcagt acaactcagt ttcagacgac   1020
ttctgccagg ctcagaagaa ggcattcggc gacaacgaca gcttcacaaa gcacggtggc   1080
ttccggcagc ttggtgccac acttggcaag ggacacgtcc ttgtgctttc cctttgggat   1140
gaccacgatg tgaacatgct ctggctcgac tctgtttacc cgaccaactc caacaagccc   1200
ggctctgacc gtggaccgtg caagacctcg tccggcattc cggcagatgt tgaatcgcag   1260
gctgcgagct cgtcggtgaa atactccgac atccgcttcg gcgcgatcga ttcgacctac   1320
aagtga                                                              1326

<210> SEQ ID NO 59
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atgctcggtg ccctggttgc gctcgcgtcg tgtatcggtg tcggcacgaa caccccggag     60
aagcaccccg atttgaagtg gacgaatggt ggatcttcag tgtcgggctc gatcgtcgtc    120
gactccaact ggcgttggac ccacatcaag ggcgagacga agaactgcta tgatggaaac    180
ctgtggtccg acaagtattg cccagacgcc gcgacttgcg ggaagaactg cgttctcgag    240
ggcgctgatt actccggcac ttatggcgtc acgaccagcg gcgacgccgc aaccctgaag    300
tttgtcacgc acggccagta ctcgacgaac gtcggcagcc gtctgtacct gctcaaggat    360
gagaagacgt accagatgtt caacttggtg ggcaaggagt tcacgttcac cgtggatgtc    420
tcgaaccttc cgtgcggcct caacggtgct ctctactttg tccagatgga ttctgatggt    480
gggatggcca gtaccccgga taaccaggcg ggcgcgaagt acggcactgg ctattgcgat    540
gcgcagtgcc cgactgacct gaagtttatt aacggcatcc gaacagcga tggctggaag    600 ccgcagaaga acgacaagaa ctcgggcaat ggcaagtacg gcagctgctg cagtgagatg    660
gatatctggg aggcgaattc aatggccacg gcttacaccc cgcacgtctg cgacaagttg    720
gaacagaccc ggtgctccgg aagtgcttgc ggccagaacg gcgtggcga tcgtttctcg    780 agctcatgcg accctgatgg gtgcgacttc aactcgtgga gaatgggtaa caagaccttc    840
tggggtccgg gcttgatcgt tgataccaag aagcccgtcc aggttgtcac gcagttcgtc    900
ggttccggcg ggtcggtcac cgagatcaag aggaagtatg ttcagggggg caaggtcatc    960
gacaactcaa tgaccaacat tgctgcaatg agcaagcagt ataattcggt ctcggatgag   1020
ttctgccagg cacagaagaa ggcgttcggc gacaacgaca gcttcaccaa gcacggtggc   1080
ttcaggcagc tcgcgccac cctctcaaag ggccatgtcc tggtgctctc cctgtgggac   1140
gaccatgatg tgaacatgct ctggctggac tccgtctacc cgaccaactc caacaagccc   1200
ggagcggacc gtgggccttg caagacttcc agcggtgttc cgtctgatgt cgagtcccag   1260
aatgctgact caaccgtcaa gtattccgac atccgcttcg gagccatcga ttcgacctac   1320
```

```
agcaagtaa                                                          1329
```

<210> SEQ ID NO 60
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
atgctcgctg ctgcattgtt cacatttgca tgtagtgttg gagttgggac taaaactcca    60
gaaaaccatc ctaagttgaa ctggcagaac tgtgcgagca aggaagttg ctcgcaagtc    120
tctggcgaag ttacgatgga ctcaaactgg cgatggacgc acgatggcaa tggtaagaac    180
tgctatgacg gcaacacttg gatctcctcc ctctgcccgg acgacaagac ctgctcagac    240
aagtgtgttc tcgatggtgc ggaataccag gcgacctatg gtatccaaag caacggcact    300
gcactgaccc tgaagttcgt cacccatggc tcctactcga ccaacatcgg ctcccgtttg    360
tatctcttga aggacaaatc aacctactat gtcttcaaac tgaacaacaa ggagttcaca    420
ttcagtgttg atgtctcgaa gctcccatgc ggcctcaacg tgctttata ctttgtggaa    480
atggacgcag acggaggcaa agcgaagtat gcaggtgcga aaccaggagc agaatacgga    540
ttgggttatt gtgatgcaca gtgcccgagc gacttgaagt tcatcaacgg agaggcgaac    600
tcagagggat ggaagcccca gtcgggtgac aagaacgctg gaaacggaaa gtatggttcg    660
tgctgctcgg aaatggacgt ttgggaatcg aactcgcagg caacagcact gacaccacat    720
gttttgcaaga cgactgggca gcagcgatgc agtggcaagt cggaatgtgg cggtcaggac    780
gggcaagacc gattcgctgg actttgcgac gaagacggat gtgacttcaa caactggcga    840
atgggagaca agacattctt cggacctggt ttaattgttg acacgaaatc accatttgtt    900
gtcgtcacac aattctacgg atcgccagtg actgagatca ggaggaagta tgtccagaac    960
gggaaggtga tcgagaactc taagtccaac attccgggaa ttgacgcaac tgcagcaatc   1020
agtgatcact tctgcgaaca gcaaaagaag gccttggtg atacaaacga tttcaagaac   1080
aagggtggat tcgcgaagct tggccaagtc tttgaccgtg aatggtcct cgtgttgtca   1140
ttgtgggatg atcatcaggt cgcaatgttg tggttggatt ctacttaccc gaccaacaaa   1200
gataagagcc aaccaggtgt tgaccgtggg ccttgtccga ccagctctgg aaagccagac   1260
gatgtcgaaa gtgcttctgc ggatgcgaca gtcgtgtatg ggaacatcaa gtttggagca   1320
cttgattcaa cttactaa                                                1338
```

<210> SEQ ID NO 61
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
atgctgctgt gtctgttggg cattgcctct tctttggacg cggggacgaa cactgccgag    60
aaccacccgc agctctcatg gaagaacgga gggtcaagtg tatcagggtc ggtcaccgtt   120
gacgccaact ggaggtggac ccacatcaag ggcgagacga agaactgcta cgacgggaac   180
ctgtggagcg acaagtactg tccggatgcg gccacctgcg ccagaactg cgtgatcgag   240
ggtgccgact accaggggac ctacggcgtg tcggcgagcg gaaacgcact cactctcacg   300
```

| | |
|---|---|
| ttcgtcactc acggccagta ctcgacgaat gttggaagcc gcctgtatct cctcaaggac | 360 |
| gagaagacat accagatctt caacctgatc gggaaggagt tcacgttcac tgtcgatgtg | 420 |
| tcaaacctgc cgtgcggcct gaatggggcg ctctacttcg tgcagatgga cgccgatggt | 480 |
| ggcaccgcaa agtactccga caacaaggcg ggtgccaagt acgggacagg ttactgtgac | 540 |
| gcgcagtgcc caactgacct gaagttcatc aacggcatcc gaacagcga cggatggaag | 600 |
| ccgcagaaga acgacaagaa ctccgggaac ggcaggtacg gcagctgctg cagcgagatg | 660 |
| gatgtctggg aggcaaattc ccttgcgacg gcttacaccc cccacgtctg tgacaagctt | 720 |
| gagcaagtac gatgtgacgg ccgggcatgt gggcagaacg tggcggtga ccggttcagc | 780 |
| agctcctgcg atcctgatgg ttgcgacttc aactcatggc gattgggcaa caagactttc | 840 |
| tggggaccgg gcctgatcgt cgacaccaag cagccggtgc aagttgttac ccagtgggtc | 900 |
| gggtcgggca cttctgtgac tgagatcaag aggaagtatg ttcagggtgg aaaggtgatc | 960 |
| gacaactcgt tcaccaagct cgacagcctg accaagcagt acaattcggt ctccgacgag | 1020 |
| ttctgtgtcg ctcagaagaa ggcattcggc gacaacgaca gcttcaccaa gcacggaggg | 1080 |
| ttccggcaac tcggcgcaac actcgcaaag gccatgtgt tggtgctgtc gctttgggac | 1140 |
| gaccacgacg tgaacatgct ctggctcgac tcagtgtatc cgacgaactc gaacaagccc | 1200 |
| ggcgccgatc gtgggccgtg taagacctca tcaggagtcc cggccgatgt cgaatctcag | 1260 |
| gctgcaagct cgtcggttaa gtactccgac atccgctttg ggcaatcga ctcgacctac | 1320 |
| aagtaa | 1326 |

<210> SEQ ID NO 62
<211> LENGTH: 1338
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

| | |
|---|---|
| atgctggctg ctgcattgtt caccttcgca tgtagcgttg gagttggaac caagacgacc | 60 |
| gagacccacc cgaagctgaa ctggcaacag tgtgcctgca agggaagctg ctcgcaagtg | 120 |
| tcgggcgaag ttacgatgga ctcgaattgg cgctggacgc acgatggcaa tgcaagaac | 180 |
| tgctatgacg gcaacacgtg gatcagcagc ctctgccccg acgacaagac ctgctctgac | 240 |
| aagtgcgttc ttgatggtgc ggaatatcag gcgacctacg gcatccagag caacgggact | 300 |
| gctcttactc ctaagtttgt gacgcacggc tcgtactcga cgaacatcgg ctctcgcctt | 360 |
| tacctgctga aggacaagtc gacgtactac gtcttccagc tgaacaacaa ggaattcaca | 420 |
| ttcagcgttg acgtcagcaa acttccttgc ggcctgaacg gtgctttgta ctttgtggaa | 480 |
| atggacgcgg atggtggtaa atcgaagtac gcaggtgcga agccaggtgc tgaatacggc | 540 |
| cttggttact gcgatgcgca atgcccgagc gaccttaagt tcatcaacgg tgaagcgaac | 600 |
| agcgagggat ggaagccgca gtccggtgac aagaatgccg ggaacggtaa atacgggtcg | 660 |
| tgctgctcag aaatggacgt ttgggaatcg aactcgatgg caaccgctct taccccgcac | 720 |
| gtttgcaaga cgaccggcca gacgcgctgc agcggaaaga gcgaatgcgg cggccaagac | 780 |
| ggtcaggacc ggttcgctgg aaattgtgac gaggacggct cgacttcaa caactggaga | 840 |
| atgggcgaca gactttctt cggccctgga ctcactgtcg acacgaaatc accgtttgtc | 900 |
| gttgtgacgc aattctacgg ctccccggtt acgaaatcc gccgcaagta cgttcagaac | 960 |
| ggaaaggtga tcgagaacgc gaagtcgaac atccccggaa ttgacgcaac aaacgcaatc | 1020 |

```
agcgacacgt tctgcgaaca gcagaagaag gcctttggtg acacgaacga cttcaagaac      1080
aagggtggtt tcacgaagct gggctcagtg ttctcgcgcg gaatggtcct cgtgctgtca      1140
ctttgggacg accaccaggt cgcgatgctt tggctcgact caacctaccc cacgaacaag      1200
gataagagcg tccctggagt cgaccgtggg ccttgcccga cctcatctgg aaagcccgac      1260
gatgtcgaga gcgcttctgg cgatgccacc gtcgtctatg gaacatcaa gttcggggca       1320 ctcgactcca cttactaa                                                    1338
```

<210> SEQ ID NO 63
<211> LENGTH: 1326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
atgctgcttt gcctgtggag cattgcgtac tcgcttggtg ttgggacgaa cactgcggag       60
aaccatccaa agctttcgtg gaagaatgga gggtcgagtg tttctggatc agtcacggtc      120
gatgcgaact ggcgttggac ccacatcaag ggcgaaacca agaactgcta tgacgggaac      180
ctttggagtg acaagtactg ccccgatgcc gcgacctgcg ggaagaactg cgttatcgag      240
ggtgccgact atcaggggac ctacggtgtt tcagcgagcg gtgacggtct gactctgacc      300
tttgtcactc acggtcagta ttccacgaac gtcgggagcc gcctgtacct catgaaggac      360
gagaagacgt accagatctt caacctgaac ggcaaggagt ttacctttac tgtcgatgtc      420
tcgaacctgc cgtgcggtct gaacggtgca ctgtactttg tgcagatgga ctcggacggt      480
gggatggcga agtaccctga caaccaggcg ggcgcgaagt acgggacggg atactgcgat      540
gcgcagtgcc cgactgacct taagttcatc aacggcatcc gaacagtga tggctggaag      600 ccccagaaga acgacaagaa ctccggcaat ggcaagtacg gcagctgctg cagtgagatg      660
gacatctggg aggcgaactc gcaggcaact gcgtacactc gcacgtctg cgacaaactc      720 gagcagacac ggtgcagcgg gagtgcgtgc ggccacactg gcggcggcga gcgtttctcc      780
agctcttgcg atccggatgg gtgcgacttc aactcatggc gaatgggcaa caagacgttc      840
tggggaccgg gtctgattgt tgacacgaag aagccggttc aggttgtgac gcagttcgtt      900
gggtcgggca cagctgcac ggagatcaag aggaagtatg tccagggcgg gaaagtgatc      960
gacaactcga tgagcaacat cgcaggaatg accaagcagt acaactcggt ttccgacgac     1020
ttctgccagg cacagaagaa ggccttcggc gacaacgaca gtttcacaaa gcacggtggc     1080
ttccgccagc ttggtgcaac tcttggcaag ggacacgtgc tggtgctgtc gctgtgggat     1140
gaccacgacg tgaacatgct ctggctggat tctgtttacc cgaccaactc caacaagccg     1200
ggctctgacc gtgggccgtg caagaccctcg tccggcattc cggcagatgt tgaatcccag     1260
gcggcgagct cgtcagtgaa gtactccgac atccggttcg gcgccattga ttcgacctac     1320
aagtga                                                                 1326
```

<210> SEQ ID NO 64
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
atgttttag cattgtttgt tttaggtaag tcgcttggta ttgcaaccaa tcaggcagaa      60
aatcatccaa aattaacgtg gactcgctat cagtcgaaag gatcgggtca gaccgttaat     120
ggagaagttg ttcttgattc taactggagg tggactcatc attcaggaac taactgttat    180
gatggaaata catggtcgac atcactttgt ccagatccac agacatgttc aagcaattgt    240
gaccttgatg gtgcggacta tccaggaact tatggaatca gtagctcagg gaattctttg    300
aaacttggat ttgttacaca tgggtcatac tcaacaaaca ttggttcacg agtttactta    360
ttgcgtgata gtaagaatta tgagatgttc aagctgaaga acaaagaatt tacgttcaca    420
gttgatgatt ctaaacttcc atgtggattg aatggagcgt tatattttgt tgcgatggaa    480
gaagatggag gagttgcgaa gaactcaatt aacaaagcag gagctcagta tggaacaggt    540
tattgtgatg cgcaatgccc acatgatatg aaattcatca acggagaagc taatgttttg    600
gattggaaac cgcagtcaaa tgatgaaaat tcaggtaatg gacgttatgg agcatgctgc    660
atagaaatgg atatctggga agctaattca atggcgactg cttatacacc acatgtttgc    720
acagttacag gaattcacag gtgtgaagga acagagtgtg agacacaga tgcaaatcaa     780
cggtacaatg gtatttgtga taaggatggt tgtgatttca attcctacag gatgggagac    840
aaaagcttct ttggagtggg caagacagtt gattcaagca aaccagtgac agttgtgacg    900
caatttgtga caagcaatgg tcaagatgga ggaacattaa gcgaaatcaa aagaaagtat    960
gttcaaggag gaaaagtgat tgagaattct aaagtgaata ttgcaggtat aacagcagtt   1020
aactcaatta cggatacgtt ttgcaatgag caaaagaaag cgtttggaga taacaatgat   1080
tttgagaaga agggaggatt aggagcattg agcaaacaac ttgacctagg aatggtttta   1140
gttttatcat tatgggacga ccactcagtt aacatgctct ggcttgattc aacgtatcct   1200
acggacgccg cagcaggagc attaggaact gagcgaggag catgtgctac atcctctggt   1260
aaaccatcag acgttgaatc gcaatcaccct gatgcatcag ttacattttc agatatcaag   1320
tttggaccaa ttgattcgac ttattaa                                       1347
```

<210> SEQ ID NO 65
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
atgttgttgg cactctttgc ttttggaaaa tcacttggta ttgcaaccaa tcaagcagaa      60
aaccatccaa agttgacatg gactcgttat caatcgaaag gatcgggtca aacagttaat     120
ggagaaatcg ttcttgattc taactggagg tggactcatc attcaggaac taactgctat    180
gatggaaata catggtcaac atcactttgt ccagatccaa cgacgtgctc aaacaattgt    240
gaccttgatg gagcagatta tccaggaact tatggtattt cgtcatcagg aaattcattg    300
aaacttggat ttgttacgca tggatcatac tcgacaaaca ttggctcaag agtttatttg    360
ttacgagaca gtaagaatta tgaaatgttc aagcttaaga acaaggaatt tacttttcaca   420
gttgatgatt ctaagcttcc atgtggttg aatggagcat tatactttgt tgcgatggat    480
gaagacggag gagtttctaa aaactcaatt aacaaagcag gagcacaata tggaacaggt    540
tattgtgatg cacaatgtcc acatgatatg aaattcatca atggagaagc taatgttttg    600
gattggaaac ctcaatctaa cgatgaaaac tcaggtaatg gacgttatgg agcgtgctgc    660
```

| | |
|---|---|
| acggaaatgg atatctggga agctaattct atggctaccg cttatacacc acatgtctgc | 720 |
| acagttacag gaattcgaag gtgtgaagga acagagtgtg gagacactga tgcaaatcaa | 780 |
| cgctacaatg gtatttgtga taaggatggg tgcgatttca actcatatag gttaggagat | 840 |
| aagagtttct ttggagttgg taaaacagtt gattcaagca aaccagttac agttgttacg | 900 |
| caatttgtta ctagcaatgg acaagactca gggacgttgt ctgaaattcg acgaaagtat | 960 |
| gttcaaggtg gtaaagtgat tgagaattct aaagtaaata ttgcaggaat ggcagcaggt | 1020 |
| aattctatca ccgatacatt ctgcaatgaa caaagaaag catttggcga taataatgat | 1080 |
| tttgagaaga agggaggatt aggagcattg agcaaacaac ttgattcggg aatggttttta | 1140 |
| gttttgtcct tatgggatga ccactcagtt aacatgttgt ggcttgattc aacatatccc | 1200 |
| actaatgcag ccgcaggagc gttaggaacg gaacgaggag cttgtgccac atcgtctggt | 1260 |
| gcaccgtcag acgttgaatc gcagtcacct gatgctacgg tcactttctc tgatatcaag | 1320 |
| tttggaccaa ttgattcaac ttactaa | 1347 |

<210> SEQ ID NO 66
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

| | |
|---|---|
| atgattttag cacttcttgt tcttggaaaa tctcttggta ttgcaaccaa tcaagcagaa | 60 |
| actcatccaa agttaacttg gactcgatat caatcaaaag gatcaggttc aacagttaat | 120 |
| ggagaaattg ttcttgattc taactggagg tggactcatc attcaggaac caactgttat | 180 |
| gatggaaata catggtcaac atcactttgt ccagatccaa caacatgttc aaacaattgt | 240 |
| gaccttgatg gagcagatta tccaggaact tatggcatt cgacatcagg aaattcattg | 300 |
| aaacttggct tgttacaca tggatcatat tcaacaaata ttgggtcaag agtttactta | 360 |
| ttaaaagata caaagagtta tgaaatgttc aaacttaaga ataaggagtt taccttcaca | 420 |
| gttgatgatt ctaaacttcc atgcggattg aatggagctt tatactttgt tgcaatggat | 480 |
| gaagatggag gagtttctaa aaactcaatt aacaaagcag gagctcaata tggaacaggt | 540 |
| tattgtgatg cacaatgtcc acatgatatg aaattcatta atggagaagc caatgttttg | 600 |
| gattggaaac cacagtcaaa cgatgagaac tcagtaatg gacgatatgg agcttgctgc | 660 |
| acagaaatgg atatttggga agctaattca atggcaacag cttacacacc acacgtttgt | 720 |
| acagtcaccg gacttcgcag gtgtgaagga acagaatgtg gagatacaga caatgatcaa | 780 |
| cgatacaatg gaatttgtga taaagatggg tgtgacttca actcatatcg attaggtgat | 840 |
| aagagtttct ttggagttgg aaagacagtt gattcaagca aaccagttac agttgttacc | 900 |
| caatttgtca ctagcaatgg acaagactca ggaacattat cggaaatccg aagaaagtat | 960 |
| gttcaaggag gtaaagtaat tgaaaattct aaagttaacg ttgcaggaat aacagcaggt | 1020 |
| aattcggtta ctgatacatt ctgtaatgaa cagaagaaag catttggaga taataatgat | 1080 |
| tttgagaaga agggaggatt tggagcatta agcaaacaac tcgttgctgg aatggttttta | 1140 |
| gttttatcat tatgggacga tcattcagtt aacatgttat ggcttgattc aacataccca | 1200 |
| actaatgcag cagcaggagc tttaggaaca gagcgaggag cctgtgccac ctcatctggt | 1260 |
| aaacttctg atgttgagtc tcaatcacct gacgctacag ttaccttctc agacatcaag | 1320 |
| tttggaccaa ttgattcaac ttactaa | 1347 |

<210> SEQ ID NO 67
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
atgattttag cacttctgtc tcttgcaaaa tctcttggta ttgcaactaa ccaagcagaa      60
actcatccaa agttgacatg gactcgatat caatcaaaag gatcaggtca acagtcaac     120
ggagaaattg ttcttgactc taactggagg tggactcatc attcaggaac caactgttat     180
gatggaaata catggtcaac atcactttgt ccagatccaa caacatgttc aaataactgt     240
gaccttgatg gagcagatta tccaggaact tatggtatta gcacatcagg aaattcactg     300
aaacttggat tgttacaca tggatcatat tcaacgaata ttggatcaag agtttacttg     360
ttacgtgatt ctaaaaatta tgaaatgttc aaacttaaga ataaggaatt taccttcaca     420
gttgatgatt ctaaacttcc atgtggactg aatggagctt tgtactttgt tgcaatggac     480
gaagatggag gagtttccaa aaactcaatt aacaaagcag gagctcaata tggaacaggt     540
tattgtgatg cacaatgtcc acatgacatg aaattcatta tggagaagc caatgttttg     600
gattggaaac acagtcaaa cgatgagaac tcaggtaatg gacgatatgg agcttgctgc     660
acagaaatgg atatttggga agccaattca atggcaacag cttatacacc acacgtttgc     720
acagttactg gacttcgcag gtgtgaggga acagagtgtg gagatacaga tgcaaatcaa     780
cgatacaatg gaatttgtga taaagacggg tgtgacttca actcgtatcg gttaggtgac     840
aagactttct ttggagttgg aaagacagtt gactcaagca gccagttac agttgttaca     900
caatttgtca ccagcaatgg tcaagactca ggaacattgt cagaaatccg aagaaagtat     960
gttcaaggtg gtaaagtaat tgaaaattct aaagtcaaca ttgcaggaat aacagcaggt    1020
aactcagtta ctgatacatt ctgtaatgaa cagaagaaag catttggaga taataatgat    1080
tttgagaaga agggaggatt aggagcatta agcaaacaac ttgatgctgg aatggtttta    1140
gttttatcat tgtgggacga tcattcagtt aacatgttat ggcttgattc aacatcccca    1200
actaatgcag cagccggagc tttaggaaca gaacgaggag cctgtgctac ttcatctggt    1260
gcaccctctg atgttgagtc tcaatcacct gatgctacag ttactttctc agacatcaag    1320
tttggaccaa ttgattcaac ttactaa                                         1347
```

<210> SEQ ID NO 68
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
atgcttgcat cattacttcc cctctccaac tcactgggga cagcatctaa tcaggcagaa      60
acacatccaa agttaacatg gactcaatac actggtaaag gtgcgggaca aactgtaaat     120
ggagaaattg ttctcgattc gaactggcga tggactcaca aggatggaac aaaattgttat     180
gatggaaaca catggtcatc atctttgtgt ccagatccaa caacatgttc caacaactgc     240
aatcttgatg gagcagatta tccaggaact tatggaatca ccaccagtgg aaatcaattg     300
aaacttggat tgttactca tggctcatat tcaactaaca ttggttcaag agtttactta     360
```

```
ttaagagatt cgaagaatta tcaaatgttc aagctgaaga acaaagaatt cacatttaca    420
gttgatgatt ccaagcttcc atgtggacta atggagctg tatatttcgt tgccatggat     480
gaagatggag gtactgcaaa acacagcatt aacaaagcag gagctcaata tggaacgggt    540
tattgtgatg ctcaatgccc acatgatatg aagttcatca atggagaggc aaatgttttg    600
gattggaagc cacagtctaa tgatgaaaat tcaggaaatg gacgatgggg tgcccgctgt    660
actgaaatgg atatttggga agccaattca cgcgcaacag cttacacacc gcacatttgc    720
acgaagacag gtctttacag gtgcgagggg acagaatgtg gagatagtga caccaatcga    780
tatggaggag tttgtgataa agatggttgt gattttaatt cttaccgaat gggtgataaa    840
tcattctttg gacaaggtaa aacagttgac agcagcaagc cagttacagt tgttacacaa    900
ttcatcactg ataataatca agattcgggt aaattaactg agattcgaag aaaatatgtt    960
caaggaggaa aagttattga taattccaaa gttaatatcg ctggtatcac cgcaggcaat   1020
ccgatcactg atacattttg tgatgaagcc aagaaagcat ttggagataa caatgatttt   1080
gagaagaaag ggggtttaag tgctttgggt actcaacttg aggctggttt tgttttagtt   1140
ttgtctttat gggatgatca ctcagttaat atgttgtggc ttgattccac ttatccaacc   1200
aatgcaagtc ccggagcttt aggtgttgaa cgtggtgatt gcgcgattac gtcaggtgtt   1260
ccagctgatg ttgaatccca gtctgctgat gcctctgtta cgttttctga tattaaattt   1320
gggccaatcg attcaacgta ctaa                                          1344

<210> SEQ ID NO 69
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
atgattttag cacttcttgt tcttggaaaa tctcttggta ttgcaaccaa ccaagcagaa     60
actcatccaa agttaacatg gactcgatat caatcaaaag gatcaggttc aacagttaac    120
ggagaaattg ttcttgattc taactggagg tggactcatc attcaggaac caactgttat    180 gatgaaata catggtcaac atcactttgt ccagatccaa caacatgttc aaacaattgt    240
gaccttgatg gagcagatta tccaggaact tatggtattt ctacatcagg aaattcattg    300
aaacttggct tgttacaca tggatcatat tcaacaaata ttgggtcaag agtttacttg    360
ttacgtgatt ctaaaaatta tgaaatgttc aaacttaaga ataaggagtt taccttcaca    420
gttgatgatt ctaaacttcc atgtggattg aatggagctt tatactttgt tgcaatggat    480
gaagatggag gagttttctaa aaactcaatt aacaaagcag gagctcaata tggaacaggt    540
tattgtgatg cacaatgtcc acatgatatg aaattcatta atggagaagc caatgttttg    600
gattggaaac cacagtcaaa cgatgagaac tcaggtaatg gacgatatgg agcttgctgc    660
acagaaatgg atatttggga agcaaattca atggcaacag cttatacacc acacgtttgt    720
acagtcactg gacttcgcag gtgtgaagga acagagtgtg gagatacaga caatgatcaa    780
cgatacaatg gaatttgtga taagatgggt gtgacttca actctatatcg attaggtgat    840 aagagttttct ttggagttgg aaagacagtt gactcaagca aaccagttac agtggttaca    900
caatttgtca ccagcaatgg acaagactca ggaatattat cggaaactcg aagaaagtat    960
gttcaaggag gtaaagtaat tgaaaattct aaagttaacg ttgcaggaat aacagcaggt   1020
```

```
aactcagtta ctgatacatt ctgtaatgag cagaagaaag catttggaga taataatgat    1080
tttgagaaga agggaggatt aggagcatta agcaaacaac ttgatgctgg aatggtttta    1140
gttttatcat tgtgggacga tcattcagtt aacatgttat ggcttgattc aacatacccca   1200 actaatgctg cagcaggagc tttaggaaca gaacgaggag cctgtgccac ctcatctggt    1260
aaaccttctg atgttgagtc tcaatcacct gatgctacag ttaccttctc agacatcaag   1320
tttggaccaa ttgattcaac ttactaa                                        1347
```

<210> SEQ ID NO 70
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
atgattttag cacttcttgt tcttggaaaa tctcttggta ttgcaaccaa ccaagcagaa      60
actcatccaa agttaacatg gactcgatat caatcaaaag gatcaggttc aacagttaac     120
ggagaaattg ttcttgattc taactggagg tggactcatc attcaggaac caactgttat    180
gatggaaata catggtcaac atcactttgt ccagatccaa caacatgttc aaacaattgt    240
gaccttgatg gagcagatta tccaggaact tatggtatt  ctacatcagg aaattcatta    300
aaacttggct ttgttacaca tggatcatat tcaacaaata ttggatcaag agtttactta    360
ttaaaagata caaagagtta tgagatgttc aaacttaaga ataaggaatt taccttcaca    420
gttgatgatt ctaaacttcc atgtgggttg aatggagctt tatactttgt tgcgatggat    480
gaagatggag gagtttctaa aaactcaatt aacaaagcag gagctcaata tggaacaggt    540
tattgtgatg cacaatgtcc acatgacatg aaattcatta tggagaagc caatgttttg     600 gattggaaac cacagtcaaa cgatgagaac tcaggtaatg gacgatatgg agcttgctgc    660
acagaaatgg atatttggga agccaattca atggcaacag cttacacacc ccacgtttgc    720
acagtcactg gacttcgcag gtgtgaagga acagaatgtg gagatacaga caatgatcaa    780
cggtacaatg gaatttgtga taaagatggg tgtgacttca actcatatcg attaggtgat    840
aagagtttct ttggagttgg caagacagtt gattcaagca aaccagttac agttgttacc    900
caattcgtca ccagcaatgg acaagactca ggaacattat cggaaatccg aagaaagtat    960
gttcaaggag caaagtaat tgaaaattct aaagttaacg ttgcaggaat aacagcaggt     1020
aactcggtta ctgatacatt ctgtaatgag caaagaaag catttggaga taataatgat    1080
tttgagaaga agggaggatt aggagcatta agcaaacaac ttgatgcagg aatggtttta    1140
gttttatcat tgtgggacga tcattcagtt aacatgttat ggcttgattc aacatatcca   1200
acaaatgctg cagcaggagc tttaggaaca gaacgaggag cctgtgccac ctcatctggt    1260
aaaccttctg atgttgagtc tcaatcgcct gatgctacag ttaccttctc agacatcaag   1320
tttggaccaa ttgattcaac ttactaa                                        1347
```

<210> SEQ ID NO 71
<211> LENGTH: 1320
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
atgctttgta ttggattaat tagttttgtt tattcgttag gagttggtac gaatacagca      60
gaaactcatc cgaaattgac atggaaaaat ggaggacaaa cagtgaatgg agaagttaca     120
gttgattcta attggcgttg gactcatact aaaggaagta ctaagaattg ttatgatggt     180
aatctttgga gcaaagatct ttgtccagat gcggcgacat gtggtaagaa ttgtgtttta     240
gagggagcag attattcagg tacatatgga gttacatcaa gtggtaatgc attaacattg     300
aaatttgtaa cgcatggatc gtattctact aatgttggtt ctcgtcttta tcttctgaaa     360
gatgaaaaga catatcaaat gttcaattta aatggcaagg aatttacatt tacagttgat     420
gtttctaatc ttccatgtgg tttgaatggt gctctttatc atgttaacat ggatgaagat     480
gggggcacga aacgttatcc agataatgaa gcaggtgcta aatatggaac aggttattgt     540
gatgcacaat gtccaacaga tcttaaattc attaatggta ttcctaatag tgatggttgg     600
aaaccacaaa gtaatgataa gaattccgga aatggtaaat atggatcatg ttgcagtgaa     660
atggatattt gggaagctaa ttcgatttgt tcagcagtta ctccacatgt ttgtgacaat     720
cttcaacaaa ctcgttgtca aggcacagcc tgtggtgaga atggaggagg tagtcgattt     780
ggtagttcat gtgatccaga tggttgtgat tttaactcat ggagaatggg aaacaaaaca     840
ttttatggtc ctgggttgat tgttgatact aagtcgaagt ttacagttgt aacacaattt     900
gtcggcaacc cagttacgga aattaagaga agtatgttc aaaatggaaa agtaattgaa     960
aattcatatt caaatatcga aggaatggat aagtttaatt ctgtttcaga taagttttgt    1020
actgctcaaa agaaagcttt tggtgatact gatagcttta ctaagcatgg tggcttcaaa    1080
caacttggtt ctgctcttgc taagggaatg gtccttgtct tgtcactttg ggatgatcat    1140
actgtcaaca tgctttggtt ggattccgta tatccaacaa attcaaagaa agctggtagt    1200
gaccgtggtc cttgtcctac tacttctggt gttcctgctg atgtcgaatc aaaaagtgca    1260
gatgcaaatg tcatatattc tgacattcgt tttggtgcaa ttgattcaac ttacaaataa    1320
```

<210> SEQ ID NO 72  
<211> LENGTH: 1320  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 72

```
atgctttgta ttggattaat tagttttgtt tattcgttag gagttggtac gaatacagca      60
gaaactcatc cgaaattgac atggaaaaat ggaggacaaa cagtgaatgg agaagttaca     120
gttgattcta attggcgttg gactcatact aaaggaagta ctaagaattg ttatgatggt     180
aatctttgga gcaaagatct ttgtccagat gcggcgacat gtggtaagaa ttgtgtttta     240
gagggagcag attattcagg tacatatgga gttacatcaa gtggtaatgc attaacattg     300
aaatttgtaa cgcatggatc gtattctact aatgttggtt ctcgtcttta tcttctgaaa     360
gatgaaaaga catatcaaat gttcaattta aatggcaagg aatttacatt tacagttgat     420
gtttctaatc ttccatgtgg tttgagtggt gctctttacc atgttaacat ggatgaagat     480
gggggcacga aacgttatcc agataatgaa gcaggtgcta aatatggaac aggttattgt     540
gatgcacaat gtccaacaga tcttaaattc attaatggta ttcctaatag tgatggttgg     600
aaaccacaaa gtaatgataa gaattccgga aatggtaaat atggatcatg ttgcagtgaa     660
atggatattt gggaagctaa ttcgatttgt tcagcagtta ctccacatgt ttgtgacaat     720
cttcaacaaa ctcgttgtca aggcgcagcc tgtggtgaga atggaggagg tagtcgattt     780
```

```
ggtagttcat gtgatccaga tggttgtgat tttaactcat ggggaatggg aaacaaaaca    840 tttatggtc ctgggttgat tgttgatact aaatcgaagt ttacagttgt aacacaattt    900
gtcggcaacc cagttacgga aattaagaga aagtatgttc aaaatggaaa agtaattgaa    960
aattcatatt caaatatcga aggaatggat aagtttaatt ctgtttcaga taagttttgt   1020
actgctcaaa agaaagcttt tggtgatact gatagcttta ctaagcatgg tggcttcaaa   1080
caacttggtt ctgctcttgc taagggaatg gtccttgtct tgtcactttg ggatgatcat   1140
actgtcaaca tgctttggtt ggattccgta tatccaacaa attcaaagaa agctggtagt   1200
gaccgtggtc cttgtcctac tacttctggt gttcctgctg atgtcgaatc aaaaagtgca   1260
gatgcaaatg tcatatattc tgacattcgt tttggtgcaa ttgattcaac ttacaaataa   1320
```

```
<210> SEQ ID NO 73
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
```

```
atgcttggga ttggatttgt ttgcattgtt tactcattgg gagttggaac gaatacagcg     60
gagaatcatc cgaagttgac atggaagaat tcaggttcaa caacgaatgg tgaagttaca    120
gttgattcta attggcgttg gactcacacg aaaggcacaa cgaagaactg ttatgatggt    180
aatctttgga gcaaagatct ttgtccagat gcagcaacat gtgggaagaa ttgtgttctt    240
gaaggagcag attattcagg tacatatgga gttacatcga gtggtgatgc attaacactt    300
aaatttgtta cacatggatc atattcaacg aatgttggat ctcgtcttta tttattgaaa    360
gatgagaaaa catatcagat cttcaatttg aatgggaaag aattcacatt cacagttgat    420
gtttctaatc ttccatgtgg tcttaatgga gcactttact ttgtgaacat ggatgcagat    480
ggaggtacag gacgttatcc agataaccag gcaggtgcta agtatgggac aggttattgt    540
gatgcacaat gtccaacaga tttgaaattc atcaatggga tccctaactc agacggttgg    600
aaaccacaaa gcaacgataa gaactcagga atgggaaat atggatcatg ttgtagtgaa    660
atggatattt gggaagctaa ttcacttgca acagcagtta cacctcatgt ttgtgaccaa    720
gttggacaaa ctcgttgtga aggaagagcc tgtggtgaga atggaggagg tgatcgattt    780
ggtagttcat gtgatccgga tggctgtgac ttcaattcat ggaggttggg caacaaaacg    840
ttctggggtc caggactgat tgttgataca aagaaaccag ttacagttgt cactcaattt    900
gttggcagcc cagtcaccga aatcaagcga agtatgtgc aaggtggaaa agtaatcgag    960
aattcataca caaacatcga gggtttggat aaatttaatt caatctcaga taagttctgt   1020
actgctcaga agaaagcttt tggtgataat gacagtttca taaagcacgg cggcttcaga   1080
caattgggtc aatcttttac aaaaggtcag gttttggtac tttcactttg ggatgatcat   1140
actgtcaata tgctttggtt ggattctgta tatccaacaa attcaaagaa accaggtgca   1200
gaccgtggac cttgtcccac ctcgtctggt gttcctgctg atgttgaatc aaagaatgct   1260
ggttcaagtg tcaaatattc tgatattcgt tttggatcaa ttgattcaac ttacaaatag   1320
```

```
<210> SEQ ID NO 74
<211> LENGTH: 1077
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 74

```
atgatcgttg ctttgattgc tcttgtcact ggagcaacac ttgttgaaac aaagcccgtt      60
gtcaaatggc aaaaatgtac gaaatctggt tgtacaacag tgactggttc agtcactact     120
gactttgaat ctcgtggaga gaaaaaatcg gatcataccg cagccgttga ttatgttcaa     180
caacttgggg ttgaatcaac aggcgatatg cttagtcaga agcttgtcac aatatacaat     240
gggaaaaaga acgtcgggtc tcgtctttat ctccttgatc ctactggtga aaagtatcaa     300
atgtttattt tagttaacca tgaattcact tatactgttg atctttctga atgtccttgt     360
ggtatgaatg ctgccattta tacgtcagag atggctgctg aaggtgctgg tctcggtcct     420
aaatttggac aaggttattg tgatgcaaac tacgttggag ttgatgaacg tggatgtgcc     480
gagtttgata ttatggaagc taatactcgt gccattacat tcacgactca tccatgttca     540
aaactgaaac aaaatgttaa gaatacagtc cagtgtatgc ctgatggttg cggttttaat     600
gcataccgat atggtggtag aaccttctac ggccctggtg ctacatataa agttgattca     660
acaaagaaga ttaccgtggt cacccaattt atatcaagtg atggaactga taaaggtgat     720
cttgttgaga ttcgtagatt gtacgttcaa ggtggaaaag tcattcctaa tgcgaaggtt     780
tctgtgtata attcaggtga attcgattct atcagtgaca aattctgtag aacagctgga     840
catcagattg atggatatca tgcgttgtct ttcatggggc agtctttcaa gaatggccac     900
gcacttatct tctcattatg ggatgcaaat gatggaatga catggttgga tgcaggtgag     960
tacgggccat gccccggaag tccagctgaa acgggtgcgg caattgaagc cgcgcatcct    1020
aatcttcggg tatattggtc aggaatcaaa tatggtgatc ttgattccac gtactaa       1077
```

<210> SEQ ID NO 75
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
atgcttgtct ttgggattgt tagttttgtt tattccatcg gggttggtac gaatacagcg      60
gagactcatc cgaagttaac atggaagaat ggaggttcaa caacgaatgg agaagttaca     120
gttgattcta attggcgttg gactcatacg aaagggagca ctaagaattg ttatgatggt     180
aatctttgga gcaaagatct ttgtcctgat gcagcgacct gtggtaagaa ttgtgttctt     240
gaaggagcag attattcagg tacttatgga gttacatcga gtggtgatgc attaacactt     300
aaatttgtta cacatggatc atattcaacg aatgttggtt cacgtcttta tcttcttaaa     360
gatgagaaaa catatcagat gttcaatttg aatgggaaag aatttacatt tacagttgat     420
gtttcacagc ttccatgtgg tcttaatggt gcactttatt ttgtttgtat ggaccaagat     480
ggtggcatga gtcgttatcc agataaccaa gcaggtgcta atatggaac tggttattgt      540
gatgcacaat gtcctactga tcttaagttt attaacggcc tcccaaactc agacggttgg     600
aaaccacaaa gtaacgataa gaattcaggg aatggtaaat atggatcatg ttgtagtgaa     660
atggatattt gggaagcaaa ttcacttgca actgctgtta ctcctcatgt ttgtgaccaa     720
gttggtcaaa cacgttgtga aggaagagca tgtggtgaga atggtggtgg tgatcgattt     780
ggtagtattt gtgaccctga tggttgtgac tttaactcct ggagaatggg taacaagact     840
```

-continued

| | | |
|---|---|---|
| ttctggggtc ctgggctgat tattgataca agaaaccgg ttactgtcgt cacacaattc | 900 |
| attggttctc ctgttactga aatcaagaga gaatatgttc aaggtggaaa agtaatcgaa | 960 |
| aattcatata caaatatcga gggaatggat aaatttaatt ctatttcaga taagttttgt | 1020 |
| actgctcaga aaaagctttt cggtgataac gacagtttca caaagcacgg tggtttcagc | 1080 |
| aaattgggtc aatcatttac aaagggtcag gttttggtac tttcactttg ggatgatcat | 1140 |
| actgttaata tgctttggtt ggattctgta tacccaacta actctaagaa actcggttcg | 1200 |
| gaccgtggac cttgtccaac ttcatcaggc gtccctgctg atgttgaatc caagaatgct | 1260 |
| gattcaagtg tcaaatattc tgatattcgc tttggatcaa tcgattcaac ttacaagtag | 1320 |

<210> SEQ ID NO 76
<211> LENGTH: 1338
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

| | | |
|---|---|---|
| atgctttgtg ttggattgtt tggacttgtt tattcaattg gtgttggaac taacactcaa | 60 |
| gaaacacatc ctaaattgag ttggaagcaa tgtagttcag gtggttcatg tacaactcaa | 120 |
| caaggttcag ttgttattga ttctaattgg cgttggactc attctactaa agatttaacg | 180 |
| aattgttatg atggtaatct ttgggatagt acattatgtc cagatggtac tacttgttca | 240 |
| aagaattgtg ttcttgaagg tgcagattat tcaggaacta tggaattac atcaagtgga | 300 |
| gattctttaa ctttgaagtt tgtgactcat ggatcatatt ctacaaatgt tggttctcgt | 360 |
| ctttatcttc taaaagatga taataattat caaatattta atttagcagg caaagaattt | 420 |
| acatttacag ttgatgtttc taatcttcct tgtggtttga atggtgcatt atattttgtt | 480 |
| gaaatggatc aagatggtgg taaaggaaaa cataaagaaa atgaagctgg tgctaaaatat | 540 |
| ggaacaggtt attgtgatgc tcaatgtcca acagatctta aattcattga tggtattgct | 600 |
| aacagtgatg gttggaaacc tcaagataat gatgagaatt caggaaatgg taaatatggt | 660 |
| tcatgctgta gtgaaatgga tatttgggaa gctaattcac ttgctacagc ttatactcct | 720 |
| catgtttgtg atacaaaagg tcaaaaacgt tgccaaggta ctgcttgtgg tgaaaatggt | 780 |
| ggtggtgatc gttttggaag tgaatgtgat ccagatggtt gtgactttaa ttcatggaga | 840 |
| caaggaaaca gagtttctg ggcccagga ttgattattg atacaaagaa atcagtacaa | 900 |
| gttgtaactc aatttattgg aagtggaagt tcagtaactg aaattcgtcg taagtatgtt | 960 |
| caaaatggaa aagttattga aaactctat agtactattt caggtactga aaagtacaat | 1020 |
| tcaataagtg atgattattg caatgcacaa aagaaggctt tcggagatac taatagcttt | 1080 |
| gagaatcatg gtggattcaa gagatttagt caacatattc aagatatggt acttgtactt | 1140 |
| tcgctttggg atgatcatac tgtaaatatg ttatggttgg attcggttta tccaactaac | 1200 |
| tcgaacaagc ctggtgctga tcgtggacct tgtgaaactt cttctggtgt tccagctgat | 1260 |
| gttgaatcca atctgctag cgcaagcgtt aagtattctg atattcgctt tggtccaatt | 1320 |
| gattcaacct ataagtaa | 1338 |

<210> SEQ ID NO 77
<211> LENGTH: 1320
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
atgctttgta ttggattaat tagttttgtt tattcgttag gagttggtac gaatacagca    60
gaaactcatc cgaaattgac atggaaaaat ggaggacaaa cagtgaatgg agaagttaca   120
gttgattcta attggcgttg gactcatact aaaggaagta ctaagaattg ttatgatggt   180
aatctttgga gcaaagatct ttgtccagat gcggcgacat gtggtaagaa ttgtgtttta   240
gagggagcag attattcagg tacatatgga gttacatcaa gtggtaatgc attaacattg   300
aaatttgtaa cgcatggatc gtattctact aatgttggtt ctcgtcttta tcttctgaaa   360
gatgaaaaga catatcaaat gttcaattta aatggcaagg aatttacatt tacagttgat   420
gtttctaatc ttccatgtgg tttgaatggt gctctttatc atgttaacat ggatgaagat   480
gggggcacga aacgttatcc agataatgaa gcaggtgcta aatatggaac aggttattgt   540
gatgcacaat gtccaacaga tcttaaattc attaatggta ttcctaatag tgatggttgg   600
aaaccacaaa gtaatgataa gaattccgga atggtaaat atggatcatg ttgcagtgaa   660
atggatattt gggaagctaa ttcgatttgt tcagcagtta ctccacatgt ttgtgacaat   720
cttcaacaaa ctcgttgtca aggcacagcc tgtggtgaga atggaggagg tagtcgattt   780
ggtagttcat gtgatccaga tggttgtgat tttaactcat ggagaatggg aaacaaaaca   840
ttttatggtc ctgggttgat cgttgatact aaatcgaagt ttacagttgt aacacaattt   900
gtcggcaacc cagttacgga aattaagaga agtatgttc aaaatggaaa agtaattgaa   960
aattcatatt caaatatcga aggaatggat aagtttaatt ctgtttcaga taagttttgt  1020
actgctcaaa agaaagcttt tggtgatact gatagcttta ctaagcatgg tggcttcaaa  1080
caacttggtt ctgctcttgc taagggaatg gtccttgtat tgtcactttg ggatgatcat  1140
actgtcaaca tgctttggtt ggattccgta tatccaacaa attcaaagaa agctggtagt  1200
gaccgtggtc cttgtcctac tacttctggt gttcctgctg atgtcgaatc aaaaagtgca  1260
gatgcaaatg tcatatattc tgacattcgt tttggtgcaa ttgattcaac ttacaaataa  1320
```

<210> SEQ ID NO 78
<211> LENGTH: 1023
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

```
atgttcaagg tgatagtcaa ggtgatagta gctttgtatt gtcttcacgc tgtcgctgct    60
ggtgaacaga gaccacagtg gacttgggaa cttgatggaa aggctgtcac gagccttata   120
acacaagata ctgtctcccg tggaacaaca ggaaaaggtg atattgacta caatgcgact   180
ggtgttttg tttctgagga tggcaaaacg ctcactcaga ggatgagaac tatgaccaca   240
tgggagaata atggggctc tcgtctttat ttactcaatg ctgatttgca gaattatgag   300
attgttgacc ttaaggggaa agagctgtca tttgatgttg atatgtctgc tctgccctgc   360
agcattaacg cggccctgta cacagtggaa atgccgaagg tggtgccgcg gaatgacgct   420
caatatggaa caggatattg tgatgcacaa gggtccgggt ccggtgcttg caacgagctt   480
gatatttggg aagcaaacag tgcagcaacg caacttgcag ttcatgcatg cacacctgca   540
ggccgtggag gaacgtgcga ctcaggggggt tgcaatgaca atccgtacag gactgataag   600
actttctacg gttcatcaga gaaatttact ttggacactt ccaaaccgtt taccgtagtt   660
```

```
actcagtttg tgaccagcgg tggtgctttg acggaagtca tccggaagta tgtgcagggc    720
ggaaagacca tccccacacc tccagtcact gctggcggaa ccgagtacac gtccctcacg    780
aacccgttct gcgctgcgac cggcgcgaag ccgcttgatg gcatgtctac ttctctggac    840
gccggccacg tggtggtggt ttcgctgtgg gcatcggacg atgctggggg aatggactgg    900
ctggacagtg gaacaacgg gccgtgcgct gcgaacgatc ctgacggagc aagggagcag    960
ctgatcaaga agtatccgga tgcactggtc aaatattcga atttgaagat caccacgttg   1020
tag                                                                 1023
```

<210> SEQ ID NO 79
<211> LENGTH: 1026
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
atgtttaagg tgttagtcaa agtgacaatt gctttgtttt gtcttcatgc tgtcgctgca     60
ggggaacagc ggccaaagtg gacatgggaa cttgatggaa aagctgtaac gagccttata    120
actcaagata ctgtctcccg cggaacaaca ggaaaaggtg atattgacta caatgcgact    180
ggtgttcttg tctctgagga tggcaaaact ctcactcaga ggatgagaac tatgaccaca    240
tgggaaaata aatggggctc tcgtttgtat ttactcaacg ctgatggaca gaattatgag    300
atggtcgacc ttaagggcaa agagttagca tttgatgttg acatgtctgc tctgccctgc    360
agcattaatg ccgccctgta caccgtggaa atggcgaagg tggtgcctc aaatgatgct    420 cagtatggaa caggatattg tgatgcacaa gggtccgggt ccggcgcctg caatgagctc    480
gacatttggg aagcaaacag tgcagcaacg caacttgcag ttcattcttg cacacctgct    540
ggccgtggag aacgtgcga cacagggggt tgcaatgaca atccgtacag gactgataag    600
actttctacg gttcatcaga gaaatttgct gttgacacct ccaaaccatt taccgtagta    660
actcagtttg tgaccggtgc cggtggtgcg ttgactgagg tcatccgtac gtatgtgcag    720
ggtggaaaga ccatccccac tcccgcagtc actgctggcg gcaaccaata cacatccctc    780
acgaacgcgt actgcagcgc ttcaggcggg aaaccgcttg atggcatgag cacgtccctg    840
gacgctggcc acgtgatagt ggtttcgctg tgggcatcgg acgatgcagg gggaatggac    900
tggctggaca gtgggaacaa cggaccgtgc gctgcgaacg atcctgacgg agcaagggag    960
cagctgatca agaagtaccc tgaggcactg gtcaagtatt cgaatttgag gatcaccacg   1020
ttgtaa                                                              1026
```

<210> SEQ ID NO 80
<211> LENGTH: 997
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
atgatgaaag caacaatcat tttgctgttt ctgattttgc atgcagcaga taaaaacgtt     60
cccaaactca aatggataaa tgatggtgtt gaagtgacaa gcacaataac tcaggacact    120
gtttctcgtg gaactacagg aacagggggat atagattata attctactgg agtgtatgct    180
tctgaagatg ggaagagtct tacccaaaga atggacactg ttaccacatg ggaaaacgaa    240
```

```
tggggctctc gtctttattt actcaatgca gatggagcaa attatgaaat tgtttatcta    300
aagaacaaag aggtgtcttt tgatgttaac atgtccactt tgccatgttc tatcaatgct    360
gctttgtaca cagtggaaat gccaaaagca ggaagtgaca aaggcgcaca gtatgggact    420
ggttattgcg atgctcaggg tggaagtgat gggtgtaatg aaatggatct ttgggaagcg    480
aatagtgcag caacgcagct tgcggtgcat tcatgcagtg gcgggagctg tgacactggt    540
ggatgcaatg tcaatccgta cagaactgac actggatatt atggctctgg ggagaaattt    600
actgttgata catcaaaagt gtttactgtt gttactcagt ttttgactga tgccagtgga    660
gctctatcgg aagttcgccg cagctatatt caaaacggga aaacaatccc cacaccccg    720 gtggaagctg ggggcaagac gtatgactcc atcacagacc cgtactgtgc ggcaaccaac    780
gcgaggtcgc tggcagggat ggatgcgtcg ctggacaagg gtcacgttgt cgtgatttcg    840
ctctgggcgt ctgacgacgc gggtggaatg gactggctag attctggtaa caacggacct    900
tgccaagcga acgacccaca gggtgcgagg aagcaacttg tgaaggctta tcccaacgcg    960
ctggtggtgt attccaattt ggtggtgaaa tcactgg                             997

<210> SEQ ID NO 81
<211> LENGTH: 1023
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
atggcatttg cgtgtgtatt gtttattgca tttctaagtg ctgaaacacg accaaaactc     60
gaatggacta aaaatggaca gaaggtaaca agctcgctta caacagataa catttggcgt    120
gctgacaaaa gaactgctga ttttaactac acggaatatg gagtcacaac cagcggaaat    180
gaaattagac aaaaactgct caataaccat ccttcaggaa atcctacttc aggatctcgc    240
gtgtatctct tgaacgagaa tgatttgcag tacgaaatgt ttaatttgaa tggcaacgaa    300
tttaccttcg atgtggatac aagccaaatt ccttgcggac tggcaggaac attgtttact    360
gtggaaatgg cgcgtaatgg gacaggaggt ggaggtacaa caggagctga atatggctgt    420
ggctattgtg atgcacaatt tttaggagcg actgatgaag atgggcacca gggagtgggc    480
tgtgcggagt ttgatttctg ggaagctaac aggtattcga ccttagtaac cgcgcacgca    540
tgttccacaa cggggcagtt gggagggagc aatggtaaag gcagttgcga ctcaaacgga    600
tgtggctaca acacatattg ggataataag aacttctacg gaccgggatc gtcctacaca    660
attgacacca cgaagaagtt tactgtcacc acacagtttg tcacgagcgg aggatcactc    720
acggagatca gacggaaata cattcagaat gggaagagct ttgacagccc aggtgcactt    780
gatgccaaaa gatgcaataa taatgactac ccgctgtcta agatgggca gtcctttgag    840 aagggacacg tgatcgtatt tgccttgtgg gacagcgaca gtggactggc gtggcttgat    900
tcaggcagcg ctggcccgtg cacggactcg gagtcggcat cttatgtgga gtcgcattat    960
tccgacgcga cgatcatctt ctccaacatc cgattcggtc gattgactc gacgacaagt   1020 tcc                                                                1023

<210> SEQ ID NO 82
<211> LENGTH: 1008
<212> TYPE: DNA
<213> ORGANISM: Artificial Sequence
<220> FEATURE:
```

<223> OTHER INFORMATION: Description of Artificial Sequence: Synthetic
    polynucleotide

<400> SEQUENCE: 82

```
atgtttgcag ttgcagcggc ttttatttg tttgtttccc tgttcgcggt tgatgactat      60
ccaatattaa gttgggagag gaatggaaaa accattcagg gccgaattgt tgtcgacttg     120
aattggaggg gcgaaaatca cacgaacgag atagattaca agaacattgg tgtttggacg     180
gaaggaaacg ctctcaacca gcgccttgtg acggtcaatc catggggcaa cacggtagga     240
cagcgcttgt atttgctggc tgaagaagga gataactatg aacttttaga cttagttggc     300
agtgagctga cgtacgacgt agatatttct caaattccat gcggactgaa cgcagcgctt     360
tatactgtcg aaatggcgcc tggggagcg aaagcaccag aagttggggc gcgtatgga       420
tctggctact gtgatgctca gttcttagga gcagatgacc ttggatgtgg agaatttgat    480
atttgggaag caaaccgagc cgctacagtt tataccacac atgcgtgcac tcagactggc    540
caattcgcaa aggcagcgc tacgtgtgac tcaaacggct gtggttacaa ttcgtaccgc      600
gatagtaacg aacataactt ctacggaaat gcatcctcct tcactgtgga ttcttcgaaa    660
cccttcacgg tcatcaccca attttgtct tcaggaggtg cattgacgtc tgttgtgcgc     720
aagtacattc agaatggaag aacaatcaca agcacgggtg cgcttgacgg gaacaggtgc    780
actagcagtc agtacagtct ggcacagatg gggaagtcgc tctctaatgg acacgttctc    840
gcttttagcc tttgggattc gtcgaacgga ctggattggc ttgatgcggg caacaatggt    900
ccgtgctctg gccaggatga gtcggctacg tacctcgaaa agaacttccc cgatgcaact    960
atcacgtggt ccaatatccg ctttggtcct attgattcca cctattag                 1008
```

<210> SEQ ID NO 83
<211> LENGTH: 1053
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 83

```
atggctgtac ttctggtgtt tgcgttttt ttttcacaaa ttttgggtga aacaaagcct       60
tcttttactt attcatacaa tgggcagtct cgttctggct atattgtggt tgatcaagag     120
tggcgaagct cagcgactgc tgacattgat tataagaata ttggagtatc aacaagtggg    180
ggctctttga ctcaaagact tgtgaccaca actggcgggc agcaggtcaa tggttctcgg    240
ctgtatttga tgtcctctgc gactaaaatat gaaacgttcg cgcttttggg agatgtagag    300
ttcacatatg atgttgatct gtctaagact gcatgtggca tgaatgctgc cttgtatacc    360
attgagatga acgcaaatgg actttctaac gatgcacaat acgggacagg ttattgcgat    420
gctcagtttt tgggtatgat taacggcaaa caatcaaatg gttgtgcaga gcttgatatt    480
atggaggcaa acaaggaagc aaatgtttgg accactcaca gttgcagctt tctgggacag   540
tctaccggtg gaagctgcag ttccgacgga tgcggcttca acgtgaacag attctgctgc   600
gctcagtccc agcagacaca cgaagacatt tgtgacttct acggatccag ttctaagttc  660
cagattgaca ctacaaagac ctttactgtg atcacacaat tcaagggcaa tcctctcaag   720
gagatcgtgc gcaagtacaa gcagggtggg aagaccattg agaaccctag ttgtgatatc   780
tggggaccta acccgcacga cagattggat gatggattct gcactgccag tgggcacagc  840
gccgacatgg ctcagatggg caagagtcta gcaagggac atgtcttgtc gtttagcttt   900
```

-continued

```
tgggacagta actccgggat gtggtggctt gaccagggtg agtatgggcc atgctcaggt    960
tccgaggatg cagcaactct ccactctaag tatccggatg caacggtgac gtggagcaat   1020
gtaaagtttg gacccctgga ttcaacgtat taa                                 1053
```

<210> SEQ ID NO 84
<211> LENGTH: 1029
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
atgtttgtcg tcttttttgtt tttctcgaat ttgtttgcgg agtcaaatcc gtctctcacg     60
tatacgtaca atggggcttc aagaacaggg tacattgtgg ttgatcagga atggagagat    120
actgcgactg cagacgtcaa ctatagcgca attggagtat cgacaagtgg aagttcattg    180
actcaggtgc ttgtcacacc aagtggagca attggaagcc gtttgtattt gcttgattcc    240
accaaatcaa gttacgagtt gtttgctttg gttggtaatg tggaattttc ttatgatgtg    300
gacatgtccg acctcccatg tggaatgaac gctgcactat acacgattga gatgaataag    360
aatggtttaa agaatgacgc acagctgggc acgggctatt gcgacgctca gttcttgggg    420
atggttgatg gaaaacaagt cagtggatgt gctgaactgg acatatggga ggcaaatagg    480
gaggctactg tgtacacaac ccatccttgc actttcacgg gtcaatctac aaaaggaagt    540
ggttcgtgcc agtcagacgg atgtggtttc aatgcttatc gttatgggga aaaaaatttc    600
tatgggcctt cctccagttt cacattggat actaccaaaa aattcacggt tgtaacacag    660
tttattggga atccgcttac cgaaatcaag aggtactata ttcagggtgg gaaaacgatt    720
cccaacgcga atcccttggt atacaacacg gccaactatg attccatcac tgatgcattc    780
tgcaagaccg ccggacacaa cccagataca aacacaaata ttgctgcgat gggaaagtct    840
ttggcgaggg gccatgtgtt gtcattttcc ctgtgggatt caaatgatgg catgggatgg    900
cttgatgctt cggaatacgg gccatgccct ggtggcactg ccgacagtgc tgcgactttg    960
gaaaagaacc atcctgggtc tcatgttgtg tggtcgaatg ttaagttcgg gccggttagc   1020
aatttgtag                                                           1029
```

<210> SEQ ID NO 85
<211> LENGTH: 957
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
atgtttgctt tggttgtact tgcaattcag ttgcttactg ctcaaggaaa tgaggctttc     60
acttattcgc tcaatggtgc tcaacaaact ggtgctatta caattgacca ggaatggcgc    120
ggcaacacca ctccaaaggc agatgtgaag ctttcaaatt ttggagtcac agtgagtgga    180
ggttcagtat cacagaaatt caagactggt actgctgtgg ggtctcgtat ttacattctt    240
gctccggggg gaacagccta tgaaaaattc aagctcgtag gtaatgttga gttgacgttt    300
gatgttgata taagccagat cccctgtgga atgaatgctg ctatttacac tgcagaaatg    360
cctgctgatg gtgttacacc tggacacgaa tctggagcag catatggtgg tggatactgc    420
gatgcgaact atgtgggagg agttggatgt gcagaattcg atattggaga atccaatgca    480
```

| | | |
|---|---|---|
| cgtgcgactg tttacacaag ccatggatgc agcccgacca ctggcttcgc gaaacagggg | 540 | |
| agcatcagtt gtgacactgg gggaacagga gcaaacccgt atcgtcagga caagaacttc | 600 | |
| tatggtaatg gctcgtcatt caccgttaat actgctcaga aattcaccgt ggtgacacag | 660 | |
| ttcaaggggt ccccagttac tactattgat cgtatctacg tccagggtgg gaaacagagc | 720 | |
| aaacaaccga caacatcaa caacaacttg atcgtatca gcccatcgtt tcggctggg | 780 | |
| catgttctga ttttctcact ctgggcttca gatggtgata tgtcctggat ggattgcaat | 840 | |
| gacaacgggc cttgcaatgc aggccaagaa tcttccagat atttggaaca gaactatcca | 900 | |
| aacgcaactg tcacgtattc aaatattaaa tatggtccgc ttgacagcac ttattag | 957 | |

<210> SEQ ID NO 86
<211> LENGTH: 957
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

| | | |
|---|---|---|
| atgtttgctc ttgttgtgct tgcaattcag ttgcttactg cccaaggaaa tgaagccttt | 60 | |
| acttattcgc tcaatggtgc tcagcagtct ggatatattg ttatcgatca agagtggaga | 120 | |
| ggcaacaata ctccgactgc ggatgtgaag ctttctgatg ctggagttac tgtcagtgga | 180 | |
| aacaccgtgt cacagaaatt caagactggt atgaatgttg ggtcgcgtat ctacattctt | 240 | |
| gctccgggtg gaaagcccta tgaaaagttc aaacttgtaa attctgagct gacttttgac | 300 | |
| gtggatattt cacagatccc atgtggaatg aatgctgcga tttacaccgc cgaaatgcct | 360 | |
| gctgatggag ttcgcctgg gcatgaggct ggggctgcat atggtggtgg atattgcgat | 420 | |
| gcaaattatg tgggaggaat tggatgtgca gagttcgata ttggagaaag caatgcgcgc | 480 | |
| gccactgttt atacaagcca tggatgtaac ccgaccactg gctttgcgag acaagggagc | 540 | |
| attagctgtg atactggggg aactggagca aacccgtatc gtcaaaacaa gaacttctat | 600 | |
| ggtaatggct cgtcattcac tgtcaatact gcctctaaat ttaccgtggt gacacagttc | 660 | |
| aaagggagtg ggcaacttac atcgattgat cgtatctaca tccaaaatgg gcaaaagatc | 720 | |
| cctcaaccaa caacatcaa caacaatttg aatcagatca gtccatcgtt ggcagctggt | 780 | |
| catgttctga ttttctcaat ctgggcttcg gatggagaca tgagttggat ggattgcaat | 840 | |
| gataatggtc cttgcaatgc aggccaggag tcttccaatt atttgcaaca aaactatccg | 900 | |
| aacgcaactg tcacttattc gaacataagg tggggaggca tagataccac ttattaa | 957 | |

<210> SEQ ID NO 87
<211> LENGTH: 957
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

| | | |
|---|---|---|
| atgtttgctt tgattctgct tgcagttcag gctttgtttg cccagggcaa cgaggcgttc | 60 | |
| acatactctg tgaacggcgc ccaaagatcg ggttacattg ttatagatca ggagtggagg | 120 | |
| ggaaacaaca ctccgactgc ggatgtgaag ctcgctaatg ctggagtcac agtgagtgga | 180 | |
| gggtcggtgt ctcagaaatt caagactgga actagtgtgg ctcccgtat ttacattctg | 240 | |
| gacccaacag ggaaagcata tgagaagttc aagtttattg atgctgagct ggcgttcgat | 300 | |

```
gtagatatca gccagattcc atgtggcatg aacgcggcga tatacactgc ggaaattcca      360
gctgatggtg ttacaccggg tcatgaggct ggagcagcat atggtggtgg ttactgtgac      420
gctaattatg tgggaggaat tggatgtgct gagttcgata ttggtgagag caatgcgcgt      480
gccactgtct acaccagcca tgggtgcaca ccgaccactg gctttgcaaa acaaggcagc      540
atcaactgcg acactggtgg cactggagcg aacccgtatc gtgctgataa gaacttctat      600
ggaaatggct catcattcac tgttaatact gcccagaaat ttaccgttgt tacacaattc      660
cgcgggtcag gccaactcac gtccattgat cgtatttaca ttcagggtgg taaacagtcc      720
aaacaaccga atagcatcac cagcaacttg gatcggatca gcccatcatt cgcggctggt      780
catgtgctga ttttctccat ctgggcttcg gatggtgaca tgtcatggat ggactgcaat      840
gacaatggtc cttgcaatgc aagccaggaa tcatcgtctt atttgcaaca gaactatcct      900
aatgcgactg ttacatacag caacatcaag gttggcccta ttggcagcac tttctaa        957

<210> SEQ ID NO 88
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
atgtttgtgc ttgtgtccct tgcgcttgcg gcgaacgcca cggaggtgca tccgaagttc       60
atctggaaga agtgtacgaa ggctggctgc accaacgtca acggtttcct tgtccatgac      120
aagcatctcg aggggggcac gtggcatcgt ggcggtgagc agctcgacta cgagaaggag      180
gtcggcgtcg tgacaaatgg cggcaccgtt tcgcagcggc tgatgagcac ctacaagggc      240
gcgaaggtca cgggttccag gatctacatc ctggaagaga cgacaagca gtacgaggag       300 ttcaagttgg tcgggaagga gctgagctat accgtcgaca tgagtcagat cccgtgcggc      360
gtgaacgcgg cgctgtacac ttcggagatg ccgcagagcg gcaagaagac aagcgaggat      420
ccattcggcc cagaaggcgg cactgggtac tgcgatgcaa actgcgtcga tggcgactgc      480
tgcccagaat tcgacatcca ggaagcttcg tcaaaggcga tggtcttcac cgcccactgc      540
tgcgagtcaa agacacactg cgatacatcg gggtgcggct acaacccata tcgcgacagc      600
ggcgacagga cgttctgggg cggaacggtc aacgtcaact cgcccgtgac agttgtcaca      660
cagttcgtcg gaagtggaac cctcaccgag atcaagaggc tttacgtcca gggaggaagg      720
gtcgtcaagg cagcgcagtc cctcaacgac gtcttctgca agtggggatc ggggcaattc      780
gcccagtact cgatggcaaa gatgggagcc tccttccaga gaggccatgt cctcgtcttc      840
tcactctggg caagcgacgg catgagctgg atggacggcg gaaatgccgg gccgtgcagg      900
agctacaacg tcgcctcgat caaggcgagc cagccgaact tgaaggtcac ctggtcaaac      960
gtcaagtttg gcgacattga ctcgacctac taa                                  993

<210> SEQ ID NO 89
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
atgtttgtag tccttgcttg tttggtcttc agtgctgaga ctcatccgaa gtttcaatgg       60
```

```
aagaagtgta cgaaggcagg ctgtactact gtcaatggct tcttggttca tgataagcac      120
attgaaggtg gacttggca tcgtggtggt gatcaacttg attacgcgaa tgaagttggt       180
gtggttgtta gtggtggcac ggtttcgcaa cgacttgtca gcacttacaa gggcagcaaa      240
attactggtt ctcgtattta cattatgact gaggatgaaa agtattacga agagtttaag      300
tttgttggca aggagttgag ctacacagtt gacatgagtc aaattccttg tggtgtaaat      360
gccgctctct atagttcaga aatgccctac aatggaaaga agacaactga cgatcctttt      420
ggtgccgaag gtgggacagg gtattgtgac gctaactgtg ttgatggaga ttgttgccca      480
gagtttgata ttcaggaagc atcctctcat gctatggtgt tcactgctca ttgctgtgag      540
agcgcgaagc attgtgacac aagtggctgt ggttacaatc cttaccgtga tagcaaggac      600
tatactttct ggggtggaac tattaacgtg aattcgccag ttactgttgt gactcagttc      660
gttggagtgg gttcgacttt gagcgaaatt aggaggcttt acgttcaggg tggacgaaca      720
attaaggcag cacagtcatt gaatgatgcg ttctgcaagt ggggtggtgc tggtcagaat      780
gctgcttatt caatggcaaa aatgggtgca agtttccaga agggacatgt catcgtgttc      840
tcattatggg caagtgatgg gatgagttgg atggatggcg gaaacgcagg aacgtgcaag      900
agttataatg tggcttcagt taaggctagc cagccaaact tgaaagttac atggtctaat      960
cttaagtttg gtgacatgga ttccacttac taa                                   993

<210> SEQ ID NO 90
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
atgtttgctc ttcttgcttc ctttgctctg agcgaggtgc acccgaagtt cacctggcag       60
aagtgcacga aggccggctg tacgacgcag aacggcttcc ttgttcacga caagcacatc      120
ggcgacacgt ggtatcgcgg ccctgatcag ctcgactacg agaacgaggt tggcgtgact      180
gtcaagggcg ggacagtgat ccagaagctc gtcaacaagt acaagggcaa caaggtcatc      240
ggttcgcgtc tctatattct gacggccgac gagaagtatt atgaggagtt caacttcgcc      300
gggaaggaga tcagctacac ggtcgacatg agcgagatcc cgtgtgcagt caatgcggcc      360
ctctacaccg ctgagatgcc gaagggcggc aagcccacca aggacgcaag caacctcggc      420
gcagagggcg gcactggcta ttgcgatgcg aactgcgttg acggtggctg ctgcccggag      480
atggacatcc aggaggcctc atccaaggcg atggtttaca ccgcccacac ctgccagagc      540
ccgacagcaa actgcgacag cagtggctgc ggatataacc catatcgcga cagccaggac      600
aagacgttct gggccgtcgg cggaaaggtc gatgtcagca agccggtcac tgtcgtcacc      660
cagtttgtca ccgcaggcgc ttctctgact gcaatcaagc ggaagtacgt ccagggcggc      720
aagacaatcg aggccgcgaa gcagttcgac gacaagttct gcaactggaa cggcaaccag      780
ggacgatcaa tggccgcaat gggaacttca ttcgcacgcg acacgtcct cgtcttctcc      840 ctttgggacg gagacggcat gagctggatg gacggtggaa acgcgggccc ctgcaccagc      900
tacagcaagg cttcggtcga ggcaagcagg ccaaatctga aggtcacatg gtccaacatc      960
aagtttggtg acatcgactc cacctactaa                                       990

<210> SEQ ID NO 91
<211> LENGTH: 1002
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

| | |
|---|---:|
| atgcttgtgt tctttttctc ctattcattg agtgctaatg ctacagaagt tcatccgaag | 60 |
| ttacagtggt cgcgatgcac taaggctggt tgtacgaaag ttaatgcttt tgtggttcat | 120 |
| gacaagcata ttggtgatgt tgcgcaccga ggtgccgatc aacttgatta cgaaaaggaa | 180 |
| gttggtgttg tgacgagtgg aggaacgatt tcgcaacgtc ttgtcagcac ttacaaaggg | 240 |
| aagaaagtta ttgggtctcg tctttatctc atgaccgaag atgataagta ttaccaattg | 300 |
| ttcaattttg ttggaaagga aatcacgtat actgtggaca tgagtcagat cccgtgcagt | 360 |
| gtgaatgcag ctctttatac ttccgaaatg ccaaagggtg ggaaaccaac taaagatgac | 420 |
| gccaaccttg gtgctcaggg tggaactggt tattgtgatg caaactgtgt tgatggtggt | 480 |
| tgctgccctg agtttgatat tcaagaggct tcttctaagg caatggtttt cactgcacac | 540 |
| acttgtcaaa ctccaacgaa tggatgtgat agcagtggtt gtggttacaa tccatatcgt | 600 |
| gacagcaaag ataagacctt ctgggctgtt ggagggaagg ttgatgtgag caagcctgtt | 660 |
| acagtcgtca ctcaatttgt ttcggttggt acttccttaa gtgaggtcaa gcgaaagtat | 720 |
| gttcagggtg ggaaggtcat tgaagctgcc cagtctttga cgacaagtt ctgcaattgg | 780 |
| aatggaggcc aaggacgttc aatgtctgcg atgggggcct catttacaag gggtcatgtt | 840 |
| cttgtgttct cgttgtggga tggtgatggt atgagctgga tggatggtgg caatgctgga | 900 |
| ccttgcacaa gttatagcca tacccaagtc gaagcaactt caccgaactt aaaagtcact | 960 |
| tggtcaaaca tcaagtttgg tgacattgat tcgacctact aa | 1002 |

<210> SEQ ID NO 92
<211> LENGTH: 993
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92

| | |
|---|---:|
| atgtttgctc tcattgcttt cgctttgagt gccccgtcga acacgaccga ggtccatccg | 60 |
| aagttcacat ggtcgaagtg tacgaaggcc ggctgtacga agtgaacgg cttcattgtc | 120 |
| cacgataagc acatcggcga cacgaaggat cgagggacga ccgggatcga ctacgagaag | 180 |
| gatgttggtg tgacggtgaa gggcgacact gtcatccaga agcttgtgag caacggtgca | 240 |
| ttcaagaagg tcatcggctc gcgtctctac atcctcacgg cggacgagaa gctctacgag | 300 |
| gagttcgcgc tggttgggaa ggagttcacc tacaccgtcg acatgagcga gatcccgtgc | 360 |
| ggcgtcaatg cggcgctcta caccgtcgag atgggtggcg aagggcaaag ggacgaacgg | 420 |
| cgctctttat ggcgcaggct actgcgatgc ccacttgcgt tgatggcgac tgctggcccg | 480 |
| gagatggaca ttcaggaggc gtcctccaag gcaatggtct tcaccgctca ctgctgccag | 540 |
| acctcgacca gcggatgcga cacaagcggc tgcggctaca accctatcg tgacaccaag | 600 |
| gacaagacct tctgggcagt gggaggcaaa gtcgatgtca gcaagcccgt aaccattgtc | 660 |
| actcagttcg tcggcaccgg cgcgagcctc acctccatca agaggaagta cgtccagggc | 720 |
| ggaaaggcca ttgacgccgc ccaagacctc aacgacaagt tctgcaactg gaatggcggt | 780 |
| ggcggccgct caatgtcgag gttgggcgcc tcattcacca agggccatgt catcgtcttc | 840 |

| | |
|---|---|
| tcccttggg acagtgatgg catgagctgg atggatggtg gcaatgccgg gccatgcact | 900 |
| tcttacaacg tcaagtcggt cgaatcttcc cggccaaact tgaaggtcac ctggtcgaac | 960 |
| gtcaagttcg gtgacattga ctcgacgtac taa | 993 |

<210> SEQ ID NO 93
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

| | |
|---|---|
| atgtttgctc tcattgcttt cgctttgagt gccccgtcga acacgaccga ggtccatccg | 60 |
| aagttcacat ggtcgaagtg tacgaaggcc ggctgtacga aagtgaacgg cttcattgtc | 120 |
| cacgataagc acatcggcga cacgaaggat cgagggacga ccgggatcga ctacgagaag | 180 |
| gatgttggtg tgacggtgaa gggcgacact gtcatccaga agcttgtgag caacggtgca | 240 |
| ttcaagaagg tcatcggctc gcgtctctac atcctcacgg cggacgagaa gctctacgag | 300 |
| gagttcgcgc tggttgggaa ggagttcacc tacaccgtcg acatgagcga gatcccgtgc | 360 |
| ggcgtcaatg cggcgctcta caccgtcgag atggtggcga agggcaaagg gacgaacggc | 420 |
| gctccttatg gcgcaggcta ctgcggtgct aactgcgttg atggcgactg ctgcccggag | 480 |
| atggacattc aggaggcgtc ctccaaggca atggtcttca ccgctcactg ctgccagacc | 540 |
| tcgaccagcg gatgcgacac aagcggctgc ggctacaacc cctatcgtga caccaaggac | 600 |
| aagaccttct gggcagtggg aggcaaagtc gatgtcagca gcccgtcac cattgtcact | 660 |
| cagttcgtcg gcaccggcgc gagcctcacc tccatcaaga ggaagtacgt ccagggcgga | 720 |
| aaggccattg acgccgccca agacctcaac gacaagttct gcaactggaa tggcggtggc | 780 |
| ggccgctcaa tgtcgaggtt gggcgcctca ttcaccaagg ccatgtcat cgtcttctcc | 840 |
| ctttgggaca gtgatggcat gagctggatg atggtggca atgccgggcc atgcacttct | 900 |
| tacaacgtca agtcggtcga atcttcccgg ccaaacttga aggtcacctg gtcgaacgtc | 960 |
| aagttcggtg acattgactc gacgtactaa | 990 |

<210> SEQ ID NO 94
<211> LENGTH: 993
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94

| | |
|---|---|
| atgtttgctc tcattgcttt cgccttgagt gccccgtcga acacgacgac cgaggtccat | 60 |
| ccgaagttca cctggtcgaa gtgtacgaag gccggctgta cgaaagtgaa cggcttcatt | 120 |
| gtccacgaca agcacatcgg cgacacgaag gatcgaggga ccaccgggat cgactacgag | 180 |
| aaggatgttg gtgtgacggt gaagggcgac actgttatcc agaagcttgt gaacaacggt | 240 |
| gcgttcaaga gggtcattgg ctcgcggctg tacatcctca cgccggacga gaagctctac | 300 |
| gaagagttca acctggttgg gaaggagttc acctacaccg tggacatgag cgagatcccg | 360 |
| tgcggcgtca atgcggcgct gtacaccgtc gagatgccgc caggggcaa gggcacaaac | 420 |
| ggcgctccgt atggtgccgg ctactgcgat ggcaactgcg tggatggcga ctgctgcccg | 480 |
| gagatggaca tccaggaggc gtcctcaaag gcaatggtct tcacggctca ctgctgccag | 540 |

```
acctcgacca gcggctgcga caccagcggc tgcggctaca acccatatcg tgacagcaaa      600
gacaagactt tctgggcggt gggcggcaaa gtcgatgtca gcaagcctgt cacaatcatc      660
actcagttca tcgcgacagg cacgacgctc acctccatca agaggaagta ctcccagggc      720
gggaaggtca ttgaggcggt tcaagacctc aacgacaagt tctgcaactg gaatggcggc      780
ggcggccggt caatggcgag gttggggct tccttcagca agggccatgt catcgtattt       840 tcccttggg  ccggtgatgg catgagctgg atggatggtg gcaatgccgg gccatgcact      900
tcttacaacg tcaagtcggt cgaggcttcc cggccaaact gaaggtcac gtggtcagcc       960 atcaagttcg gtgacattga ctcgacgtac taa                                   993

<210> SEQ ID NO 95
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
atgctggctc tttttgcctg ctacgtgttt tcagctgctg aagcgcatcc gaagtttaca       60
tacaagaagt gtactaaggg tgggtgtact ccagtgagtg cgtttatcgt tcatgacaag      120
cacattggtc aagtttcaga tcgaaaggac actgctattg actatgagaa ggatgttggt      180
gttacagtta gtggtggaac tgtttcccaa aagcttgtga acacgtacaa tggtcaaaag      240
gttattggtt ctcgacttta tgtcttgaat gcagatgaga agaactatga atcttcaag       300 ttaacaggga aggaattcac gtatactgtt gaaatgaagg aaatccaatg tggtgttaat      360
gctgctttgt acacttgcga aatgccagcg gcaggcaagc caccatatgg cgctgcttat      420
ggttctggtt attgtgatgg aaactgtgtt gatggttcct gctgtccaga attcgatatt      480
ccaggaggct tcttctcatg caatggtctt cactgttcac cttgctcaac tccaaccaat      540
ggatgcgata ccagcggctg tggttataac ccatacagag atagccaaga taagaccttc      600
tgggctgtcg gtggaaaagt tgatgtcagt cgggcagtta cagtcgtcac tcaatttgtt      660
gcaactggaa ccactttgac tgaaatcaag cgaaagtatg tccagggtgg taaagtgatc      720
gaagctgcta gtctttaag  cgacaagttt tgtaattata tggtgggac  aagaacaatg      780 gctaatatgg gtgcttcatt caacaggggt catgtcctcg tcttttcact ttgggatggt      840
gacggcatga gctggctgga cggtggcaat gctggatcat gcacaagtta caatgttagg      900
caagtcgagg caacttctcc aaacttgaag gtcacttggt ccgatgttag atttggtgac      960
attgactcta cctactaa                                                    978

<210> SEQ ID NO 96
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
atgttgggtc tttttgcctg ctatgcattt tcagcggcag aagcgcatcc gaagtttacc       60
tataagaagt gtactaaggg tgggtgtact ccagtgagtg catttattgt tcatgacaag      120
cacattggtc aagtttcaga tcgcaaggac actgctattg actatgagaa ggatgttggt      180
gttacagtta gtggtgggac tatttcccaa aaacttgtga acacgtacaa tggtcaaaag      240
```

```
gttattggtt ctcgagttta tgtcttgaat gcagatgaga agaactatga aatcttcaag    300
ttaactggga aggaattcac gtatactgtt gaaatgaagg aaatccaatg tggtgttaat    360
gctgctctgt acacttgcga aatgccagcg gcaggcaagc caccatatgg cgctgcttat    420
ggttctggct actgtgatgg aaactgtgtt gatggttcct gctgtccaga attcgatatt    480
caggaggctt cttctcatgc aatggtcttc actgttcaca cttgctcaac tccaaccaat    540
ggatgcgata ccagcggctg tggttacaac ccatacagag atagccaaga taagaccttc    600
tgggctgtcg gtggaaaagt tgatgtcagt cgggcggtta cagtcatcac tcaatttgtt    660
gcaactggaa ccactttgac tgaaatcaag cgaaagtatg tccagggtgg taaagtgatc    720
gaagctgcta agtctttaag cgacaagttc tgtaattata tggtggagc aagaacaatg    780 gctaatatgg gtgcttcatt caacagggt catgtcctcg tcttctcact ttgggatggt    840
gacggcatga gctggctgga cggtggcaat gctgggtcat gcacaagtta caatgttagg    900
caagtcgagg caacttctcc aaacttgaag gtcacttggt ccgatgttag atttggtgac    960
gttgattcta cctactaa                                                  978

<210> SEQ ID NO 97
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
atgtttgctc tttttgtttg ttatgcattt tcagcagctg aagcccatcc aaagtttaca     60
tacaagaagt gtaccaaggg aggttatact cctgtgaatg cgtttattgt tcatgacaag    120
cacattggcc aagtttcaga tcgaaaggac acagcaattg actatgagaa ggatgttggt    180
gtcacagtta gtggtggaac tctttcccag aagcttgtga acacatacaa tggtcaaaag    240
gttattggtt ctcgacttta tgtcctcaat gcagatgaga agaactatga aatattcaag    300
ttaactggca aggaattcac atacactgtt gaaatgaagg aaatccaatg tggtgttaat    360
gctgctctgt acacttgtga aatgccagca gcaggaaagg caccatatgg cgctgcttat    420
ggttctggtt attgtgatgg aaactgcgtt gatggttcct gctgtccaga gttcgatatt    480
caggaggctt cttctcatgc aatggtcttc actgttcata cttgctcaac tccaactaat    540
ggatgcgaca ccagcggatg tggttacaac ccatacagag atagccaaga taagaccttc    600
tgggctgttg gtggaaaagt tgacgtcagc aaaccagtta cagtcgtcac tcaattcgtt    660
gcaactggaa ccactttgac tgaaatcaag cgaaagtatg tccagggtgg taaagtcacg    720
gaagctgcta agtctttaag cgacaagttc tgtaattata acggtggaac aagaacaatg    780
gctaacatgg gtgcttcatt caacagaggt catgtcctcg tcttttcact ttgggatggt    840
gacggcatga gctggatgga cgggggcaat gctgggtcct gcacaagtta caatgttaag    900
caagtcgagg caacttcacc aaacttgaag gttacttggt cagatgttag gtttggtgac    960
atcgattcta cctactaa                                                  978

<210> SEQ ID NO 98
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 98

```
atgcttgctg tttttgcatg ttatgcattt tcagcagctg aagcacatcc aaagtttaca        60
tggcagaagt gtactaaagc agggtgtact ccagtgagtg ttttttggt tcatgacaaa        120
cacattggta acacagcaga tcgaaaggat acagcgattg attatgagaa ggatgttggt        180
gttgtcgtta caggtggcac agtttcccaa cgtcttgtta gcacgtacaa tggtaaaaag        240
gtgattggtt cacgaattta cattcttgat gcagatgaga agacttatac tcttttcaag        300
ttgacaggga aggaattcac atacacagtt gacatgagtc aaattccatg cagtgttaac        360
gctgctcttt acagctgtga aatgccagca gcaggtaagg aacatatgg agctgcttat        420
ggtgcaggtt attgtgatgc aaactgtgtt gatggaagtt gttgcccaga atttgatatt        480
caggaggctt catctcatgc aatagtttac acagctcata cttgttctac tccaacaagt        540
ggatgtgata caagtggctg tggttacaac ccctacagag atagcaacga taaaacattc        600
tgggctgtcg gtgtaaagt ggatgtcagc aagccagtga ctatcgtcac tcaattcgtt        660
gcaacgggaa cgactttaac tgaaatcaag cgaaagtatg tccagggtgg aaaggctatt        720
gaggctgcta atctttaag tgatactttc tgcaactgga gaggtggaac tcgttcaatg        780
gcaagcatgg gaaattcatt aacaaaggt catgtaatcg tattctctct tgggacggt         840
gacggcatga gttggatgga tggtggaaat gctggttctt gcactagtta taaccacaat        900
caagtcgaag caactcaacc gaacttgaag gtgacttggt caaacatcaa gtttggtgat        960
attgactcta cctattaa                                                       978
```

<210> SEQ ID NO 99
<211> LENGTH: 987
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99

```
atgctttctt tcctgctctc tctctgtctc tccgcggaga ctcacccgaa gttcacgtgg        60
caatcgtgca ccaaatccgg ctgcaaagac gtctacggct tccttgttca cgatcgccat        120
atcgggaata tctgggatcg cgagaagcac ggcgatctcg actacgtgaa ggacatcggt        180
gttactgcta ccggtggtac tctccagcag aagctcgtta gccctaagtc tgccgcgaat        240
gagggcaata atgttattgg ctctcgcctc tatatcgtcg attcggcgga tcagaagtac        300
gagctcttca gtttgttgg caaagaattc acatacactg ttgatatgtc gaaatccca         360
tgcggcgtga atgcggcgct ctacaccgtc gagatgcagc ccggcgggaa gagcccggc         420
ggagttcagt acggatacgg atactgcgac gcgaactgcg tcgacggggg ctgctgcgcg        480
gagttcgaca tccaggaggc gtcgagcaag gccatggttt tcacatcaca tgtctgccaa        540
cagctcactc aaaattgtga ctccagcggt tgcggttata atccgtatcg tgattcaaag        600
gattacgctt tctggggaac aacgatagac gtcaaaaagc cagtaacggt cgtcactcaa        660
tttattggga cagccggaac aatgactgag gtcaggaggt tgtacgtgca gggagggaag        720
gtcgtgaagt cccagcagtc gctcaatgac caattctgtc gttatcagcc cggagactgg        780
cataatatgg accacatggg gcagtcgttc cagcgtggac acgtcgtcgt cttctcgctc        840
tgggatggaa atgaatgag ttggatggac ggtggaaatg ctgggccctg caagtcgtat        900
gacgttgcaa ctattgagaa gacgcagcca aatctcaaag tgacctggtc gggcgtgaag        960
```

```
tttggggatc tggactcgac ttactaa                                          987
```

<210> SEQ ID NO 100
<211> LENGTH: 975
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
atgcttcccg ttcttctttc catctgcgtc agcgaagccc accccaagtt cggctggcag       60
caatgcaccc gctcaggctg cagcaccgtg caaggtttcc ttgtgcacga tcgtcattat      120
gcgggcattt gggatcgcga aagcgtcccc gttctcgatt atcccaaaga cgttggtgcg      180
acagcgacag gtggcactct ttctcaacgc ctcgtcagca aaatggcgga tggcacgaac      240
gtcatcggtt cgcggcttta tatcgttgca tccgacgata agaattatga gatgtttaca      300
ctggttggca aagagtttac gtacaccgtt gatctctctg aaattccgtg cggagtgaat      360
gccgcgcttt acaccgtcga aatgccaaaa ggtggaaaag cacccggata tgttgattac      420
ggttatggat attgcgatgc aaactgcgtt gatggaggat gttgtccgga atttgatatt      480
caagaagctt ccagtaaagg gatggtgttt acgtcgcaca cctgtgagag aagtaatgga      540
ggatgtgatt ctggaggctg tggctataat ccctatcgcg attcaaacga tcacgcgttt      600
tgggggacga cgatagacgt caaaaagccg gtaacggtcg tcactcaatt tattgggtcg      660
ggaagtcagt tgaccgaagt gagaagattg tatgtccaga tggaaaagt cattaaggcc       720 gctcagtcgt tgacggacac attctgtcat tatggaccaa cggattcaca tcggttggca      780
aatatgggtg cttctttcgc aagaggtcat gtggtcgtat tctccattgtg ggattcaaat     840 gggatgggat ggatggacgg gggaaatgcc agaccgtgta ccagttatga cacggggacg      900
attgaaaaga catcaccgaa tttgaaggtg acgtggtcga acgtgaagta tggtgaccctt      960 gattcgacgt actaa                                                       975
```

<210> SEQ ID NO 101
<211> LENGTH: 987
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
atgctttctc tacttctctc catctccctg ctgctgaag cgcaccccaa gcttagctgg        60
caaacctgca ccagagaggg ctgcaagacc gtcaacggct acctggttca cgatcgccat      120
atcggcaatg tctgggatcg cgaacgccat ggcgatctcg actatgcgaa agacatcggc      180
gtgacgacga gcggttccac gctccaacaa aagcttgtca gccaggcttc tcggcgaat      240 aatggcgcga atgtgattgg ctcccggctc tatttggtcg actctgctga ccaaaaatat      300
gaacttttca agctggttgg caaggaattc acgtacaccg ttgatatgtc agaaatccca      360
tgcggggtaa atgccgcgct ctatacggtc gagatgcagg cagctggcaa agctcctggt      420
ggagtgcaat acggctatgg gtattgcgat gcgaactgcg tcgacgggag ctgctgcgcg      480
gagtttgaca tccaggaagc atcgagcaag gccatggttt tcacatcaca tgtctgtgag      540
aagatcgacg gcggttgtga ctcgagcggt tgcggttata atccctatcg tgattcaaag      600
gatcatgcct tttggggaac aacaattgat gtgacaaagc cagtcactgt cgtgacgcaa      660
```

```
tttatcggaa ctgcgggaac aatgaccgaa gtgaggaggc tgtatgttca gggagggaaa      720
gtgattaagg cagcacagtc actcagtgac acatttgtc actacagtgc aaccgatgtc       780
cataatatgg cccatatggg tgcatcgttc cagagaggac acgtaatcgt gttttcactg      840
tgggatggaa acggaatgag ttggatggat ggcggaaatg caggaccgtg cacaagttat      900
gacgtggcga caattgagaa aaccaggccg aatttgaagg tgacttggtc aaacgtgaag      960
ttcggggaca ttgactcgac ttactaa                                          987
```

<210> SEQ ID NO 102
<211> LENGTH: 957
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
atgctcgcag ttctgctcgc actcgggctg tcggagacgc atccgaagtt cacgtggcaa       60
gaatgtacga agtccggctg tactgcgaag tcgggctaca tcgtccacga caagcacatt      120
gctgagacgc gtaaccgtga ccaataccggt gacctggact acgagaagga cgtcggtgtt     180
accgtgagcg gtggtaccgt gaagcagcgt cttgttagcc cgaactacca gaactacaag      240
gttattggtt cacgtcttta catcgttgat gctgacgaca gtactacca gcttttcacg       300 ttcatcggga aggagttcac gtacacggtt gatatgtcag agatcccgtg cggagtgaat      360
gcggcgcttt acactgttga aatgccgaag gccggtaaga ctcccggtgg tgttgagtac      420
ggttacgggt actgcgatgc taactcagtt gatggagatt cgtgcgcaga attcgacatc      480
caggaggcgt cgagcaaggc gattgtttac acttcacacg cgtgctcgtc tcaaaacgagt     540 gggtgtgaca cgagcggctg cggctacaac ccgtaccgtg actctaacga ccacgcgttc     600
tggggtacta cgatcaacgt gaaccagccg gttacgattg ttactcagtt catcggctcc     660
gggagttcgc ttactgaggt taagcgtctt tacgtgcagg gtgggaaggt tacggaggcc    720
gcgaagtcgc ttactgctga cggttgctgc aacaacatcc ggaacatcgg tccgtcgttt    780
gcacgtgggc acgttgttgt cttctcgctt tgggactcga acgggatgag ctggatggac    840
ggtgggaacg ctggcccgtg cacgagctac aacatcgaca acgtcgagaa gagttcgccg    900
aacttgaagg tgacgtggtc gaacatcaag tacggagaca tcgactcaac gtattaa        957
```

<210> SEQ ID NO 103
<211> LENGTH: 987
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
atgttccttg cgctcgcgtc gttggtcggg tgcgccgaga agcacccgcc gttcacgtgg       60
gagaagtgca cgaaagcggg gtgtacaaaa gtgaacggtt accttgttca cgacaagcac      120
attgggaatg tgtgggatcg gggctccgat cagcttgatt acgagaacga agttggcgtg      180
accgtctcgg gcggtactct gcagcagaag cttgtcaaca aatacaaagg gcagaaagtt      240
atcggctctc gactgtacat tctcgacgat aacgatcagt actaccaact gttcaacttt      300
gtgggcaagg agttcactta cactgtcgac atgtctgaga tcccgtgcgg cgtcaacgcg      360
gcactctaca ccgccgagat gccgaaggca gggaagccgc cgggcggcac cgcaatcggc      420
```

```
acaggctact gcgacgcgaa ctgcgtcgac ggaagctgct gcgcagagtt cgacatccag    480
gaggcctcgt cgaaggccat ggtctacaca gcgcacatgt gcacatcaca gaacaacgga    540
tgcgactcca gcgggtgcgg ttacaatcca taccgcgata gcaaggcgta caacttctgg    600
ggaggcacca tcgacgttac aaagcccgta accgtcgtaa ctcagttcat cggggcagga    660
acctcaatgt ccgccgtgag aagaaagtat gtccagaatg gaaaggtcat tgactccccc    720
ggaatggtca acaacagtta ctgcaactgg gtacactgcc aatgcccaa cggtgactgg     780 aacccgctca ttccaatggc aggaagcttc gcaagagggc acgtcgtcgt cttttccctg    840
tgggacggaa acgggatgat gtggatggac ggaggaaata acggaccctg caagagctac    900
gacgtcgcaa gcgttgaggc aacacgcccc aacctcaaag tgacctggtc aaaggtcagg    960
ttcggcgaca tcgacagcac gtactga                                        987

<210> SEQ ID NO 104
<211> LENGTH: 1026
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
atgctggcga tcctcgcgag tctctccctt tccgaaacct cgtcgccgaa gctggcctgg     60
cagaagtgca ccaaagccgg ctgctcctcc atcacaggct ccgttgtcat cgacaaagag    120
aatcgcgcca ctgaaacaac cccgatcgag gattatgggg cggccctcgg ggtcacgacg    180
agcggcaaca ctctcaagca gcgactcgtg accgtttaca acggcaagcg cgtcatcgga    240
agccgtctct atctgctcgc ggcagatggc caatcgtatg aactgttcaa ttttgttggc    300
aaggagttca ctttcgatgt tgacctttcg cagatcctct gcggcgtgaa tgcggccctt    360
tacacatccg aaatgccagc caaaggcgca ggctccgcgg gagccgttta cggcggcgga    420
tactgcgatg cgaactacgt cggagggtcc ggatgccacg aaatggacat catggaggcg    480
aacaaatatg cgatggtttt cacaacccac acatgccaga cactcgggat tcaggcgggg    540
cgaggctcct gcgacaacgc gggttgcggc ttcaacgcat atcgcttcgg cgcaaagaca    600
ttttggagca acgatattaa caccgcccaa aagatcacag tcatcacaca attcctgggc    660
agtggcgcga cgatctcgga gattcgcagg ctgtatatgc agggcggaaa ggtgattaag    720
aacgcggccg tgcacgtttg gggaagccag gtggcgtacg attcgatcgt tccgggattc    780
tgccagtcga gcgggcacca aacagacggc tggcattcgc tcaaccaaat ggcggcgtcc    840
ttcgtgaggg ggcacgtgct cgtgttctca ctgtgggatt cggatgacat ggggtggctt    900
gatgggcaaa atggagaata tggaccctgc ggtaatccgt cggcagcttc cgtcgaggcg    960
cagcatcctg acatgacgct gacattttcg aacatcaagt tcggagatat tgactccact   1020
tactaa                                                              1026

<210> SEQ ID NO 105
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
atgcttggcc ttcttgttgg ctttgcgttg agcaaaggtg gtcctgctct ctcatggtca     60
```

```
gagtgtacca aggctggctg cactcctcac accgcttccg tggtcagtga ctggaaggat      120
ggtgttcagg attccattga ctttgatgct ctcgactatg ataaggacat tggtgtgacc      180
acgagtggtg gctcgctctc ccagcgtctt gtctccaagt ccactggcaa gaaggtcatc      240
ggctcccggc tctatctcct ggattcctcc ggcaccaagt accagctgtt caagttcatc      300
ggcaaggagt tcacatacga tgtcgatctg gcccagatcg gctgcgctgt gaacgccgct      360
ctctacaccg tcgaaatggc cgctgatggc agcaagggct caggcagcaa ccgcgcgaag      420
aagggcgctg aatacggaac cggatattgc gatgggaact acgtcgacgg aacgggctgc      480
gctgaattcg acattcagga ggccaacaac aaggcaatgg tttacaccac ccatggttgc      540
agctcacccg ccagggcgt ccagggctgt ggcaccagcg gttgcggtta taacgtctat      600
cgtgactcag ggaagaaggc gttctggggc acgacgatca acaccgcgca aaaggtcact      660
gttgtcaccc aattcgttgg ttccggcgcc tctttgaccg aaatccgccg ccgctatgtc      720
cagggtggca aggttattga tgtccctgac aagaccaagt acctcaacgc ggcgttctgt      780
ggtgcccaga agatctctgg aatcgcacgt tcgttcgtca acggccatgt cctcgtcttc      840
tcccttggg actctgacgg catgagctgg ctggatggtg gaaacgctgg accgtgcact      900
ggcaatgagc gagtcgcgca aatcgaagac gcgaacccga acgccaaggt cgtctggtcg      960
aacatcaagt tcggcgacat cgacactacc tactccgcct aa                        1002

<210> SEQ ID NO 106
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
atgcttggcc ttcttgttgg ctttgcgttg agcaaaggtg gtcctgctct ctcatggtca       60
gagtgtacca aggctggctg cactcctcac accgcttccg tggtcagtga ctggaaggat      120
ggtgttcagg attccattga ctttgatgct ctcgactatg ataaggacat tggtgtgacc      180
acgagtggtg gctcgctctc ccagcgtctt gtctccaagt ccactggcaa gaaggtcatc      240
ggctcccggc tctatctcct ggattcctcc ggcaccaagt accagctgtt caagttcatc      300
ggcaaggagt tcacatacga tgtcgatctg gcccagatcg gctgcgctgt gaacgccgct      360
ctctacaccg tcgaaatggc cgctgatggc agcaagggct caggcagcaa ccgcgcgaag      420
aagggcgctg aatacggaac cggatattgc gatgggaact acgtcgacgg aacgggctgc      480
gctgaattcg acattcagga ggccaacaac aaggcaatgg tttacaccac ccatggttgc      540
agctcacccg ccagggcgt ccagggctgt gacaccagcg gttgcggtta taacgtctat      600
cgtgactcag ggaacaaggc gttctggggc acgacgatca acaccgcgca aaaggtcact      660
gttgtcaccc aattcgttgg ttccggcgcc tctttgaccg aaatccgccg ccgctatgtc      720
cagggtggca aggttattga tgtccctgac aagaccaagt acctcaacgc ggcgttctgt      780
ggtgcccaga agatctctgg aatcgcacgt tcgttcgtca acggccatgt cctcgtcttc      840
tcccttggg actctgacgg catgagctgg ctggatggtg gaaacgctgg accgtgcact      900
ggcaatgagc gagtcgcgca aatcgaagac gcgaacccga acgccaaggt cgtctggtcg      960
aacatcaagt tcggcgacat cgacactacc tactccgcct aa                        1002

<210> SEQ ID NO 107
<211> LENGTH: 996
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
atgcttggcc ttcttgttgg ctttgctctg agcaagggtg gtcccgcctt gtcgtggcaa       60
gagtgtacca aggctggctg tacgccccac gcggcttcag tcgtcagcga ctggaaggat      120
ggtgtccagg attccattga cttcgatgcg ctcgactatg agaaggacat tggtgtcacc      180
agcagcggcg gctcgctttc caacgccctt gtctccaagt ccactggcaa gaaagtcatc      240
ggctcgcgcc tctatctctt ggattccacc ggcaccaagt accagctgtt caagttcatc      300
ggcaaggaat tcacctacga tgtcgatctt gctcagatcg gctgcgctgt gaacgccgct      360
ctctacaccg tcgaaatggc cgctgatggc agcaaaggct cgggcagcaa ccgcgcgaag      420
cacggcgcca atacggaac tgggtattgc gatggtaact atgtcgatgg aaccggctgc      480
gcggagttcg acattcagga agccaacaac aaggcaatgg tttacacaac ccacggctgc      540
agctcacccg ccaaggcgt tcagggctgc gacaccagcg gttgcggtta taacgtctat      600
cgcgactcca acaataagct cttctggggc acgacgatca actccgctca aaaggtcact      660
gttgtcaccc aattcgttgg ttccggggca tccttgaccg aaatccgccg ccgctatgtc      720
cagggtggca aggttattga cgtccccgac aagactaagt acctcaacgc ggcgttctgt      780
ggcgcccaga gatctctgg aatcgctcgt tcgttcgtca acggccatgt cctcgtcttc      840
tccctttggg actctgacgg aatgagctgg ctcgatggtg gaaacgctgg cccatgcact      900
ggcagtgagc gcgtcgagca atcgaaaac gccaacccga acgctaaggt gacctggtcg      960
aacatcaagt tcggcgacat cgactcgacc tactaa                                996
```

<210> SEQ ID NO 108
<211> LENGTH: 996
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

```
atgcttggcc ttcttgttgg ctttgctttg agcaagggtg gtcccgctct tacatggcaa       60
gagtgtacca aagctggctg tactccccac gcagcttcag tcgtcactga ctggaagaat      120
ggtgtccaag attccattga cttcgatgct ctcgactatg acaaggacat tggtgtgacc      180
agcagtggtg gctcccttttc ccaacgtctt gtctcgaaat ccactggcaa gaaagtgatt      240
ggttcgcgac tttatctctt ggactccaca ggcaccaagt accagctgtt caagtttatc      300
ggcaaggagt tcacctacga tgtcgaccctt gctcagatcg gctgcgctgt gaatgccgct      360
ctatataccg tggaaatggc cgccgatggt agcaaaggtt caggcagcaa ccgcgcgaag      420
aacggtgctg catatggcac tgggtattgt gatgggaata cggtcgatgg aactggttgc      480
gctgaattcg acattcagga agccaacaac aaggctatgg tttacacaac gcacggctgt      540
aacggcgtag tcaaggtgt tcagggctgc gacaccagcg gttgcggtta taacgtctat      600
cgtgactctg gaaacaaagc gttttggggc acgactatca acaccgctca aaaggtcact      660
gttgttaccc aatttgttgg ttcgggttcc agtttgaccg aaatccgccg tcgttatgtt      720
caaggtggta aaactattga cgtccctgac aaaaccaagt acctcaacgc agcattctgc      780
ggtgcttcaa agatctctgg aattgctcgt tcgttcgttc agggtcatgt tcttgtcttc      840
```

```
tctctttggg actccaatgg catggcttgg ctcgacgctg gaagctctgg accgtgcact      900
gggaatgaac aagtcgagca atcgaaaac gcgaacccga acgcccacgt ggtctggtcg       960
aacatcaagt tcggggacat cgacacgacc tactaa                                996
```

<210> SEQ ID NO 109
<211> LENGTH: 996
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
atgcttggcc ttcttgttgg cattgctttg agcaagggtg gtcccctct tatatggcag        60 gagtgtacca aagcgagctg tactccgcat ctcggttcag ttgtcagtga ctggaagaat      120
ggtgtccaag attccatcga cttcgatgct ctcgactatg agaaggacat tggtgtgacc      180
accagtggtg gctccctctc ccaacgtctt gtctccaagt ccactggcaa gaaagtgatc      240
ggttcacgcc tgtatctcat ggactccaca gggacgaagt accagctgtt cacctttatc     300
ggcaaggagt tcacctacga tgtcgacgtt tctacactcc cctgcggtgt gaacgctgct     360
ctctatgccg tggaaatggc ggctgatggc agcaaaggct cgggcagcaa ccgcgcgaag     420
agcggtgctg catatgggac tgggtattgc gatggtaatt acgtcgatgg aactggttgc     480
ggtgaattcg acattcagga agccaacaac aaggcgatgg tctacacaat acacccctgc    540
aacggtgtcg gccaaggtgt tcagggctgc gacaccagcg ggtgcggtta taacgtctat     600
cgtgactctg gaaacaaagc gttttggggg acgaccatca acacggctga aaagatcact    660
gttgtgaccc aattcgttgg ttcgggttcc acattgaggg aaatccgccg tcgttatgtt    720
caaggtggga aaactattga cgtccctgat agaaccaagt acctcaacgc agcattctgc    780
ggtgcttcaa agatctctgc aattgctcgc tcgttcgctc aaggttatgt cattgtcttc    840
tctctttggg actccaatgg catggcttgg ctcgacggtg gatccgctgg accgtgcact    900
ggaaatgaac aagtcgagca attcgaaaac gcgaacccga acgcccacgt ggtctggtcg    960
aacatcaagt acggggacat cgacacgacc tactaa                              996
```

<210> SEQ ID NO 110
<211> LENGTH: 1029
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
atgctcctcc tcctctccgc cttctccgcg tgcgagacgc gcccgtccct cacgtggcag       60
caatgtacgc gtgctggctg caccccagtg acaggctccg ttgtctcaga cacggatcag     120
cgtccgagcg cgggtgcgga tatcaacaat gcggacatcg gggtgagcag cagcggcggc    180
tcacttcagc agaatctggt gacgacgggc agcctcggta agatcatcgg gtcgcggctg     240
tatctgatgg attcggccgg ctcgaagtat caattgttca accttgtcgg caaagagatc    300
acgtacgacg tcacgatgac gagcatcggg tgcgcggtga atgcggcgct ctatacggtc    360
gagatgcccg ccggggcgga ggcccaattc ggcggcgcg cgggcggcag cggctattgc     420
gacgcgaact tcgtgaagag caagggcagc tcgaaggccg ggtgcgccga attcgacatc    480
caggaggcga atttctacgg aatggtcttc accagccacc catgccagag ccccggtcag    540
```

```
gtcggccagg gcggcggctc ctgccagtcc gacggatgcg gattcaacgg atatagatat      600
ggggcacgcg acttctggac ttcccagatc aacccgcggt cgaggctcac cgtcatcaca      660
cagttcgtcg gaagtgcggg aacgctcacc gaggtccggc gcaagtatat tcagggcgga      720
aaggtcatcc agaacccgac cgtcaacgtg tacagcaatg gcaacttcaa ctctctcagc      780
gaagcattct gcaaggcggc ggggcacccg ctctccggat ggacatcatt cgcagcaatg      840
gggcaatcgt tcgggcgcgg ccacgtgctc gtcttcagcc tgtgggatag ctttgacatg      900
gggtggctgt cgggcagcac cgagtatgga cctagcacat catccgataa actggaggct      960
gagacccact tggatgcaaa ggtaatttgg agcagtatca aatatggtga catcgacacc     1020
acttactaa                                                             1029
```

<210> SEQ ID NO 111
<211> LENGTH: 1032
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
atgattgctg ccctgcttgc gctcgcgctc gctgagacca ggccgtcctt gatttggtcg       60
cagtgtacga aggccggctg tacgaaggtg tctgggtcgg tcactgtcga tgtgtcttcc      120
cgcgggaagc cgcctgcgga tgtcgactat gctgcccagc ttggcgtcac ctcgacgggg      180
acgtccctga ctcagaagct ggtgacgatc cacaatggcg tcaagaacgt cggctcgcgt      240
ctctacctgc tcaattctgc cgggacggcc tatcagatgt tcaagctagt cgggaaggag      300
ctgacctacg atgtcgacct gagcgaactg ccgtgcggca tgaacggcgc catctacacg      360
tccgagatgc ccgcggccgg cggctctgct ggagcggctt atggcagcgg ctactgcgat      420
gcgaactacg tggacggcaa tggctgcgcg gagttcgaca ttgccgaggc gaacacccga      480
ggcaacgttt tcaccaccca tccatgcaac aggctcggca caggcacgag gaccactatc      540
cagtgccagt cggacggctg cggcttcaac gcttaccgct acggtgcgaa gcagttctgg      600
ggaccgggct cgagctacac cgtcgacaca tcgaagccta tgacagtcat cacgcagttc      660
ctcggcactg gcagcctcac cgagatccgc aggctataca acagggcgg caagctcatc      720 cagaacgcaa agccgctcgt ctacaacacc gccagctacg actcactcac cgacgctttc      780
tgcaagaccg cagggcactc agtcacaccc accaccagcc tggcccagat gggcaagtcg      840
ttcgatgtcg ccacgttcct catcttctcg ctctgggacg cagtcgacgg aatgggttgg      900
ctcgatgcct cagagtacgg gccatgccct ggtgggactg ctgattcagc ggcggccatc      960
gaggcaagga gtccgaactt gaagattgtc tattcgaacg tcaagttcgg tgacatcgac     1020
tctacctact ga                                                         1032
```

<210> SEQ ID NO 112
<211> LENGTH: 1077
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
atgatcgttg ctttgattgc tcttgtcact ggagcaacac ttgttgaaac aaagcccgtt       60
gtcaaatggc aaaaatgtac gaaatctggt tgtacaacag tgactggttc agtcactact      120
```

```
gactttgaat ctcgtggaga gaaaaaatcg gatcataccg cagccgttga ttatgttcaa    180
caacttgggg ttgaatcaac aggcgatatg cttagtcaga agcttgtcac aatatacaat    240
gggaaaaaga acgtcgggtc tcgtctttat ctccttgatc ctactggtga aaagtatcaa    300
atgttttatt tagttaacca tgaattcact tatactgttg atctttctga atgtccttgt    360
ggtatgaatg ctgccatttta tacgtcagag atggctgctg aaggtgctgg tctcggtcct    420
aaatttggac aaggttattg tgatgcaaac tacgttggag ttgatgaacg tggatgtgcc    480
gagtttgata ttatggaagc taatactcgt gccattacat tcacgactca tccatgttca    540
aaactgaaac aaaatgttaa gaatacagtc cagtgtatgc ctgatggttg cggttttaat    600
gcataccgat atggtggtag aaccttctac ggccctggtg ctacatataa agttgattca    660
acaaagaaga ttaccgtggt cacccaattt atatcaagtg atggaactga taaaggtgat    720
cttgttgaga ttcgtagatt gtacgttcaa ggtggaaaag tcattcctaa tgcgaaggtt    780
tctgtgtata attcaggtga attcgattct atcagtgaca aattctgtag aacagctgga    840
catcagattg atggatatca tgcgttgtct ttcatggggc agtctttcaa gaatggccac    900
gcacttatct tctcattatg ggatgcaaat gatggaatga catggttgga tgcaggtgag    960
tacgggccat gccccggaag tccagctgaa acgggtgcgg caattgaagc cgcgcatcct   1020
aatcttcggg tatattggtc aggaatcaaa tatggtgatc ttgattccac gtactaa      1077

<210> SEQ ID NO 113
<211> LENGTH: 1230
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
atgattttgc ttctttgtgg atttggcctc tcgcaacttg ctggttcatc cgaggttcat     60
ccgaagatca cttggaagaa gtgtactaag gctgggtgta gttcccaaag tggtggaatt    120
gttattgatt cagaatggcg tgagattgtt gatgccaatg gaagaaatg catgacagat     180 agccagagtt gggattcatc tgtttgttct gggcctgcag attgttctca gaagtgttac    240
ctccaaggtt ataagtattc agatgccggc gtgtccacga caggtgatgc agtccgtctg    300
aagtttgtaa ctccgactgg cattggttct cgtgtttatc ttttcgatga aactgcagga    360
acttatgtga acttcaaggt tcttaataag gaatttacat cgatattga tacttctcaa     420 gttccatgtg ctgttaatgg tgctctttac ttttctgaga tggatcctga tggtggtaag    480
agtcgattcc cgaacaataa ggctggtgct aagtatggga ctggttattg tgatgcacaa    540
tgtcctcgtg acgggaagtt cattggaaat aacgccaatt ccgtcgtca atatggttcc      600 tgttgctttg aatgggatat ttgggaaggt aacgttggag caactcaaat ggctgctcat    660
ccttgctcag ctacagttaa taccccagct gctgtctgtg aatcaaattg caatcaatgt    720
gacactgcag gatgtgcttg gaatccatac aaagttgaat ccaacatggg taaaggtcat    780
acctactatg ggaagggaca acaagttgac ccgaccaaga aaataaccgt cgttactcaa    840
tttaagactg ccgatggaac tgacttgggt caacttaaag aagttcgtcg tctttatgtt    900
caaggtggaa aagtcattcc gaacaataag aagattcaga atgataagcc ttttgattca    960
atcggagatg attgctgtca aaacggatca agtggtgacg ctgcttatgt cactcgtggt   1020
ggggataaag catttactac ttctttccgc cgtggtgctg tcttagcaat gtccatctgg   1080
```

```
actgatggaa gtatgggttg gttaaattct ggtgacgctg gtccatgcgg aaatcctagt    1140
ggtggtaaag atggacttgc caaacaatat ccaaatgctt atgttgaatt ctccaatatc    1200
cgttttggtg atattgactc cacttactaa                                     1230
```

<210> SEQ ID NO 114
<211> LENGTH: 945
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
atgcttgctt tacttgctgt tttcagtctt gctgctcatc cgaaattgac ttggcaaaag     60
tgtacaaaag gtggttgcac cactcagaat ggttttattg ttggagacac aactgcaggt    120
gatattgatt atgaaactca acaaggagtg acagtgagtg gtgatacagt gaagcagaga    180
ttagtaacca attataatgg aaagaaaatc gttggttcac gcctttatct ccttgcaagt    240
gatgagcaaa actatgagct gttcaatttt gttaataagg aaattgcata cgatattgat    300
atttctcaga ttccttgcgg agttaatgct gcattctaca cagttgaaat gccaaagaat    360
ggtggaacta ctggtgctgc tgcaggagga ggttattgtg atggaaacta tgttgatggc    420
gaggggtgtt ttgagatgga tattcaggag gcaaacaata aggccatggt ttacacaatg    480
cacacctgcc aaaacactgg agttcaggct tcaaatggtc aatgtgatgg aaacggttgc    540
ggaattaata cttatcgaga taatgacaaa caattctggg gtacaacagt taatactgca    600
cagaaaatga ctgttgttac tcagttttg ggatctggaa cagcagtaac tcaaatcaag    660
aggctttatg ttcaaaatgg gaaagttatc cagagccctg gttcgattac tgatagtggt    720
tgtggtaata gtggatggca tacacttgct cacttaggtg aatcatttac caaaggacat    780
gttctggttt tctcactttg ggattcaaac ggaatgagtt ggcttgactc aggtaataat    840
ggaccttgcg gaagttacga cattaatacg attgagtctc aaagtccagg attaactgtg    900
acttggagta atatcaagtt tggagatatt gactcaactt actaa                    945
```

<210> SEQ ID NO 115
<211> LENGTH: 1209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
atgcttctcg tcttttagt ggtttctggt ttatcgcaag gggctggaac agcggaaact     60
catcttaaga ttacgtggca gaaatgtacg aaatctggtt gctcaaacca gcagggtggt    120
attgttgtcg actcagagtg gcgtgaggtt gtagatgcga gtgaaaaatc atgtcttcga    180
gatggtaata gttgggattc atctgtttgt gatggagagg cggattgctc gacaaagtgt    240
cgattgaatg gttttaatta tgcagatatt ggagttacta cgacaggaag cacagtccgg    300
ttaccatttg tgacaccgaa aggggatgtt ggttctcgag tttatttgta cgatgaaagt    360
ggtgggcagt atgttctttt taaaccaatc aataaggagt ttacatttga cattgaaacg    420
tcgacgttag cgtgcggaat taatggagca ttgtactttg ttgaaatgga tgctgatggc    480
ggcacttcca atacccacg aaacacggca ggtgcaaagt atggaacggg ctattgtgat    540
gcacaatgtc ccaaagatgg aaagttcatt ggaaataatg ccaacgttgg gcgaaagtat    600
```

```
ggttcctgtt gttttgaatg ggatatttgg gaagctaatg catatgcaac acagtttgcg      660
gctcatccgt gtggtgtttc tacagctgca tatgtttgcc aaagtgactg taatcaatgt      720
gatacgtcag gttgtgcttg gaaccattat cgaattggtg accatgatta ttatgggaag      780
ggtaagaaag ttaacacgaa ttctaaattt acagttgtca ctcagtttat ttctgacaat      840
ggacaagata gtggaaactt gagagaagtt cgacgtttat atgttcaagg tgggaaagtt      900
attgctaata atatcaaaac ttatgttgat tacaagtttg attcgattaa cgatcaatac      960
tgtgatttga caagtggaga tcaagcttat aagcaacgag gaggtgatgg agcgttcacg     1020
aaatcattcc agcgtgggca agttttagca atgtcaattt ggactgatgg cagtatgcaa     1080
tggcttgatg cgggagatgc aggtccgtgc actgatccag gtgggaaaga cgcccttgta     1140
tctgctaata agaatgctta tgttgaatat cgaacatca agtttggtga tattgatacg     1200
acttattaa                                                              1209

<210> SEQ ID NO 116
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
atgctgcttt atattctcac ttttattggt ttaagcttgg ctgaaagtgg aaggaccacc       60
cgttattggg attgctgcaa gggcagctgt gggtgggaaa aaaaagcgaa cgtggacaaa      120
cccattgata catgtgcgaa ggatggaact acaagagttg caagtaatga caccgtgaaa      180
tctggttgtg atggaggtac agggttcatg tgctatgatc agataccatg gcaggtgagt      240
gactcacttt catacggttt tgctgcggct gcttgctgtg gtggtgagag tggtgcttgc      300
tgtggctgct atgaattgac attcacaagt gggccggtta tggaaagaa atgattgtg      360 caaattacaa ataccggtgg tgatctcgga tcaaaccagt tcgatcttgc cattccggga      420 ggtgggggtcg gaatttacaa tggttgcact gcccagtctg gtgcgccttc ggatggttgg      480
ggaagccgat atggaggtgt ttcgtccaga agtgaatgtt ctcaacttcc atcaggtctg      540
caggctggat gccagtggcg attcgattgg ttccagaatg cggacaaccc gagcatcaat      600
ttcagccaag tcagttgccc aagtgagata attgcaaaaa ccaactgcaa ccgtgtctaa      660

<210> SEQ ID NO 117
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
atgttagtgt tcattcttgc attgattctt tctgtgtttg gagacagcgg aagaacaacc       60
cgttattggg attgttgcaa agccagctgt gcgtgggaaa aaaaagctgc tgttacacag      120
cctgttgaca cttgtggaaa agatgggacc acgagagttg cgagcaatga cactgtgaaa      180
tcagcttgtg atggtggaga aggatatatg tgttatgatc aagcaccatg gcagttaat      240 gactctgttg cgtacggttt tgctgctgca gcttgctgtg ggggcgaaag cggagcttgc      300
tgcaattgct atgaacttac attcacgagt ggaccagtga atggaaagaa gatggttgtt      360
caagttacca acaccggtgg tgatcttggc tcgaatcagt ttgatcttgc aattccgggt      420
```

```
ggaggtgttg gtatctacaa cggttgcacc cagcaatcag gtgcacctgc tgatggatgg      480
ggaagccgat atggaggtgt tcatcccgc agcgaatgct ctcagcttcc gtcgggcctt       540
caagctgggt gccaatggag atttgattgg ttccaaaatg ccgataaccc ttcaatcaat      600
ttcaaccaag tgacatgccc tggtgagtta acggcaaaaa ccaattgcaa gcgcacttaa      660

<210> SEQ ID NO 118
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
atgctgcttt atatactcac ttttattagc tggagcgcgg cggaaagtgg caaaaccacc       60
cgctattggg actgctgcaa aggtagctgt gggtgggaaa agaaggccaa tgtggacaag      120
cccattgata catgtgcaaa agatgggacc acgagagttg caagcaatga cacagtcaag      180
tctggttgtg atggtgggac cgggttcatg tgctatgacc agacaccatg gcaagtgagt      240
gactcgcttt catacggttt tgctgcggct gcttgctgtg gtggtgagag tggcgcttgc      300
tgtggctgct atgaattgac attcacaagt gggccggtca atggaaagaa aatgattgtg      360
caaattacaa atactggtgg tgatctcgga tcaaaccagt tcgatcttgc cattccggga      420
ggtggggtcg gaatttacaa tggttgcaca gcccagtctg gtgctccatc agatgggtgg      480
ggaagccgct atggaggcgt gtcatccaga agtgaatgtt ctcagcttcc gtcaggactg      540
caggctggat gccagtggag atttgactgg ttccagaatg ccgacaatcc gaacatcaat      600
ttcaccaatg ttaaatgccc gtctgagatt attgccaaaa ccaattgcaa ccgagtctaa      660

<210> SEQ ID NO 119
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
atgttcatta tttggtgtct tgcttttcg aattttgcaa atctttcgaa tattcaagta        60
aaacgaatca agggagctgt tcaggatca ggaacaacaa caaggtactg ggattgttgc       120
aaaccaagtt gttcatggac aggaaaagct acagtaagta gtccagtcaa gtcttgtgga     180
aaagatggaa gtacagcatc tgttcaagat gagaaatctg gctgtgatgg tggaacttct     240
tacatgtgcg ctaatcaaat tccaagagct gtgaatgatt catatgctat tggttttgca     300
gcagctgcaa tctctggatg gaatgaagct caggcatgct gctcttgcat cgaacttaca    360
ttcacaagtg gcgcagtctc aggtaaaaag ttggtagttc tagtcactaa tactggagga     420
gatcttggaa gtaaccagtt tgacttagca attccaggag gtggtgttgg aatttacaac     480
gcttgcactg atcaatatgg tgctccagct gatggatggg gttctcgata tggtggagtt    540
agttcagccg ctgattgctc tcaacttcct tctgctctcc aatctggctg tagattccga    600
tttgattggt tacaaggtgc tgataaccct ggagtttcat tcaatgaagt tagttgtcca    660
agtgaattga ctggcattac tggttgcaca agagggtag                            699

<210> SEQ ID NO 120
<211> LENGTH: 708
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 120

```
atgctctttg cttgttatct tgcagggacc aactcccttc cgagtgtgaa tggatccaac      60
atccaggtca agcgtatccc taatgcagcc tctggctcag caagaccac cgctattggg     120
actgctggca aacccagctg ctcatggacc ggcaaagcct cagttagcag cccagtgaag    180
tcctgcggaa agacggcag ctcagcctca gttcaggacg agaaatcagg atgcgatggt     240
ggcacttcct acatgtgtgc tgatcaggtc ccacgtgctg tcaatgattc atatgccatc    300
ggtttctcag ctgcagttta cggcggctac aacgaggcag cagcctgctg ctcatgcttc    360
gagcttacat tcaccagcgg cccagtcaat ggcaagaaga tggtcgtcca agttaccaac    420
accggcggag acctcggcag caaccaattc gaccttgcaa tccccggcgg tggggtcggg    480
atttacaacg gctgcacttc ccaatacaac gccggcagcg acggctgggg ctcccgctac    540
ggtggtgtca gctcccgtgc tgactgctcc caactcccat ccgccctcca gggtggctgc    600
caattccact ttgactggtt cggtggcgct gacaatccat cagtcaactt ccaggaagtt    660
tcttgcccga gtgagctcac cgggatcaca ggctgcactc gcaaataa                 708
```

<210> SEQ ID NO 121
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

```
atgttgcttt atattctttg tgtgatcaac tgggtgcttg gagagagtgg cagaacaact      60
cggtattggg attgctgcaa ggccagctgt gcttgggaaa aaaaagcagc tgtaactcag    120
ccagtcgata cgtgtgggaa ggacggaacc acaagagttg ccagcaatga tacagtaaaa    180
tcaagctgtg atggcggaga aggctatatg tgctatgatc aaacaccgtg ggcagtgaac    240
gactcggttg cgtatggatt tgctgctgca gcttgttgtg gtggcgaatc aggagcttgt    300
tgcaattgct atgagcttac attcacaagc ggggcggtta tggaaagaa gatggttgtt    360
caagttacga acactggagg tgatcttggt tcgaatcaat ttgatcttgc gattccggga    420
ggaggcgtcg gaatttataa tggatgcact caacaatctg cgcaccttc ggatggatgg     480
ggaagccgtt atggcggtgt ttcgtctcgt tcggagtgtt ctcagcttcc atcgggtctt    540
caggctggct gccagtggcg ctttgactgg ttccagaatg cggacaaccc ttcaattaac    600
ttcaatcaag tgacatgccc aggtgagctg acagcaaaaa ccaattgcaa gcgtacctaa    660
```

<210> SEQ ID NO 122
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
atgttcttta tttggtgtct tgcttttctcg aattttgcta atctttcgaa tattcaagtg     60
aaacgaatca agggaggtgc ttcaggatca ggaacaacaa cacgtactg ggattgttgt     120
aaaccaagtt gctcgtggac aaaaaaagct gcagtaagta gcccagtaaa atcatgtgga    180
```

```
actgatggaa gcactgcttc tactacagat gagaaatctg gctgtgatgg cggaacttct    240
tacatgtgcg cgaatcagat cccaagagct gtgaacgact cctacgcact tggttttgca    300
gcagcttcaa tctctgggta tgacgagtcc aagtcatgct gtgcttgtat ggaactcaca    360
tttacaggtg gtgcagtttc agggaagaag atggtagttc aagtcactaa cactggagga    420
gatcttggaa gcaaccagtt tgatttagca attcccggag gtggtgttgg aatttataac    480
ggttgcacaa gccaatatgg tgcaccaagt gatggatggg gttctcgata tggtggtgtt    540
gcttcagcat ctgattgttc gcagcttcct tctgctctcc aatctgactg cagattccga    600
tttgactggt tcggaggttc tggcaatcct tcaatttcat tcaacgaagt tagttgtcca    660
agtgaactca ctggcattac tggttgcgtt cgtaattga                           699
```

<210> SEQ ID NO 123
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
atgttgtttt tcgcactatg tctgatcagc tgggtgctgg gagatagcgg caaaacgact     60
cggtattggg attgctgcaa agccagttgc gcgtgggaaa aaaaagctgc tgtgactcaa    120
cctgttgata catgtggaaa agatgggacc acaagggttg ccagtaatga cacagtgaaa    180
tcaagttgtg atgacggaga tggatatatg tgttatgatc aaacaccgtt tgcggtaaat    240
gactcgtatg ccatgggctt tgctgctgca gcttgctgtg gaggcgagtc aggggcttgt    300
tgtggttgtt atgagcttac attcacaagt acagcggttt ctggaaagaa gatggtagtt    360
caaattacca acacggggag tgatcttggc tccaaccagt tcgacctggc cattcctgga    420
ggaggtgttg gaatttataa tggatgcaca aaacagtcgg gggcaccagc agatggatgg    480
ggaagccgat atggaggtgt ttcatctaaa tctgaatgtt cgcaacttcc gtcaggtctt    540
caagctgggt gccaatggcg atttgattgg ttccagaatg ccgacaaccc ttccattaat    600
ttcagttcag tgtcatgccc gggtgagttg acatcaaaaa ccaattgcaa acgcacctaa    660
```

<210> SEQ ID NO 124
<211> LENGTH: 699
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124

```
atgttctttta tttggtgtct tgcttttcg aattttgcta atctttcgaa tattcaagtg     60
aaacgaatca agggaggtgc ttcaggatca ggaacaacaa cacgatactg ggattgttgt    120
aaaccaagtt gctcgtggac aaaaaaagct gcagtaagta gcccagtaaa atcatgtgga    180
actgatggaa gcactgcttc tactacagat gagaaatctg gctgtgatgg cggaacttct    240
tacatgtgcg cgaatcagat cccaagagct gtgaacgact cctacgcact tggttttgca    300
gcagcttcaa tctctgggta tgacgagtcc aagtcatgct gtgcttgtat ggaactcaca    360
tttacaggtg gtgcagtttc agggaagaag atggtagttc aagtcactaa cactggagga    420
gatcttggaa gcaaccagtt tgatttagca attcccggag gtggtgttgg aatttataac    480
ggttgcacaa gccaatatgg tgcacccagt gatggatggg gttctcgata tggtggtgtt    540
```

```
gcttcagcat ctgattgttc gcagcttcct tctgctctcc aatctgactg cagattccga      600
tttgactggt tcggaggttc tggcaatcct tcaatttcat tcaacgaagt tagttgtcca      660
agtgaactca ctggcattac tggttgcgtt cgtaattga                             699
```

<210> SEQ ID NO 125
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

```
atgattcttg cctttgtgat tggagctctg tgcaaagact acagtggaaa tggccagacg       60
actcgttatt gggattgctg taagcccagt tgttcatgga gtaagaaagc tcaggtcagc      120
catgtcgtga actcttgcac tgccagcgga tcgcatgaca cgacagttga tcttaaatcc      180
ggttgtgatg gtggtccttc gtatgtttgc gttgaccaag cgccctgggc cgtcaacagc      240
agctacttca tgggcactgc agcagcggct ctgagtggtg gttctgagtc ggatctttgt      300
tgtcgatgtt ttgagcttac tttcaccagt ggccagtcaa atggtaagaa atgcttgtt       360 caaattacta acacaggttc ggatttgtct ggaaatcaat ttgatttatt gatcccaggt      420
ggcggtgttg gtatctttga tgggtgcagt cggcagtacc caggaggaag ttatgattgg      480
ggtcaacgtt atggtggagt aacatcaaag gctggctgtg ccaagatccc ggctgagctc      540
aaagcaggtt gtgaattccg atttgattat attggcgata acccatccgt cagtttcaag      600
agtgtgcact gccctgacac gatcgtgtca aagaccaact gtcgaaggaa cgacgacacc      660
taa                                                                    663
```

<210> SEQ ID NO 126
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

```
atgtttcttg ctttagtgtt tggagggctt gcgagtactt tgagttatag tggtagtgga       60
cgtactactc gatattggga ttgttgtaag ccaagttgtt catggtccaa aaaagctgca      120
gttagccatg ttgtaaattc atgtactgcc agtggtgaac atgattcaac aactgatctt      180
aaatcaggtt gtgatggtgg tccttcatat gcatgtcctg atcaagctgc ttgggctgtt      240
aattcaagtt atttcatggg aacagcagca gcaacagttg gtcctgaaag tgcaatttgt      300
tgtggttgtt tcgaacttac atttacgagt ggtcaaccat caggtaagaa atggctgtc       360 caaatcacga atactggtgg tgatgttggt ggtggtcaat ttgaccttt aatccctggt       420 ggaggtgttg gtcaatttga tgatgtact cgacagtttg gaataatta tcaatggggt       480 cagcgttatg gtggtgtcac atcagctgct ggatgtagtg gtcttccatc tgctcttcaa      540
gctggttgta agttcaggtt tgattacatt ggtgataatc ctggaattac atataagggt      600
attaagtgcc caagtgaact tactgggaag actggctgtc gcaggaatga cgacgcataa      660
```

<210> SEQ ID NO 127
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

```
atgctgcttg ttttgcttgc tcattcattt agtgccgctg cttattcagg tacagctgca    60
actacatgtt attgggattg ttgtaagatg gcatgttcat ggaattcggc aggtgtgact   120
tctcccccag cttcttgtga tgcgagtggt gcgaagcaag gtggaggaaa cttacaaagt   180
ggttgttcag gtgggacagc ttatgcatgt ccgagtatgg catgttggtc ggttaatgcc   240
tcctttggtt ttggaacagt tgcagctcaa attatgaacg gtggtgcaaa agttcctacc   300
tcacaacttt gctgccgatg ctttgcactt tcgtttacaa gtggtcaagc agcagggaag   360
aagatggttg ttcaagtcac taacgacgga acatacagtg gaaaccactt cgatttcgct   420
gttcctggag gtggagttgg tgaacaaaca aagggatgtt caaagcaatt tccaaatact   480
cctgcatctg cttggggtaa gacttggggt ggtattagta gtgctgccga atgttcaaat   540
ttaccttcca tccttcaaaa tggttgcaag ttccgtttca ctttcggtct gaataaccca   600
agtgccagct tccaaagtgt cccatgtcct ggcgaactca cttcggtcac tggctgtaaa   660
cggactgatg agtaa                                                     675
```

<210> SEQ ID NO 128
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

```
atgtttgttg cctttgtaat tggagctttg tgcaaagatt ttagtgggaa tggtcaaacg    60
actcgctatt gggactgctg taagccaagc tgttcatgga gtaagaaggc gcaagtcagt   120
catgtcgtga actcgtgtaa tgcaaataac cagcatgaca gcactgttga tctcaagtct   180
ggctgtgacg gtggtccttc ctatgcctgc gctgaccaag caccttgggc tgtcaatagc   240
agctatttca tcgggactgc agcagcagcc ttgagtggtg cctcggaggc ggatctgtgc   300
tgcaagtgct ttgagctcac gttcacgagt ggtactccaa acgggcagaa gatgcttgtt   360
caaatcacta acacgggttc ggacttgtct ggaaaccagt tcgacttgct gatccctggt   420
ggtggcgttg gaatctttga tggatgcacg aggcagtacc ctgggagcta tgactggggc   480
cagcgttatg gtggagttac gtcaagagat ggctgcagta agcttccgtc caccctccaa   540
acaggatgcc agttcaggtt tgattacatc ggcgataacc caagcgtcag tttcaagagt   600
acgcactgcc ctgactcaat cgtggggaag accaactgcc gcaggaatga cgatgcataa   660
```

<210> SEQ ID NO 129
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
atgtttcttg cgttggtgtt cggaggtctg gctgggaccg ttggtttgag tggttctgga    60
aagacaactc gatattggga ttgttgtaag ccaagctgtt catggacaaa gaaggcagca   120
gttgatcatg ttgtaaattc atgcactgcg agtggtcaac atgatacaac aacagatctt   180
```

```
aagtcaggtt gtgatggtgg tccttcatat gcttgttttg atcaggctcc ttgggctgtt    240
gactcaagtt atttcatggg tacggcagca gccactgttg cttctgagag tacgatttgc    300
tgtggatgtt ttgaacttac attaccagt ggtcaaccac aaggtaagaa gatgctcgtt     360
caagtcacca atactggcag tgatgttggg aatggtcaat tcgatctttt gattcctggt    420
ggaggtgttg gcattttcga tggatgcagc aaacaattcc ctggtagtta tcagtggggt    480
caacgttatg gtggtgttac cactgcagcg gcttgcagtg gtcttcccac tcaacttcaa    540
gctggttgca agttcaggtt cgattatatt ggtgacaacc ctgccatcac ttacaaagga    600
gtgaaatgtc caactgaaat cactacgaag actggctgcc gtcgcaatga cgatgcttag    660
```

<210> SEQ ID NO 130
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
atgtttcttg cccttgtcgt tggaggactt ggtggtacta caagttatag tgggaatgga     60
cgtaccactc gatattggga ttgttgtaag ccaagttgct catggacaaa gaaggcagca    120
gttgatcatg ttgtaaattc atgcactgct agtggtcaac atgatacaac acctgatctt    180
aagtcaggtt gtgatggtgg tccttcattt aattgctttg accaggctcc ttgggctgtt    240
aactcaagtt acttcattgg aacagcagca gcaacagttg ctgctgaaag tgtaatctgc    300
tgtggttgtt ttgaacttac attcacgagt ggtcttcccc aagggaagaa gatgcttgtt    360
caagttacaa acactggttc agatgtcgga agtggtcaat tcgaccttttt gattccaggt    420 ggaggtgttg gtattttcga tggttgcact aaacaattcc ctggtaatta ccagtggggt    480
caacgttatg gtggtgtgac cacagcagca ggctgcagtg gtcttccaac tcaacttcaa    540
gcaggttgca agttcaggtt tgattacatt ggtgataacc caagcatcaa atatcaaggt    600
gttaaatgtc caacggcaat cactgagaag actggctgcc gtagaaatga tgatcctgcg    660
taa                                                                  663
```

<210> SEQ ID NO 131
<211> LENGTH: 653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
atgttccttg ccttaattgc tggagggctt gcagtcagtg gcactggtcg tacgactcga     60
tattgggatt gttgtaagcc aagctgttca tggagtaaga aagcagcagt taatcatgtt    120
gtgaactcgt gcaatgctaa caatcagcat gatactacga cggatttgaa gtctggttgt    180
gatggtggtc catcatttgc atgtgcagac caagcagctt gggctgttaa ctcaagttat    240
ttcatgggta cggcggcagc aacagttcaa tcagagagtc aaatttgctg tgcatgtttt    300
gaacttacct tcacaagtgg gttgccctca gggaagaaaa tgcttgttca agtgacaaat    360 actgaggtg atgttggaag cggtcaattt gatcttttga tcccaggtgg tggtgttggt    420
caatttgatg ctgcaccaa acaatatcca ggtaattacc agtggggtca acgttatggt    480
ggtgttactt ctgcgtcagc ttgcagtggt ttgccaactg ctcttcaaga aggatgcaag    540
```

```
ttcaggttcg attatattgg tgataacccc acaatgactt acaagagcgt tcttgccca      600 agtgcaatta cttctaagac tggctgcaag cgaaatgatg acactggcgc tta           653
```

<210> SEQ ID NO 132
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
atgtttcttg cgttggtgtt cggaggtctg gctgggaccg ttggtttgag tggttctgga     60
aagacaactc gatattggga ttgttgtaag ccaagctgtt catggacaaa gaaggcagca    120
gttgatcatg ttgtaaattc atgcactgcg agtggtcaac atgatacaac aacagatctt    180
aagtcaggtt gtgatggtgg tccttcatat gcttgttttg atcaggctcc ttgggctgtt    240
aactcaagtt atttcatggg tacggcagca gccactgttg cttctgagag tacaatttgc    300
tgtggatgtt ttgaacttac atttaccagt ggtcaaccac aaggtaagaa gatgctcgtt    360
caagtcacca atactggcag tgatgttggg aatggtcaat cgatcttttt gattcctggt    420
ggaggtgttg gcattttcga tggatgcagc aaacaattcc ctggtagtta tcagtggggt    480
caacgttatg gtggtgttac cactgcagcg gcttgcagtg gtcttccac tcaacttcaa     540 gctggttgca agttcaggtt cgattatatt ggtgacaacc tgccatcac ttacaaagga    600 gtgaaatgtc caactgaaat cactacgaag actggctgcc gtcgcaatga cgatgcttag   660
```

<210> SEQ ID NO 133
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

```
atgtttcttg ctttggtgtt tggagggctt gcgagtactt taagttatag tggtagtgga     60
cgtactactc gatattggga ttgttgtaag ccaagttgct catggtccaa aaaagctgca    120
gttacccatg ttgtaaattc atgcacagcc agtggtgccc atgatacaac aactgatctt    180
aagtcaggtt gtgatggtgg tccttcatat gcttgtcctg atcaagctgc ttgggctgtt    240
aacgcaagtt atttcatggg aacagcagca gcaacagttg gtcctgaaag tgcaatttgt    300
tgtggttgtt tcgaactcac atttacgagt ggtcaaccat caggtaagaa atggctgtc    360 caaatcacta atactggtag tgatgtcggt ggtggtcaat cgacctttt aatccctggt    420 gggggtgttg gtcaatttga tggatgcaca aagcaatttg ggagtaatta ccaatggggt    480
tcacgttatg gtggtgtaac ttctgccgct ggatgcagtg gtcttccaac tgctcttcaa    540
gctggttgta agttcaggtt cgattacctt ggtgataatc tggaatgac atataagggt    600 attaagtgtc caagcgaact gactggaaag actggttgtc gcaggactga tgatgcgtaa   660
```

<210> SEQ ID NO 134
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

-continued

```
atgtttcttg ctttggtgtt tggaggactt gcgagtactt taagttatag tggtagtgga    60
cgtactactc gatattggga ttgttgtaaa ccaagttgtt catggtcgaa aaaagcagca   120
gttaaccatg ttgtcaattc atgcacagcg agtggtgccc atgataccac gactgatctt   180
aaatcaggat gtgatggtgg tccatcatat gcttgtccag atcaagcagc ttgggctgtt   240
aactcaagtt atttcatggg aacagcagca gcaacagttg gtccagaaag tgcaatttgt   300
tgtggttgtt ttgaacttac atttacgaat ggtcaaccat caggtaagaa aatggcagtg   360
caaatcacga atactggtgg tgatgttggt ggtggtcaat ttgatctttt aatccctggt   420
ggaggtgttg gtcaatttga tggctgcaca aagcaatttg gtggtaatta ccaatggggt   480
caacgttatg gtggtgtaac atctgctgct gcatgcagtg gtcttccaac tgctcttcaa   540
gaaggttgta agttcaggtt cgattacatt ggtgataatc ctggaattac atataagggt   600
attaagtgcc caagtgaact tacttcgaag actggttgtc gcaggaatga tgacgcgtga   660
```

<210> SEQ ID NO 135
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135

```
atgattgttg tctttgtgat tggagcccct tgcaaagact atagcggaaa tggccagacg    60
actcgctatt gggactgctg taagccaagc tgctcatgga gcaagaaggc tcaagtcagt   120
catgttgtga actcgtgcaa tgcgaacggg cagcatgaca gtacggttga cctcaagtct   180
ggctgcgacg gcggcccttc ctatgcgtgc actgaccaag cgccttgggc cgtcaacagc   240
agctacttca tgggcacagc ggcagcggcc ctgagcggtg gctcggagtc ggacttgtgc   300
tgcaggtgct ttgagcttac cttcacgagc ggtactccaa acgggaagaa gatgcttgtc   360
caaatcacga acacgggttc agatctgtcc ggaaaccaat tcgatctgct gattcctggt   420
ggtggtgttg gtatctttga tgggtgcacc aggcagtacc ctgggagtta tgactggggc   480
cagcgttatg gcggagtgac gtcgagggat ggctgcagca aaatcccgtc tgcccttcag   540
gcaggctgcc agttccggtt tgattacatt ggcgataacc caagcgtcag tttcaagagt   600
acgcattgcc ctgacacaat cgtgtcgaag accaactgcc gcaggaatga cgaccagtaa   660
```

<210> SEQ ID NO 136
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
atgtttcttg cgtttgtgtt tggaggcctg gctgggaccg ttggtttgag tggttctgga    60
aagacaactc gatattggga ttgttgtaag ccaagttgtt catggacaaa gaaggcagca   120
gttgatcatg ttgtaaattc atgcactgcg agtggtcaac atgatacaac aacagatctt   180
aagtcaggtt gtgatggtgg tccttcatat gcttgttttg atcaggctcc ttgggctgtt   240
aactcaagtt atttcatggg tacggcagca gccactgttg cttctgagag tacaatttgc   300
tgtggatgtt ttgaacttac atttaccagt ggtcaacctc aaggtaagaa gatgctcgtt   360
caagtcacca atactggcag tgatgttggg aatggtcaat tcgatctttt gattcctggt   420
```

```
ggaggtgttg gcattttcga tggatgcagc aaacaattcc ctggtagtta ccagtggggt    480
caacgttatg gtggtgttac ttctgctgcc ggttgcagtg gtcttccac tcaacttcaa     540 gctggttgca agttcaggtt cgattatatt ggtgacaacc ctggaatcac ttacaaagga    600
gtgaaatgtc caactgaaat cactacaaag actggctgcc gtcgcaatga cgatgcttag    660
```

<210> SEQ ID NO 137
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 137

```
atgtttcttg cgttggtgtt tggaggactt gcgagcactt taagttacag tggcagtggg     60
cgtactactc gatattggga ttgttgtaaa ccaagttgtt catggtccaa aaaagctgca    120
gttactcatg ttgtcaattc atgcacagcc agtggtgccc atgatacaac aactgatctt    180
aaatcaggtt gtgatggtgg tccttcgtat gcttgtcccg accaagctgc ttgggctgtt    240
aacgcaagtt atttcatggg aacagcagca gcaacagttg gtcctgaaag tgcaatttgt    300
tgtggttgtt tcgaactcac atttacgagt ggtcaaccat caggcaagaa gatggctgtc    360
caaatcacga atactggcag tgatgttggt ggtggtcaat tgacctttt aatccctggt     420 ggaggtgttg gtcaatttga tggatgcact aagcaatttg ggagtaatta tcaatggggt    480
tcacgttatg gcggtgtaac atcagctgct ggatgcagtg gtcttccaac tgctcttcaa    540
gctggctgta agttcaggtt cgattacctt ggtgacaatc ctggaatgac atataagggc    600
attaagtgcc caagtgaact tactgggaag actggttgtc gcaggactga tgatgcctaa    660
```

<210> SEQ ID NO 138
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 138

```
atgattcttg cctttgtaat tggagctctg tgcaaagact atagtggaaa tggtcaaacc     60
actcgttatt gggattgttg taagccaagt tgttcatgga gtgggaaggc ttcggtcagc    120
catgttgtga actcttgcag tgccgatgga tcgcatgagt cccaacttga tcaaaaatct    180
ggttgtgaag gtggtccttc atatgcgtgt tttgaccaag cagcttgggc cgtcaacagc    240
agttacttta tgggtactgc agcaacagct ttgactggtg gttctgagtc ggatctttgt    300
tgtcgatgtt ttgagcttac ttttactagt ggtcagccaa atggtaagaa aatgcttgtt    360
caaattacca acacgggtac ggatttggct ggaaatgatt ttgatttatt gattcctggt    420
ggtggtgttg gtatgtttga tgggtgcagc cgtcaattcc aggaaaatta cgattggggt    480
caacgttatg gtggagtaac atcaaaggct ggctgtagca agattccggt tgagctgaag    540
gcaggttgtg aattccgatt tgactatatt ggtagtaacc cagctgtcag ttataaaagt    600
gtgcactgtc ctgacgcaat tgtgtcaaag accaactgcc gaaggaatga tgacaactag    660
```

<210> SEQ ID NO 139
<211> LENGTH: 660
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 139
atgtttcttg cgttggtgtt cggaggtctg gctgggaccg ttggtttgag tggttctgga      60
aagacaactc gatattggga ttgttgtaag ccaagctgtt catggacaaa gaaggcagca     120
gttgatcatg ttgtaaattc atgcactgcg agtggtcaac atgatacaac aacagatctt     180
aagtcaggtt gtgatggtgg tccttcatat gcttgttttg atcaggctcc ttgggctgtt     240
aactcaagtt atttcatggg tacggcagca gccactgttg cttctgagag tacaatttgc     300
tgtggatgtt ttgaacttac atttaccagt ggtcaaccac aaggtaagaa gatgctcgtt     360
caagtcacca atactggcag tgatgttggg aatggtcaat tcgatctttt gattcctggt     420
ggaggtgttg gcattttcga tggatgcagc aaacaattcc ctggtagtta tcagtggggt     480
caacgttatg gtggtgttac cactgcagcg gcttgcagtg gtcttcccac tcaacttcaa     540
gctggttgca agttcaggtt cgattatatt ggtgacaacc ctgccatcac ttacaaagga     600
gtgaaatgtc caactgaaat cactacgaag actggctgcc gtcgcaatga cgatgcttag     660

<210> SEQ ID NO 140
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
atgctttcgc ttttcttcat cctttcgatc aaggacatta gcgttcaagt gaaaccgaat      60
gctgtttccg gagatggaag aacaacgcgg tattgggatt gttgcaaacc aagttgtgga     120
tgggatggaa aagcaacggt ttctgcgccg gttgcgtctt gtgacaagaa tggagctaaa     180
cttgcgacat cgaccaaatc aggttgtgat ggtggaacag cttacatgtg ttctaatcag     240
gttccacgag cagttaattc ttcatttgca tatggatttg cagcagcatc gatttcggga     300
tatcaagaag cgcaatcttg ttgtacatgt attttgttga cgttcaagga tacagcagct     360
tcgggtcaga agctcttagt tcaggttacg aacactggtg gagatcttgg atcgaatcaa     420
tttgatttgg ctattccagg tggtggttta ggaatattca ctgatggatg tccagctgag     480
tttgggtcat ggaatggagg ttcacaatat ggtggagtta gttcagcttc gcaatgttcg     540
cagttgcctt cagcacttca gtctggttgt caattccgat ttgattggtt aaaaggagct     600
gataatccgt ctgtttcatt tactgaagtc acttgtccca gcgagttgac tagcattact     660
ggttgcacac gaagataa                                                    678

<210> SEQ ID NO 141
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gttttcccag tcacgac                                                     17
```

-continued

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Lys Arg Gly Gly Gly
1               5

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tttttttttt tttttttttt tttttttttt                                    30

<210> SEQ ID NO 144
<211> LENGTH: 1026
<212> TYPE: DNA
<213> ORGANISM: Unknown
<220> FEATURE:
<223> OTHER INFORMATION: Description of Unknown: Glycosyl hydrolase
      family 7 polynucleotide of a symbiotic protist of Reticulitermes
      speratus
<220> FEATURE:
<221> NAME/KEY: CDS
<222> LOCATION: (1)..(1023)

<400> SEQUENCE: 144

| atg | ttt | aag | gtg | tta | gtc | aaa | gtg | aca | att | gct | ttg | ttt | tgt | ctt | cat | 48 |
|---|---|---|---|---|---|---|---|---|---|---|---|---|---|---|---|---|
| Met | Phe | Lys | Val | Leu | Val | Lys | Val | Thr | Ile | Ala | Leu | Phe | Cys | Leu | His | |
| 1 | | | | 5 | | | | | 10 | | | | | 15 | | |

| gct | gtc | gct | gca | ggg | gaa | cag | cgg | cca | aag | tgg | aca | tgg | gaa | ctt | gat | 96 |
|---|---|---|---|---|---|---|---|---|---|---|---|---|---|---|---|---|
| Ala | Val | Ala | Ala | Gly | Glu | Gln | Arg | Pro | Lys | Trp | Thr | Trp | Glu | Leu | Asp | |
| | | | 20 | | | | | 25 | | | | | 30 | | | |

| gga | aaa | gct | gta | acg | agc | ctt | ata | act | caa | gat | act | gtc | tcc | cgc | gga | 144 |
|---|---|---|---|---|---|---|---|---|---|---|---|---|---|---|---|---|
| Gly | Lys | Ala | Val | Thr | Ser | Leu | Ile | Thr | Gln | Asp | Thr | Val | Ser | Arg | Gly | |
| | 35 | | | | | 40 | | | | | 45 | | | | | |

| aca | aca | gga | aaa | ggt | gat | att | gac | tac | aat | gcg | act | ggt | gtt | ctt | gtc | 192 |
|---|---|---|---|---|---|---|---|---|---|---|---|---|---|---|---|---|
| Thr | Thr | Gly | Lys | Gly | Asp | Ile | Asp | Tyr | Asn | Ala | Thr | Gly | Val | Leu | Val | |
| 50 | | | | | 55 | | | | | 60 | | | | | | |

| tct | gag | gat | ggc | aaa | act | ctc | act | cag | agg | atg | aga | act | atg | acc | aca | 240 |
|---|---|---|---|---|---|---|---|---|---|---|---|---|---|---|---|---|
| Ser | Glu | Asp | Gly | Lys | Thr | Leu | Thr | Gln | Arg | Met | Arg | Thr | Met | Thr | Thr | |
| 65 | | | | 70 | | | | | 75 | | | | | 80 | | |

| tgg | gaa | aat | aaa | tgg | ggc | tct | cgt | ttg | tat | tta | ctc | aac | gct | gat | gga | 288 |
|---|---|---|---|---|---|---|---|---|---|---|---|---|---|---|---|---|
| Trp | Glu | Asn | Lys | Trp | Gly | Ser | Arg | Leu | Tyr | Leu | Leu | Asn | Ala | Asp | Gly | |
| | | | | 85 | | | | | 90 | | | | | 95 | | |

| cag | aat | tat | gag | atg | gtc | gac | ctt | aag | ggc | aaa | gag | tta | gca | ttt | gat | 336 |
|---|---|---|---|---|---|---|---|---|---|---|---|---|---|---|---|---|
| Gln | Asn | Tyr | Glu | Met | Val | Asp | Leu | Lys | Gly | Lys | Glu | Leu | Ala | Phe | Asp | |
| | | | 100 | | | | | 105 | | | | | 110 | | | |

| gtt | gac | atg | tct | gct | ctg | ccc | tgc | agc | att | aat | gcc | gcc | ctg | tac | acc | 384 |
|---|---|---|---|---|---|---|---|---|---|---|---|---|---|---|---|---|
| Val | Asp | Met | Ser | Ala | Leu | Pro | Cys | Ser | Ile | Asn | Ala | Ala | Leu | Tyr | Thr | |
| | | | 115 | | | | | 120 | | | | | 125 | | | |

| gtg | gaa | atg | gcg | aag | ggt | ggt | gcc | tca | aat | gat | gct | cag | tat | gga | aca | 432 |
|---|---|---|---|---|---|---|---|---|---|---|---|---|---|---|---|---|
| Val | Glu | Met | Ala | Lys | Gly | Gly | Ala | Ser | Asn | Asp | Ala | Gln | Tyr | Gly | Thr | |
| | 130 | | | | | 135 | | | | | 140 | | | | | |

| gga | tat | tgt | gat | gca | caa | ggg | tcc | ggg | tcc | ggc | gcc | tgc | aat | gag | ctc | 480 |
|---|---|---|---|---|---|---|---|---|---|---|---|---|---|---|---|---|
| Gly | Tyr | Cys | Asp | Ala | Gln | Gly | Ser | Gly | Ser | Gly | Ala | Cys | Asn | Glu | Leu | |
| 145 | | | | | 150 | | | | | 155 | | | | | 160 | |

```
gac att tgg gaa gca aac agt gca gca acg caa ctt gca gtt cat tct    528
Asp Ile Trp Glu Ala Asn Ser Ala Ala Thr Gln Leu Ala Val His Ser
            165                 170                 175 tgc aca cct gct ggc cgt gga gga acg tgc gac aca ggg ggt tgc aat    576
Cys Thr Pro Ala Gly Arg Gly Gly Thr Cys Asp Thr Gly Gly Cys Asn
        180                 185                 190 gac aat ccg tac agg act gat aag act ttc tac ggt tca tca gag aaa    624
Asp Asn Pro Tyr Arg Thr Asp Lys Thr Phe Tyr Gly Ser Ser Glu Lys
    195                 200                 205 ttt gct gtt gac acc tcc aaa cca ttt acc gta gta act cag ttt gtg    672
Phe Ala Val Asp Thr Ser Lys Pro Phe Thr Val Val Thr Gln Phe Val
210                 215                 220 acc ggt gcc ggt ggt gcg ttg act gag gtc atc cgt acg tat gtg cag    720
Thr Gly Ala Gly Gly Ala Leu Thr Glu Val Ile Arg Thr Tyr Val Gln
225                 230                 235                 240 ggt gga aag acc atc ccc act ccc gca gtc act gct ggc ggc aac caa    768
Gly Gly Lys Thr Ile Pro Thr Pro Ala Val Thr Ala Gly Gly Asn Gln
            245                 250                 255 tac aca tcc ctc acg aac gcg tac tgc agc gct tca ggc ggg aaa ccg    816
Tyr Thr Ser Leu Thr Asn Ala Tyr Cys Ser Ala Ser Gly Gly Lys Pro
        260                 265                 270 ctt gat ggc atg agc acg tcc ctg gac gct ggc cac gtg ata gtg gtt    864
Leu Asp Gly Met Ser Thr Ser Leu Asp Ala Gly His Val Ile Val Val
    275                 280                 285 tcg ctg tgg gca tcg gac gat gca ggg gga atg gac tgg ctg gac agt    912
Ser Leu Trp Ala Ser Asp Asp Ala Gly Gly Met Asp Trp Leu Asp Ser
290                 295                 300 ggg aac aac gga ccg tgc gct gcg aac gat cct gac gga gca agg gag    960
Gly Asn Asn Gly Pro Cys Ala Ala Asn Asp Pro Asp Gly Ala Arg Glu
305                 310                 315                 320 cag ctg atc aag aag tac cct gag gca ctg gtc aag tat tcg aat ttg   1008
Gln Leu Ile Lys Lys Tyr Pro Glu Ala Leu Val Lys Tyr Ser Asn Leu
            325                 330                 335 agg atc acc acg ttg taa                                           1026
Arg Ile Thr Thr Leu
            340

<210> SEQ ID NO 145
<211> LENGTH: 341
<212> TYPE: PRT
<213> ORGANISM: Unknown
<220> FEATURE:
<223> OTHER INFORMATION: Description of Unknown: Glycosyl hydrolase
      family 7 polypeptide of a symbiotic protist of Reticulitermes
      speratus

<400> SEQUENCE: 145

Met Phe Lys Val Leu Val Lys Val Thr Ile Ala Leu Phe Cys Leu His
1               5                   10                  15

Ala Val Ala Ala Gly Glu Gln Arg Pro Lys Trp Thr Trp Glu Leu Asp
            20                  25                  30

Gly Lys Ala Val Thr Ser Leu Ile Thr Gln Asp Thr Val Ser Arg Gly
        35                  40                  45

Thr Thr Gly Lys Gly Asp Ile Asp Tyr Asn Ala Thr Gly Val Leu Val
    50                  55                  60

Ser Glu Asp Gly Lys Thr Leu Thr Gln Arg Met Arg Thr Met Thr Thr
65                  70                  75                  80

Trp Glu Asn Lys Trp Gly Ser Arg Leu Tyr Leu Leu Asn Ala Asp Gly
                85                  90                  95

Gln Asn Tyr Glu Met Val Asp Leu Lys Gly Lys Glu Leu Ala Phe Asp
            100                 105                 110
```

-continued

```
Val Asp Met Ser Ala Leu Pro Cys Ser Ile Asn Ala Ala Leu Tyr Thr
        115                 120                 125

Val Glu Met Ala Lys Gly Gly Ala Ser Asn Asp Ala Gln Tyr Gly Thr
    130                 135                 140

Gly Tyr Cys Asp Ala Gln Gly Ser Gly Ser Gly Ala Cys Asn Glu Leu
145                     150                 155                 160

Asp Ile Trp Glu Ala Asn Ser Ala Ala Thr Gln Leu Ala Val His Ser
                165                 170                 175

Cys Thr Pro Ala Gly Arg Gly Gly Thr Cys Asp Thr Gly Gly Cys Asn
            180                 185                 190

Asp Asn Pro Tyr Arg Thr Asp Lys Thr Phe Tyr Gly Ser Ser Glu Lys
            195                 200                 205

Phe Ala Val Asp Thr Ser Lys Pro Phe Thr Val Val Thr Gln Phe Val
    210                 215                 220

Thr Gly Ala Gly Gly Ala Leu Thr Glu Val Ile Arg Thr Tyr Val Gln
225                     230                 235                 240

Gly Gly Lys Thr Ile Pro Thr Pro Ala Val Thr Ala Gly Gly Asn Gln
                245                 250                 255

Tyr Thr Ser Leu Thr Asn Ala Tyr Cys Ser Ala Ser Gly Gly Lys Pro
            260                 265                 270

Leu Asp Gly Met Ser Thr Ser Leu Asp Ala Gly His Val Ile Val Val
        275                 280                 285

Ser Leu Trp Ala Ser Asp Ala Gly Gly Met Asp Trp Leu Asp Ser
    290                 295                 300

Gly Asn Asn Gly Pro Cys Ala Ala Asn Asp Pro Asp Gly Ala Arg Glu
305                     310                 315                 320

Gln Leu Ile Lys Lys Tyr Pro Glu Ala Leu Val Lys Tyr Ser Asn Leu
                325                 330                 335

Arg Ile Thr Thr Leu
            340
```

POLYNUCLEOTIDE ENCODING A CELLULASE ENZYME AND METHOD FOR PRODUCING THE ENZYME

CROSS-REFERENCE TO RELATED APPLICATIONS

The present application is a 35 U.S.C. §371 National Stage patent application of International patent application PCT/JP2008/051027, filed on Jan. 18, 2008, which claims priority to Japanese patent application JP 2007-053122, filed on Mar. 2, 2007.

TECHNICAL FIELD

The present invention relates to novel cellulase enzymes and a method for producing the same. The enzymes are mainly from intestinal symbiotic protists of Termitidae.

BACKGROUND ART

Cellulose is a high molecular polysaccharide in which glucose molecules have been linked by β-1,4-glucoside linkage. Thus, hydrolysis of cellulose can produce glucose and so the cellulose can be effectively used as a glucose source. A substance that efficiently degrades cellulose and plays a key role in a series of reactions to extract the energy therefrom is cellulase.

Many cellulases have been isolated from fungi or bacteria. Cellulose is a less degradable substance, and degradation of cellulosic biomass by cellulase and utilization thereof are highly problematic, in terms of realization of practical applications thereof. Accordingly, elucidation of properties of such enzyme and efficient production of such enzyme are important themes associated with effective utilization of cellulase resources.

The intestinal symbiotic protists of termites were known to degrade cellulose with very high efficiency. However, such symbiotic protists were hard to culture, and there has not been progress with the analysis thereof for this reason. Even in recent years, only a small amount of research has been conducted on symbiotic protists and cellulases thereof.

In Japanese Patent Publication (kokai) No. H11-46764 A (1999) and in Watanabe, H., Noda, H., Tokuda, G., and Lo. N., 1998, Nature 394: 330-331, for example, cellulases produced by two types of termites (i.e., *Reticulitermes speratus* and *Nasutitermes takasagoensis*) are disclosed, although they are not derived from the symbiotic protists of termites. Such cellulases have a molecular weight of 40,000 to 50,000, thermostability of 60° C. or lower, an optimal pH of 5.0 to 6.0, and a specific activity on carboxy cellulose of 70 to 1,300 units/mg. The term "1 unit" used herein refers to the amount of an enzyme that generates a reducing sugar equivalent to 1 μmol of glucose per minute. The same definition applies hereinafter.

Japanese Patent Publication (kokai) No. 2003-70475 A discloses a protein having activity of cellulase derived from the symbiotic protists of *coptotermes* (*Spirotrichonympha leidyi*), which has a molecular weight of approximately 36 kDa, optimal pH 6.0, Vmax 148.2 units/mg, and Km 1.9 mg/ml.

Furthermore, the present inventors have made a report regarding evolution of the lignocellulose degrading system via a comprehensive technique based on detection of symbiotic bacteria, the transcription regulatory mechanism, molecular evolution of symbiotic organisms (i.e., Oxymondas), and EST analysis of the protists of termites (the Journal of the Japanese Society for Extremophiles, Vol. 4, No. 2, O-13, P-12 to P-15, 2005 (Jp)).

DISCLOSURE OF THE INVENTION

Wood is the only nutritional source of the symbiotic protists of termites, and such symbiotic protists efficiently degrade cellulosic biomass. Although such symbiotic protists are deduced to have efficient cellulase genes accordingly, there exist very few examples of such genes having been obtained.

Under such circumstances, the object of the present invention is to provide a novel cellulase from the symbiotic protists which are derived from certain termites and roaches and DNA encoding the same.

Another object of the present invention is to provide an expression system that expresses DNA encoding the cellulose, and to provide a method for producing such cellulase using the expression system.

SUMMARY OF THE INVENTION

In summary, the present invention includes the following features.

In the first aspect, the present invention provides a cellulase enzyme derived from intestinal symbiotic protists of insects selected from the group consisting of *Reticulitermes speratus*, *Hodotermopsis sjostedti*, *Neotermes koshunensis*, *Mastotermes darwiniensis*, and Cryptocercidae and comprising an amino acid sequence encoded by a nucleotide sequence selected from the group consisting of the nucleotide sequences as shown in SEQ ID NOS:1 to 140 and nucleotide sequences having 90% or higher identity therewith, a mixture of two or more such enzymes, and a processed matter of such an enzyme or mixture.

According to an embodiment of the present invention, the processed matter is an extract, a lyophilized product, a partially or completely purified product, or an immobilized product, of the enzyme.

According to another embodiment of the present invention, the cellulase enzyme is either endoglucanase or cellobiohydrolase.

In the second aspect, the present invention provides a DNA encoding the cellulase enzyme as defined above.

According to an embodiment of the present invention, the DNA comprises a nucleotide sequence selected from the group consisting of the nucleotide sequences as shown in SEQ ID NOS:1 to 140 and nucleotide sequences having a 90% or higher identity therewith.

In the third aspect, the present invention provides a vector comprising one or a plurality of DNAs as defined above.

According to an embodiment of the present invention, the vector further comprises a promoter that regulates expression of the DNA.

In the fourth aspect, the present invention provides a transformed cell comprising the vector as defined above.

According to an embodiment of the present invention, the transformed cell is a koji mold cell.

According to another embodiment of the present invention, the koji mold is *Aspergillus oryzae*.

In the fifth aspect, the present invention provides a method for producing a cellulase enzyme comprising culturing the transformed cell as defined above in a medium and recovering proteins of one or a plurality of cellulase enzymes as defined above from the cell or medium alone or in admixture.

DEFINITION

The terms used herein pertinent to the invention include the following meanings.

The term "intestinal symbiotic protists" as used herein refers to protists that live symbiotically in the intestinal tract of *Reticulitermes speratus, Hodotermopsis sjostedti, Neotermes koshunensis, Mastotermes darwiniensis*, or Cryptocercidae.

The term "identity" as used herein represents the degree of coincidence between two sequences when two different amino acid sequences or nucleotide sequences are aligned and compared with or without introduction of a gap(s). In general, the degree of coincidence is a percentage (%) of the number of identical amino acids (or the number of identical nucleotides) relative to the total number of amino acids (or the total number of nucleotides). The search of sequence identity search can be generally carried out via conventional algorisms such as BLAST (e.g., BLASTX or BLASTN), FASTA, FASTX, or TFASTA (e.g., Toshihisa Takagi and Minoru Kanehisa (ed.), the Usage of GenomeNet Databases, Kyoritsu Shuppan, Tokyo, Japan, 1998).

The term "processed matter" as used herein refers to an enzyme of an arbitrary form that is obtained during a process for purifying or processing the enzyme of the present invention. Examples of processed matters include enzymes in the form of an enzyme extract from an enzyme source, a partially or completely purified enzyme, a lyophilized product of an enzyme, and an immobilized enzyme that is obtained via processing, such as via immobilization of an enzyme on a support.

This description includes all or part of the contents as disclosed in the description and/or drawings of Japanese Patent Application No. 2007-53122, which is a priority document of the present application.

BRIEF DESCRIPTION OF THE DRAWINGS

FIG. 3 shows optimal pH and temperature profiles of the purified cellulase (Rs2038B-11; encoded by the nucleotide sequence of SEQ ID NO: 79).

FIG. 4 shows the results of comparison of specific activity, optimal pH, temperature, Km, and Vmax of the purified cellulase (Rs2038B-11; encoded by the nucleotide sequence of SEQ ID NO: 79) (host: *Reticulitermes speratus*) with a known cellulase.

BEST MODES FOR CARRYING OUT THE INVENTION

Figure 1:
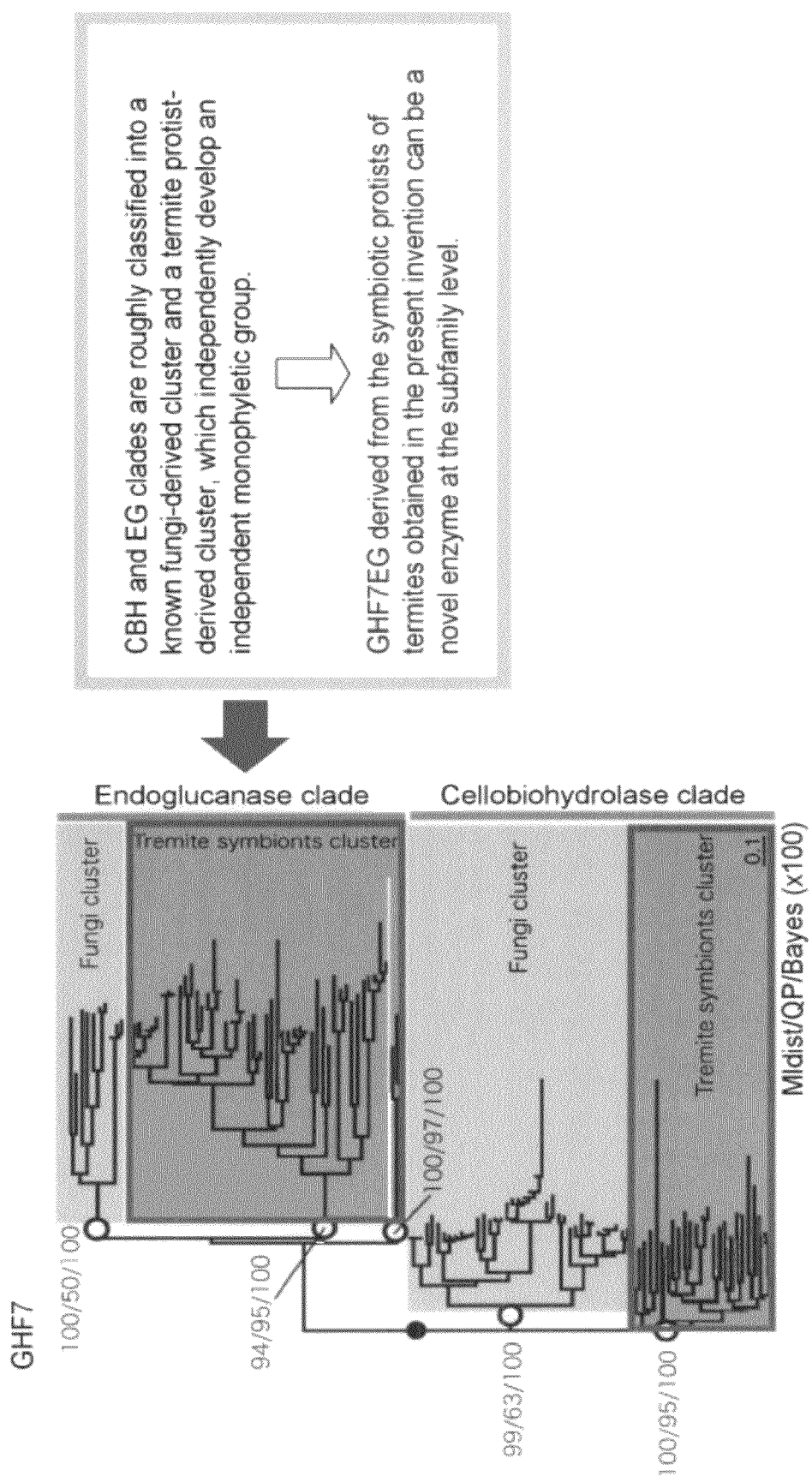
FIG. 1 shows verification of the novelty of the enzyme of the present invention, GHF7, based on a molecular dendrogram.

1. Cloning and Sequencing of Cellulase Gene

Insects employed as cellulase sources of the present invention were lower termites; i.e., *Reticulitermes speratus, Hodotermopsis sjostedti, Neotermes koshunensis*, and *Mastotermes darwiniensis*, and progenitors thereof, i.e., Cryptocercidae. Such insects eat wood, such as a rotten fallen tree or dead branch, wherein the wood is saccharized by the cellulose degrading activity of symbiotic protists and the saccharides become a nutritional source of the insects. Since most hydrolytic enzymes of protists are glycosyl hydrolases, the enzymes obtained from the protists of interest are expected to be very useful for saccharification of ligneous biomass.

Cloning and sequencing of the cellulase genes can be performed in the following manner.

At the outset, the intestinal tracts are removed from the insects, fractured, and then subjected to low-speed centrifugation at approximately 100×g to obtain protist fractions. Total RNA is isolated from the resulting fractions in accordance with a conventional technique, mRNA is obtained using an oligo dT-connected column, RNA-DNA hybrid molecules are synthesized from mRNA using an oligo dT primer and a reverse transcriptase, a nick is introduced into the RNA strand using RNase, DNA synthesis is initiated from the nick using a DNA polymerase, the RNA fragment is substituted with a DNA fragment, and the nick is repaired by DNA ligase to synthesize double-stranded cDNA. The thus-obtained cDNA molecules then undergo end extension using a terminal transferase. Alternatively, a restriction enzyme site is bound to each end of the cDNA molecule, the resultant is inserted into a plasmid, phage, or other vector, and the vector is introduced into bacteria such as *E. coli* via transformation, followed by amplification. Thus, a cDNA library is obtained.

A target clone can be selected from the library via, for example, hybridization comprising forming a phage plaque and transferring the same to a nitrocellulose filter to obtain a replica filter. The selection of a DNA clone of interest can be carried out by detecting it on the replica filter by hybridization using a probe, which has been labeled with a label such as radioactive or fluorescent label, comprising a sequence complementary to the target DNA. Alternatively, when the library is prepared using an expression vector, the selection of a DNA clone of interest may be carried out by translating to fusion proteins with a reporter protein, such as β-galactosidase, followed by detecting a protein encoded by the DNA clone by means of an immunological procedure using an antibody to the reporter protein or to the protein of interest. Such technique is effective when a partial amino acid sequence of the target protein or a sequence highly homologous thereto is known in advance. After the target clone is selected, a DNA fragment is inserted into an adequate cloning vector, amplified, cleaved with a restriction enzyme, exonuclease, recycled with ligase, and sequenced using universal sequencing primers (USPs). A complete sequence can then be determined by linking overlapping sequences. Alternatively, single-stranded DNA is partially amplified via PCR with the use of the USP primer, a second primer for a partial sequence overlapping with the amplified product is used for partial amplification, and the third primer for a partial sequence overlapping with the amplified product is further used for amplification. Where necessary, PCR amplification may further be carried out with the use of fourth, fifth, and other primers, the amplification products thereof may be sequenced, and the overlapping sequences may be linked to determine the complete sequence.

Single pass sequencing may be carried out as an alternative sequencing technique to determine the sequence of the target protein. Colonies are randomly selected from the thus-obtained cDNA library, the selected colonies are cultured in a selection medium for bacteria (e.g., LB medium containing an antibiotic such as kanamycin), plasmids are isolated with the use of a commercially available plasmid purification system, the single pass sequence at the 5' end or the 3' end is determined, and the obtained sequence is subjected to homology analysis and annotation with respect to known sequences by accessing public databases such as the NCBI database (e.g., GenBank and UniGene, U.S.A.) with the utilization of a homology search algorism, such as FASTA or BLAST, in order to select a sequence that is deduced to be equivalent to cellulase. Further, genes corresponding to endoglucanase of the glycosyl hydrolase family 7 (GHF7) are selected from among the thus-selected cellulase gene homologues, and lineage analysis of partial sequences is performed to select sequences that originate from the common progenitors (having a 80% or higher amino acid sequence homology).

By the above-described procedures, 140 novel cellulase genes from the symbiotic protists of four termites and one roach have now been found; i.e., specifically, 43 clones (SEQ ID NOS:1 to 43) for glycosyl hydrolase family 5 (GHF5), 34 clones (SEQ ID NOS:44 to 77) for GHF7 cellobiohydrolase (CBH), 38 clones (SEQ ID NOS:78 to 115) for GHF7 endoglucanase (EG), and 25 clones (SEQ ID NOS:116 to 140) for GHF45, have now been found as novel cellulase genes.

Accordingly, the present invention includes a DNA encoding a cellulase enzyme comprising the nucleotide sequence as shown in any of SEQ ID NOS:1 to 140.

Further, the present invention includes a DNA encoding a cellulase enzyme comprising a nucleotide sequence which has a 90% or higher identity with the nucleotide sequence as shown in any of SEQ ID NOS:1 to 140. Such DNA encoding a highly homologous cellulase enzyme can be obtained by, for example, naturally occurring mutation, such as mutation or alternative splicing, or artificially. Alternatively, such DNA may be obtained in the form of a cellulase gene homologue, which has a different sequence derived from a family, species, or strain that is different from those of termites or roaches. The mutation is a substitution, deletion, insertion, or addition of a nucleotide(s), or a combination thereof. Proteins that have 80% or higher, 85% or higher, 90% or higher, preferably 93% or higher, more preferably 95% or higher, and further preferably 98% or higher sequence identity with the nucleotide sequence as shown in any of SEQ ID NOS:1 to 140 and that are obtained by expression of mutation genes, should have cellulase activity.

The above-described mutant can be separated or isolated via hybridization under stringent conditions in which DNA comprising the nucleotide sequence as shown in any of SEQ ID NOS:1 to 140, a sequence complementary thereto, or a fragment thereof is used as a probe (e.g., about 20 nucleotides or more, preferably 30 nucleotides or more, and more preferably 50 nucleotides or more, such as 50 to 100 nucleotides). Under stringent conditions, for example, hybridization is carried out at about 45° C., and washing is then carried out one or more times in 0.2° SSC and 0.1% SDS at 50° C. to 65° C. Alternatively, hybridization is carried out in 6" SSC at 42° C. and washing is then carried out in 0.1° SSC and 0.1% SDS at 55° C. Also, formamide may be added to a buffer. Hybridization conditions are described in, for example, Ausubel et al., 1990, Current Protocols in Molecular Biology, John Wiley & Sons, Inc. (U.S.A.).

Alternatively, the cDNA libraries from organism samples that are deduced to contain said mutants may be subjected to polymerase chain reaction (PCR) using the sense and antisense primers (generally 15 to 30 nucleotides) prepared based on the nucleotide sequences as shown in SEQ ID NOS:1 to 140, the mutant DNAs of interest can then be amplified and further purified by a technique such as agarose gel electrophoresis or polyacrylamide gel electrophoresis.

Further, mutation can be artificially introduced into the sequence of interest by, for example, site-directed mutagenesis or a method involving preparing primers comprising mutations and performing PCR using, as templates, vectors each containing the nucleotide sequences as shown in SEQ ID NOS:1 to 140.

The present invention also includes a cellulase enzyme comprising an amino acid sequence encoded by a nucleotide sequence selected from the group consisting of the nucleotide sequences as shown in SEQ ID NOS:1 to 140 and nucleotide sequences having a 90% or higher identity therewith. All nucleotide sequences as shown in SEQ ID NOS:1 to 140 represent the cellulase gene sequences between the start codons and the stop codons. If nucleotides are replaced by the corresponding amino acids in accordance with the genetic codes of the genetic code dictionary, the resulting nucleotide sequence is converted into the amino acid sequence which corresponds to the nucleotide sequence as shown in each SEQ ID number. Specifically, the cellulase enzyme of the present invention has a cellulose degrading activity and comprises the amino acid sequence corresponding to the nucleotide sequence shown in any of SEQ ID NOS:1 to 140.

According to a further embodiment, the cellulase enzyme is endoglucanase (EG) or cellobiohydrolase (CBH).

Endoglucanase (EC 3.2.1.4) is a hydrolytic enzyme that cleaves β-1,4-glucoside linkages of cellulose or the like in an endo-form, i.e. that cleaves said linkages from the inside of the molecule.

Cellobiohydrolase (EC 3.2.1.91) is a hydrolytic enzyme that cleaves β-1,4-glucoside linkages of cellulose or the like from either reducing terminus or non-reducing terminus to generate cellobiose.

Among sequences shown in SEQ ID NOS:1 to 140, sequences encoding CBH activity are those shown in SEQ ID NOS:44 to 77, and other sequences encode EG activity.

An enzyme containing the above-described mutation, which falls within the scope of the cellulase enzyme of the present invention, has 80% or higher, or 85% or higher, preferably 90% or higher, preferably 93% or higher, more preferably 95% or higher, and so more preferably 98% or higher sequence identity with an amino acid sequence encoded by a nucleotide sequence as shown in any of SEQ ID NOS:1 to 140, and has a cellulase activity.

Such mutation is a deletion, substitution, insertion, or addition of one or more amino acids, preferably one or several amino acids, or a combination thereof. Especially, the preferable substitution of an amino acid(s) is a conservative amino acid substitution, and non-conservative substitution is also acceptable, provided that cellulase activity is not adversely affected. Conservative substitution is carried out between amino acids that have a similar property in terms of the amino acid structure, charge, polarity (or hydrophobicity), or other property. Examples of the conservative amino acid substitution include a substitution between basic amino acids, such as Arg, Lys, and His, a substitution between acidic amino acids, such as Asp and Glu, a substitution between aromatic amino acids, such as Trp, Phe, and Tyr, a substitution between hydrophobic amino acids, such as Leu, Ile, Val, Ala, Met, and Pro, and a substitution between polar amino acids, such as Ser, Thr, Gly, Asn, and Gln.

2. Cellulase Expression System

A DNA encoding a cellulase enzyme comprising a nucleotide sequence selected from those shown in SEQ ID NOS:1 to 140, which were cloned and sequenced by the method described in item 1 above, or a DNA encoding a cellulase enzyme comprising a nucleotide sequence having 80% or higher, or 85% or higher, and preferably 90% or higher sequence identity with any of the above nucleotide sequences, may be inserted into an expression vector, and the resultant may be used to transform or transfect it into a competent cell to obtain a transformed cell.

The DNA may comprise one or a plurality (for example, two or more, 3 or more, 4 or more, or 5 or more) of cellulase genes having different sequences tandemly ligated to a vector in an expressible manner. An expression system comprising the DNAs enables generation of a plurality of cellulases at the same time.

An expression vector can comprise, for example, a control sequence(s) such as a promoter, an enhancer, a replication origin, a ribosome binding site, an SD sequence, or a terminator; a selection marker sequence, such as an antibiotic-resistant gene sequence or a complementary auxotrophic sequence; or the like. In general, the type of such vector can be changed depending on the host cell to be transformed. Examples of such vector include vectors for prokaryotic organisms such as *E. coli, Bacillus subtilis*, and *Pseudomonas*, and vectors for eukaryotic organisms such as yeast, fungi (e.g., filamentous fungi or basidiomycete), and animal cells (e.g., insect cells or mammalian cells). The vectors include plasmid, phage, and virus vectors, for example.

Because the vectors are commercially available, such commercially available vectors can be used. Examples of bacterial vectors include pET3 and pET11 (Stratagene) and pMAL (New England Biolabs). Also, promoters such as trp promoter, lac promoter, $P_L$ promoter, and $P_R$ promoter can be used as regulatory sequences, for example. Examples of yeast vectors include pYEUra3, YEp13, and YCp50. Also, promoters such as GAL1 promoter, GAL10 promoter, and glycolytic enzyme promoters can be used as regulatory sequences. An example of fungal vectors for *Aspergillus* is pNAN8142. Also, promoters such as amylase gene (amyB) promoter and glucoamylase gene (glaA) promoter can be used as regulatory sequences.

Examples of host cells that can be used include: bacteria cells such as *E. coli, Pseudomonous, Streptomyces, Bacillus subtilis, Streptococcus*, and *Staphylococcus*; yeast cells; fungal cells such as *Aspergillus*; insect cells such as *Drosophila* S2 and *Spodoptera* Sf9; and animal cells, such as CHO cells, COS cells, HeLa cells, C127 cells, 3T3 cells (including mutant strains with deficient dihydrofolate reductase or thymidine kinase), BHK21 cells, and HEK293 cells. Where necessary, host cells in which endogenous genes that inhibit target DNA expression or protein production have been disrupted can be used. Genetic disruption can be carried out by, for example, the known antisense RNA method (i.e., which is a method comprising introducing DNA encoding RNA complementary to mRNA of the target gene into the cell genome via homologous recombination) (e.g., C. Helene and J. J. Toulme, Biochem. Biophys., Acta, 1990, 1049: 99-125). An antisense molecule forms a base pair with mRNA and inhibits the protein translation from mRNA. According to a preferable embodiment of the present invention, the preferred hosts are koji mold (e.g., *Aspergillus oryzae*), a protease-disrupted strain of the koji mold, and the like.

Examples of the transformation or transfection include calcium phosphate transfection, DEAE-dextran-mediated transfection, microinjection, cationic lipid-mediated transfection, electroporation, genetic transduction, the spheroplast method, and infection (e.g., virus or phage infection).

The expression plasmids used as examples in the Examples below were constructed by inserting said DNA between the α-amylase promoter (amyB)—the structural gene and the terminator T-amyB sequence of the α-amylase gene on the entry vector (pDESTR3-R4) via recombination using the Gateway system (Invitrogen) and using the resultant to transform koji mold. With the addition of the KRGGG (SEQ ID NO: 142) sequence between the structural gene sequence and the DNA of interest, an expression plasmid was constructed so as to cleave the protein of interest from amylase.

3. Production of Cellulase

Host cells transformed by a vector that enables the expression of DNA encoding the cellulase of the present invention are cultured in an adequate culture medium, and the DNA is expressed in the host cells, thereby producing cellulase.

Medium is adequately selected depending on a host cell. Commercially available natural and synthetic media can be used. Alternatively, a medium containing a carbon source, a nitrogen source, inorganic salts, blood serum, cytokines, vitamins, and the like may be prepared in accordance with the description of a literature. A medium can optionally comprise an antibiotic such as tetracycline or ampicillin, an inducer such as isopropyl-β-D-thiogalactopyranoside (IPTG), or the like.

Culture can be conducted under aerobic or anaerobic conditions and agitation, shake, or static culture conditions, for example, generally at a temperature from room temperature to 40° C.

In the case of the culture using koji mold as a host, for example, 100 ml of a nutritional medium containing maltose or dextrin is placed into a 500-ml Erlenmeyer flask, into which the constructed koji mold strain is seeded. The strain can be cultured at 30° C. for 4 days thereby inducing an expressed protein which is released into a medium.

The cellulase protein of the present invention can be recovered from the cultured transformed cell or medium. When an eukaryotic cell is used as a host, a fusion DNA comprising DNA of the present invention and DNA encoding the signal sequence ligated thereto is prepared, and the cell is transformed with the fusion DNA. Thus, the target protein can be secreted outside the cell, i.e. into the medium. When a prokaryotic cell is used as a host cell, in general, the protein of interest is accumulated in the cell. Thus, the cell may be disrupted by a method of changing the osmotic pressure, a mechanical technique (e.g., an ultrasound technique), or other means that disrupts the cell, and the protein of interest can be recovered from the extract.

The cellulase protein of the present invention can be purified via conventional techniques. Examples of such techniques include precipitation or fractionation with ammonium sulfate or ethanol, extraction with an acid or organic solvent, chromatographies such as anion- or cation-exchange chromatography, gel filtration chromatography, hydrophobic interaction chromatography, affinity chromatography, hydroxyl apatite chromatography, and reversed-phase high-performance liquid chromatography, and polyacrylamide gel electrophoresis, for example. Such technique can be carried out alone or in adequate combination.

Cellulase enzyme activity can be assayed in the following manner.

Endoglucanase activity can be assayed in the following manner. To 10 μl of the protein sample, 250 μl of 1% carboxymethyl cellulose (dissolved in 0.1M sodium acetate buffer (pH 6.0)) is added, and the reaction is carried out at room temperature for 1 hour. In order to assay the generated reducing sugar, 1 ml of the tetrazolium blue reagent is added to 100 μl of the reaction solution of 260 μl, the reaction is carried out in boiled water for 10 minutes, cooled, and assayed for absorbance on spectrophotometer (O.D. 660) (Jue, C. K. and Lipke, P. N., "Determination of reducing sugars in the nanomole range with tetrazolium blue," J. Biochem Biophys Methods, 11, 109-115, 1985).

Cellobiohydrolase activity can be assayed in the same manner, except that Avicell is used instead of carboxymethyl cellulose as a substrate.

The cellulase enzyme of the present invention can exist in various forms of processed matter. Examples of such processed matter include an extract, a lyophilized product, a partially or completely purified product, and an immobilized product, of an enzyme. Specific examples include enzymes in the form of an enzyme extract from an enzyme source, a partially or completely purified enzyme, a lyophilized product of an enzyme, and an immobilized enzyme that is obtained via processing, such as immobilization of an enzyme on a support.

Examples of the methods for immobilization of an enzyme include a carrier attaching method, which is a method comprising attaching an enzyme to a water-insoluble carrier covalently or non-covalently, and an entrapment method which is a method comprising entrapping an enzyme in a fine lattice of a polymer gel (e.g., Saburo Fukui (ed.), Kouso kougaku (enzyme engineering), Tokyo Kagaku Dojin, Tokyo, Japan, 1981). Examples of carriers include porous polymers, ion-exchange resins, glass, minerals, and metals (e.g., iron oxide). Examples of polymer gels include polysaccharides (e.g., carragheenan) and photo-curing resins. Enzymes that are immobilized on/in such carriers or polymer gel may be filled into a column or the like and used for continuous cellulose degradation.

A cellulase that is suitable for an intended application is selected from among many cellulases, such cellulases are used alone or in admixture, and such cellulase can be used as an enzyme source for advanced glycosylation of ligneous biomass, alcohol production, and production of biopolymers or as a main or auxiliary component of a detergent, a preparation for fiber processing, a feed additive, a digestive aid, a biopolymer, and the like. Such substances can be used in combination without particular limitation, and two or more, preferably 5 or more, and further preferably 10 or more thereof can be used in combination.

EXAMPLES

The present invention is described in greater detail with reference to the following examples, although the technical scope of the present invention is not limited thereto.

Example 1

Isolation of mRNA

The intestinal tracts were extracted from *Reticulitermes speratus, Hodotermopsis sjostedti, Neotermes koshunensis, Mastotermes darwiniensis*, and Cryptocercidae, the extracted intestinal tracts were individually disrupted in Solution U (Trager 1934, Biological Bulletin, Vol. 66: 182-190), and the resultants were filtered through a 100-micron nylon mesh. The obtained suspension was mildly centrifuged at 100×g for 3 minutes to obtain protists fractions. The fractions were washed three times with Solution U to obtain protists fractions for RNA extraction. mRNA was isolated in accordance with the instructions of Oligo-dT30<Super™> (SEQ ID NO: 143) (Roche, Japan), from protists of the host termites.

Example 2

Construction of cDNA Library 2-3 μg mRNA, which was prepared from the symbiotic protists of the termites, was used to construct a cDNA library. A *Reticulitermes speratus* library was constructed in accordance with the method of Piero et al. (Carninci, P. & Hayashizaki, Y., 1999, Methods Enzymol. 303: 19-44), and libraries originating from other termites were constructed in accordance with the method of Sugano et al. (Maruyama, K. and S. Sugano, 1994, Gene 138 (1-2): 171-174). The *Reticulitermes speratus* cDNA library was subcloned into plasmids using the *E. coli* SOLR strain and the ExAssist helper phage (Novagen) in accordance with the instructions.

Example 3

Sequence Analysis

The obtained *E. coli* clones were cultured in LB medium and purified using a MultiScreen FB (Nihon Millipore) in accordance with the appended instructions. With the use of purified plasmid DNA, the sequences of 917, 920, 1056, 1023, and 921 library clones derived from the symbiotic protists of *Reticulitermes speratus, Hodotermopsis sjostedti, Neotermes koshunensis, Mastotermes darwiniensis*, and Cryptocercidae were determined using a Big dye terminator cycle sequencing kit v 3.1 and an ABI3700, 3100, or 3130 automatic sequencer (Applied Biosystems) in accordance with the conventional technique. The single pass sequences at the 5' ends were determined using the M4 primer (SEQ ID NO:141: 5'-GTT TTC CCA GTC ACG AC-3'). The obtained sequences were subjected to homology analysis via FASTX relative to known sequences accumulated in public databases (DNA database Japan), and annotation was carried out. From among the resultants of annotation, those corresponding to cellulase were selected.

Example 4

Cellulase Sequence Analysis

From among obtained cellulase gene homologues, those corresponding to endoglucanases of the glycosyl hydrolase family 7 were selected. Regarding sequences that are considered to originate from common progenitors based on the lineage analysis of partial sequences (homology: approximately 80% or higher in terms of amino acid sequence), the full-length sequences of 43 clones (SEQ ID NOS: 1 to 43) for GHF5, 34 clones (SEQ ID NOS: 44 to 77) for GHF7CBH, 38 clones (SEQ ID NOS: 78 to 115) for GHF7EG, and 25 clones (SEQ ID NOS: 116 to 140) for GHF45, were determined.

As a result of analysis of the lineage relationship using the obtained sequences via the maximum likelihood-distance matrix method, sequences originating from the symbiotic protists of said termites were found to have developed an independent monophyletic group. Regarding GHF7 (FIG. 1) and GHF45, the enzymes of interest were found to be novel enzymes that differ from equivalent known enzyme genes at the subfamily level. The results also indicate that such genes are homologous genes originating from a single progenitor sequence. Thus, a clone of GHF7EG (Rs2038B-11; encoded by the nucleotide sequence of SEQ ID NO: 79) was used as a representative to construct an expression plasmid for a koji mold (Aspergillus oryzae).

Example 5

Expression and Purification of Cellulase in Koji Mold

Figure 2:
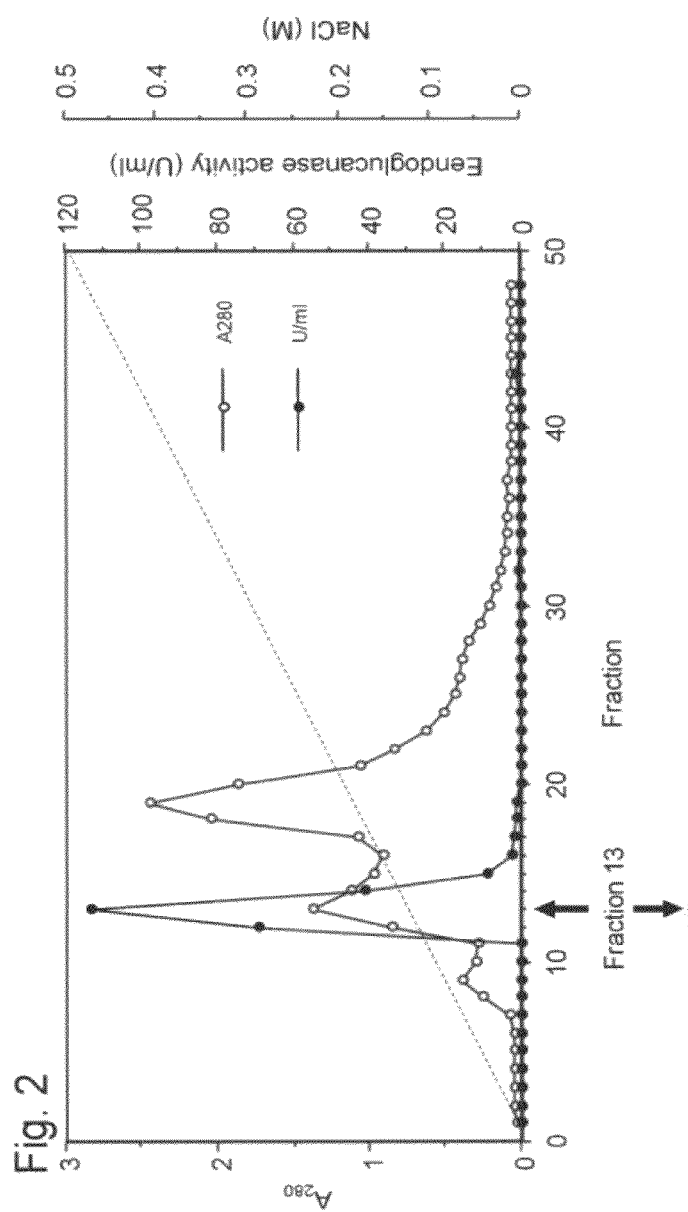
FIG. 2 shows purification of GHF7 endoglucanase (Rs2038B-11; encoded by the nucleotide sequence of SEQ ID NO: 79) by using a HiTrap DEAF column (made by GE Health Care) as described in Example 5 below. The term "1 unit" represents the amount of an enzyme that generates 1 mmol of reducing sugar (a glucose equivalent) per minute.

A cellulase gene portion of the cellulase gene-containing plasmid from which a region encoding the N-terminal signal sequence had been removed, was amplified via PCR and ligated in-frame to a region downstream of the α-amylase promoter and the structural gene. In this case, the KRGGG (SEQ ID NO: 142) sequence for cleaving a fusion protein was inserted into the ligation site. The resulting plasmid was transformed into the NS-tApE koji mold protease double-disrupted strain (niaD⁻ sC⁻ ΔtppA ΔpepE) (Takashi Nemoto, Yasuhiro Watanabe, Jun-ichi Maruyama, Manabu Arioka, and Katsuhiko Kitamoto, "Kouji kin no puroteaze idenshi nijuuhakaikabu niyoru kimoshin no seisan (Production of chymosin by koji mold protease double-disrupted strain)", the Abstracts of Conference of the Society for Biotechnology, Japan, p 131, 2006) to obtain cellulase-producing strains. The koji mold culture supernatant was concentrated via ammonium sulfate precipitation (using 80% saturated ammonium sulfate) and then purified using HiTrap Desalting and HiTrap DEAE (GE health care) in accordance with the appended instructions. When performing the HiTrap DEAE-based purification, 50 mM Tris-HCl (pH 8.0) buffer and a gradient of 0 mM to 500 mM NaCl were used to separate a protein. As a result, the purified protein having cellulase activity, which was observed as a single band on SDS-PAGE at a molecular weight of approximately 45 kDa, was obtained from a fraction of around 130 mM (FIG. 2). As a result of analysis of the amino acid terminal sequence by Edman degradation, the purified enzyme was found to be from the expression plasmid, which had been introduced into koji mold.

Figure 5:
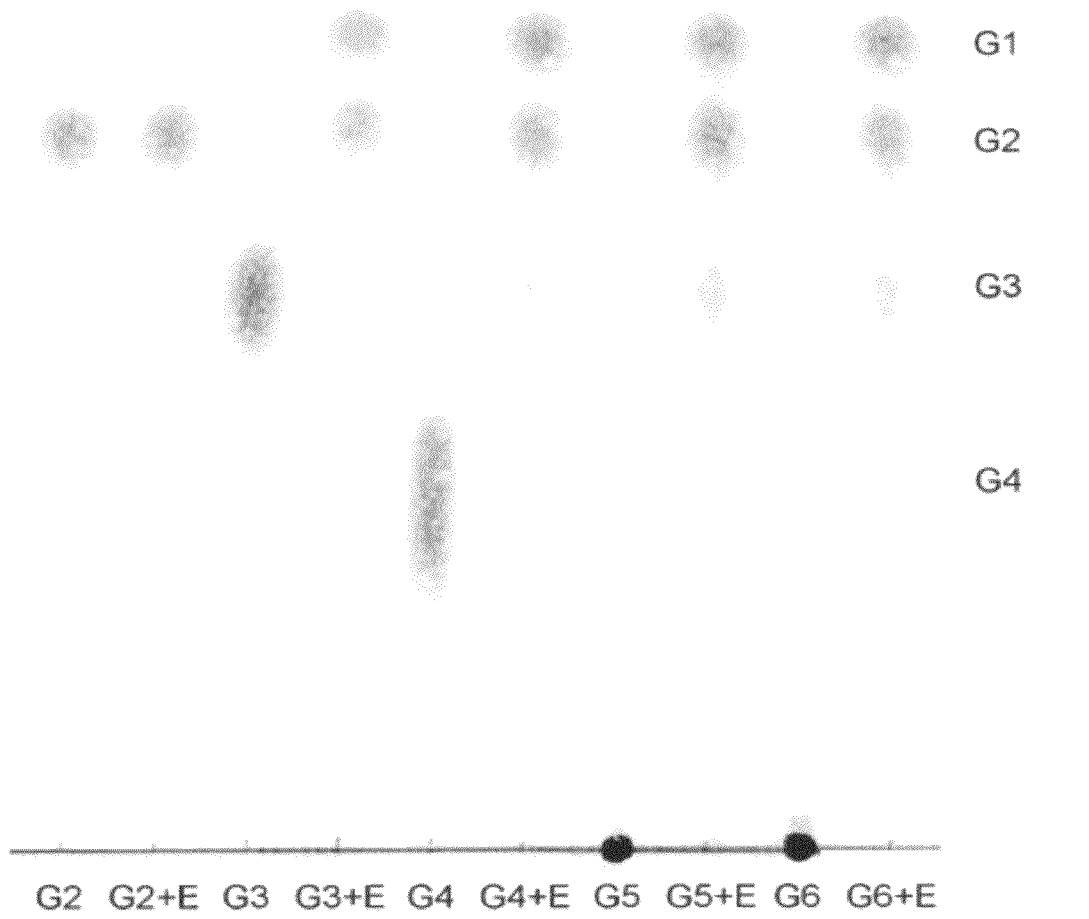
FIG. 5 shows the results of TLC showing degradation products of cellooligosaccharide by the purified cellulase kRs2038B-11; encoded by the nucleotide sequence of SEQ ID NO: 79). The reaction was carried out at 37° C. for 2 hours. In the figure, G1 to G6 each independently represent glucose, cellobiose, cellotriose, cellotetraose, cellopentaose, and cellohexose, and G2+E, G3+E, G4+E, G5+E, and G6+E each independently represent a substrate comprising an enzyme added thereto.

Cellulase activity of this protein was assayed using carboxymethyl cellulose as a substrate (reaction conditions: the activity was assayed in a citrate-phosphate buffer (pH 6.5) for 5 minutes; temperature stability: the activity was assayed at 37° C. for 5 minutes, following treatment for 30 minutes). As a result, the following were found: i.e., optimal pH, 6.5 (FIG. 3A); optimal temperature, 45° C. (FIG. 3B); temperature stability, 40° C. or lower (FIG. 3C); Km, 1.97 mg/ml; and Vmax, 769.6 units/mg protein (FIG. 4). Also, when cellooligosaccharide was subjected to hydrolysis at 37° C. for 2 hours, the final products (i.e., glucose and cellobiose) were generated as major reaction products, while a minor amount of cellotriose was also generated, however, substantially no cellobiose-degrading activity was found (FIG. 5). The term "1 unit (U)" as used herein is defined as the amount of an enzyme that generates a reducing sugar equivalent to 1 μmol glucose per minute.

FIG. 4 demonstrates that the enzyme of the present invention has Vmax and reactivity that are higher than those of other enzymes, and the enzyme of the present invention has a Km value that is substantially equivalent to that of cellulase synthesized by the termites, which is a relatively low value. Further, the Km value is close to the value of a known type of enzyme, indicating that the enzyme of the present invention has high affinity.

Furthermore, cellulase activities on different substrates; i.e., carboxymethyl cellulose (CMC), Avicel, Curdlan, and 3 types of Xylans, were assayed, and the results are shown in Table 1.

TABLE 1

Activity of purified cellulase on different substrates

| Substrate | Linkage | Specific Activity (U/mg protein) |
| --- | --- | --- |
| CMC | β-1,4 | 603 ± 23 |
| Avicel | β-1,4 | 0.12 ± 0.003 |
| Curdlan | β-1,3 | 0.02 ± 0.003 |
| Xylan (beech) | β-1,4 | 0.31 ± 0.009 |
| Xylan (birch) | β-1,4 | 0.40 ± 0.011 |
| Xylan (oat spelt) | β-1,4 | 1.62 ± 0.050 |

Assay was carried out at 37° C. for 60 minutes using a 1.0% (wt/vol) substrate, except for the case of CMC.
"One unit (or units)" for polymer hydrolysis represents an enzyme activity that releases 1 mmol reducing sugar per molecule.

Table 1 indicates that the purified enzyme recognizes CMC as a substrate and does not act on crystalline cellulose by itself, and further that the enzyme has properties such as high endoglucanase activity, low activity as an enzyme when reacting with xylane, and high substrate specificity for cellulose.

Example 6

Expression of Cellulase in Koji Mold and Purification Thereof

Figure 6:
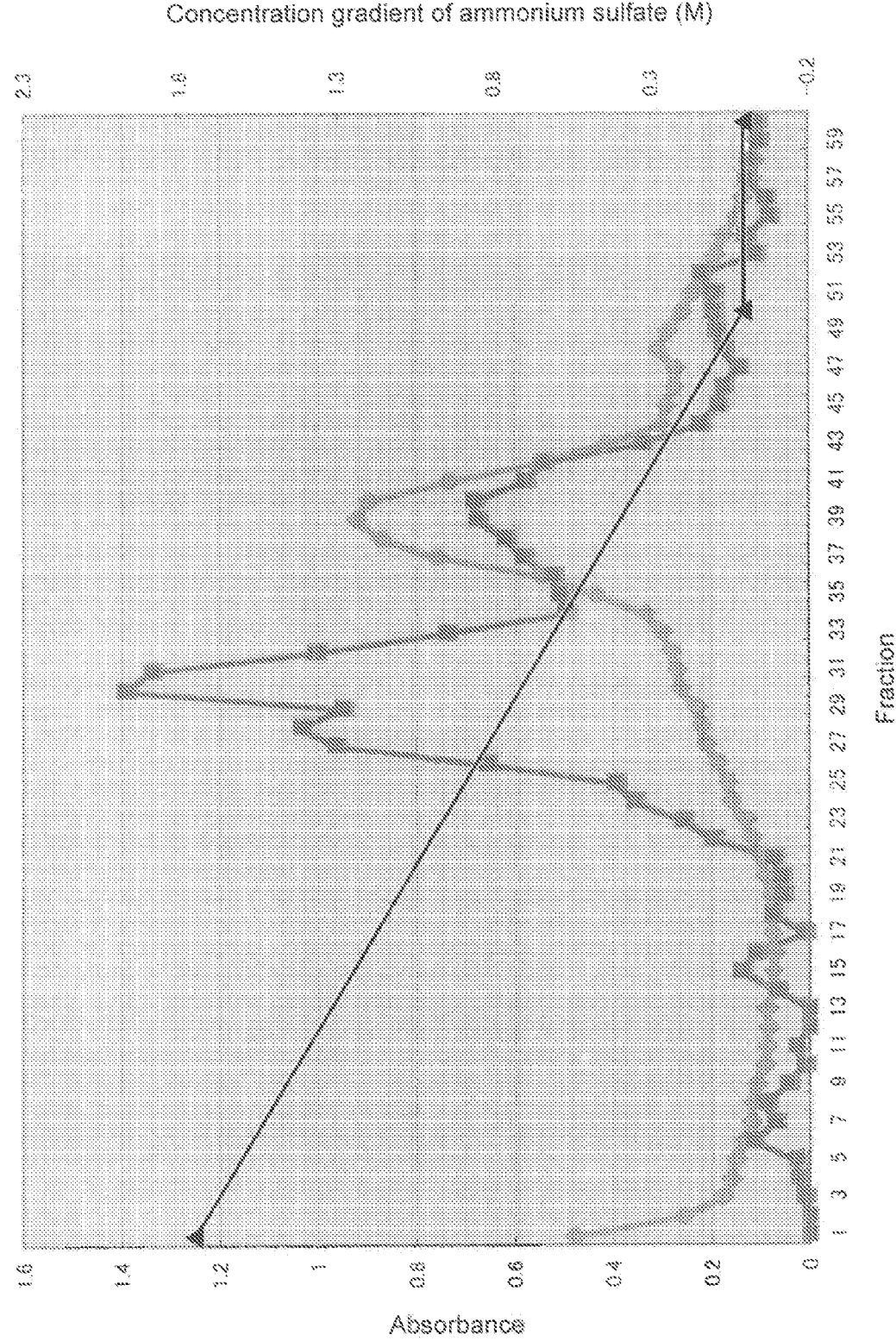
FIG. 6 shows the cellulase active fraction profile of cellulase purification by HiTrapPhenyl sepharose FF from the culture supernatant of the cellulase-producing koji mold prepared in Example 5. In the figure, a rhombus represents cellulase activity (Rs2038B-11; encoded by the nucleotide sequence of SEQ ID NO: 79), a square represents the absorption at 280 nm (A280), and a triangle represents a concentration gradient of ammonium sulfate.
Figure 7:
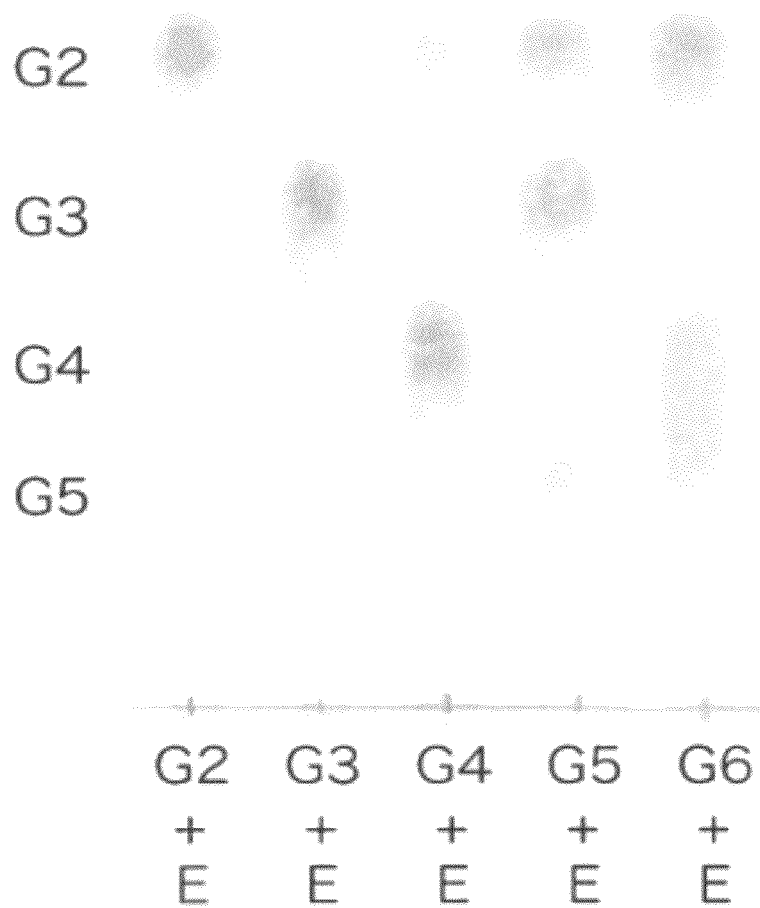
FIG. 7 shows the results of TLC of degradation products generated by hydrolysis of cellooligosaccharides (G2 to G6) at 37° C. for 2 hours using the protein fraction having significant cellulase activity (Rs2038B-11; encoded by the nucleotide sequence of SEQ ID NO: 79; see FIG. 6) fractioned at around 0.35 M ammonium sulfate fractionated in Example 5. G2, cellobiose; G3, cellotriose; G4, cellotetraose; G5, cellopentaose; G6, cellohexose; and E, cellulase (Rs2038B-11).

A cellulase gene portion of the cellulase gene-containing plasmid different from that used in Example 5 from which a region encoding the N-terminal signal sequence had been removed, was amplified via PCR and ligated in-frame to a region downstream of the α-amylase promoter and the structural gene. In this case, the KRGGG (SEQ ID NO: 142) sequence for cleaving a fusion protein was inserted into the ligation site. The resulting plasmid was transformed into the NS-tApE koji mold protease double-disrupted strain (niaD⁻ sC⁻ ΔtppA ΔpepE) (Takashi Nemoto, Yasuhiro Watanabe, Junichi Maruyama, Manabu Arioka, and Katsuhiko Kitamoto, "Koji kin no puroteaze idenshi nijuuhakaikabu niyoru kimoshin no seisan (Production of chymosin by koji mold protease double-disrupted strain)", the Abstracts of Conference of the Society for Biotechnology, Japan, p 131, 2006) to obtain cellulase-producing strains. The koji mold culture supernatant was concentrated by ammonium sulfate precipitation (using 80% saturated ammonium sulfate) and then purified using HiTrap Desalting and HiTrap Phenyl sepharose FF (GE health care) in accordance with the appended instructions. When performing the HiTrapPhenyl sepharose FF-based purification, 50 mM sodium acetate buffer (pH 8.0) and an ammonium sulfate gradient (i.e., a concentration gradient) from 1.7 mM to 0 M were used to separate a protein. As a result, the protein fraction having cellulase activity was obtained in a fraction around 0.35 M (FIG. 6). When cellooligosaccharide was subjected to hydrolysis with this protein at 37° C. for 2 hours, the final products (i.e., glucose and cellobiose) were generated as major reaction products, while substantially no further cellobiose-degrading activity was found (FIG. 7).

In general, endoglucanase is capable of degrading approximately 4 to 5 continuous sugar chains only. From FIGS. 5 and 7, although the enzyme of the present invention is endoglucanase, the possibility that the final product of the enzyme is a cellobiose-glucose unit (which is considered as a general property) is very high, the efficiency in saccharification was found to be very high, and the process was found to be simplified.

As described in the above-described examples, the present inventors have now discovered 140 novel different cellulases, which are carried by the symbiotic protists consisting of four termites and one roach that efficiently degrade cellulosic biomass. Use of such cellulases alone or in combination enabled efficient degradation of cellulose, and use of the koji mold expression system enabled cellulase expression at a high level.

INDUSTRIAL APPLICABILITY

According to the present invention, cellulases suitable for an intended application are selected from among many cellulases and are used alone or in combination, and such cellulases can be used as an enzyme source for advanced saccharification of ligneous biomass, alcohol production, and production of biopolymers, as well as a main or supplementary component of a detergent, a preparation for fiber processing, a feed additive, a digestive aid, and a biopolymer.

All publications, patents, and patent applications cited herein are incorporated herein by reference in their entirety.

The invention claimed is:

1. An isolated DNA encoding a cellulase enzyme from an intestinal symbiotic protist of an insect of *Reticulitermes speratus*, wherein the DNA consists of the nucleotide sequence shown in SEQ ID NO: 79 or a nucleotide sequence having at least 95% identity therewith, and wherein the cellulase enzyme has an endoglucanase activity.

2. A vector comprising the DNA according to claim 1.

3. The vector according to claim 2, which further comprises a promoter that regulates the expression of the DNA.

4. A transformed cell, which comprises the vector according to claim 2.

5. The transformed cell according to claim 4, which is a koji mold cell.

6. The transformed cell according to claim 5, wherein the koji mold is *Aspergillus oryzae*.

7. A method for producing a cellulase enzyme, comprising culturing the transformed cell according to claim 4 in a medium and recovering the cellulase enzyme protein from the cell or the medium wherein the cellulase enzyme has an endoglucanase activity.

* * * * *